(12) United States Patent
White

(10) Patent No.: US 9,700,442 B2
(45) Date of Patent: Jul. 11, 2017

(54) METHODS FOR MANUFACTURING A STENT FRAME

(71) Applicant: Edwards Lifesciences CardiAQ LLC, Irvine, CA (US)

(72) Inventor: Jennifer K. White, Charlestown, RI (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 311 days.

(21) Appl. No.: 14/538,705

(22) Filed: Nov. 11, 2014

(65) Prior Publication Data

US 2015/0135506 A1    May 21, 2015

Related U.S. Application Data

(60) Provisional application No. 61/902,726, filed on Nov. 11, 2013.

(51) Int. Cl.
*A61F 2/24* (2006.01)
*A61F 2/86* (2013.01)

(52) U.S. Cl.
CPC .............. *A61F 2/86* (2013.01); *A61F 2/2415* (2013.01); *A61F 2/2418* (2013.01); *A61F 2/243* (2013.01); *A61F 2/2427* (2013.01); *A61F 2220/0025* (2013.01); *A61F 2220/0041* (2013.01); *A61F 2220/0091* (2013.01); *A61F 2230/0058* (2013.01); *A61F 2240/001* (2013.01); *A61F 2240/005* (2013.01); *A61F 2250/001* (2013.01);
(Continued)

(58) Field of Classification Search
CPC ............. Y10T 29/49895; A61F 2/2427; A61F 2/2415; A61F 2220/0091; A61F 2220/0041; A61F 2220/0025; A61F 2240/001; A61F 2240/005
See application file for complete search history.

(56) References Cited

U.S. PATENT DOCUMENTS 3,548,417 A    12/1970    Kischer et al.
4,289,123 A    9/1981    Dunn
(Continued)

FOREIGN PATENT DOCUMENTS

EP    1671608 B1    7/2008
EP    1343438 B1    7/2009
(Continued)

OTHER PUBLICATIONS

International Preliminary Report on Patentability received for PCT Patent Application No. PCT/US2009/051324, mailed on Feb. 3, 2011, 7 pages.
(Continued)

*Primary Examiner* — Jermie Cozart
(74) *Attorney, Agent, or Firm* — Klarquist Sparkman LLP; AnnMarie Kaiser

(57) ABSTRACT

A support structure includes strut members interconnected by articulated joints to form a series of linked scissor mechanisms. The structure can be remotely actuated to compress or expand its shape by adjusting the scissor joints within a range of motion. In particular, the support structure can be repositioned within the body lumen or retrieved from the lumen. The support structure can be employed to introduce and support a prosthetic valve within a body lumen.

21 Claims, 71 Drawing Sheets

(52) U.S. Cl.
CPC .... *Y10T 29/49826* (2015.01); *Y10T 29/49895* (2015.01)

(56) References Cited

U.S. PATENT DOCUMENTS

| | | |
|---|---|---|
| 5,122,154 A | 6/1992 | Rhodes |
| 5,171,278 A | 12/1992 | Pisharodi |
| 5,503,497 A | 4/1996 | Dudley et al. |
| 5,545,214 A | 8/1996 | Stevens |
| 5,593,417 A | 1/1997 | Rhodes |
| 5,643,339 A | 7/1997 | Kavteladze et al. |
| 5,735,842 A | 4/1998 | Krueger et al. |
| 5,776,181 A | 7/1998 | Lee et al. |
| 5,827,321 A | 10/1998 | Roubin et al. |
| 5,871,536 A | 2/1999 | Lazarus |
| 5,968,091 A | 10/1999 | Pinchuk et al. |
| 6,063,113 A | 5/2000 | Kavteladze et al. |
| 6,146,394 A | 11/2000 | Morejohn et al. |
| 6,183,517 B1 | 2/2001 | Suddaby |
| 6,245,102 B1 | 6/2001 | Jayaraman |
| 6,261,318 B1 | 7/2001 | Lee et al. |
| 6,348,061 B1 | 2/2002 | Whitman |
| 6,454,799 B1 | 9/2002 | Schreck |
| 6,475,237 B2 | 11/2002 | Drasler et al. |
| 6,530,952 B2 | 3/2003 | Vesely |
| 6,569,196 B1 | 5/2003 | Vesely |
| 6,596,021 B1 | 7/2003 | Lootz |
| 6,666,885 B2 | 12/2003 | Moe |
| 6,685,737 B1 | 2/2004 | Pacetti |
| 6,716,230 B2 | 4/2004 | Whitman |
| 6,730,118 B2 | 5/2004 | Spenser et al. |
| 6,872,226 B2 | 3/2005 | Cali et al. |
| 6,893,460 B2 | 5/2005 | Spenser et al. |
| 7,007,396 B2 | 3/2006 | Rudko et al. |
| 7,011,681 B2 | 3/2006 | Vesely |
| 7,041,132 B2 | 5/2006 | Quijano et al. |
| 7,056,338 B2 | 6/2006 | Shanley et al. |
| 7,097,658 B2 | 8/2006 | Oktay |
| 7,141,063 B2 | 11/2006 | White et al. |
| 7,186,265 B2 | 3/2007 | Sharkawy et al. |
| 7,329,279 B2 | 2/2008 | Haug et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,402,169 B2 | 7/2008 | Killion et al. |
| 7,404,823 B2 | 7/2008 | Gregorich et al. |
| 7,429,268 B2 | 9/2008 | Shanley et al. |
| 7,431,732 B2 | 10/2008 | Moriuchi et al. |
| 7,438,721 B2 | 10/2008 | Doig et al. |
| 7,458,985 B2 | 12/2008 | Madda et al. |
| 7,479,158 B2 | 1/2009 | Gregorich |
| 7,491,227 B2 | 2/2009 | Yang |
| 7,500,986 B2 | 3/2009 | Lye et al. |
| 7,500,988 B1 | 3/2009 | Butaric et al. |
| 7,503,930 B2 | 3/2009 | Sharkawy et al. |
| 7,510,570 B1 | 3/2009 | Goicoechea et al. |
| 7,510,575 B2 | 3/2009 | Spenser et al. |
| 7,582,110 B2 | 9/2009 | Case et al. |
| 7,591,848 B2 | 9/2009 | Allen |
| 7,594,974 B2 | 9/2009 | Cali et al. |
| 7,597,710 B2 | 10/2009 | Obermiller |
| 7,628,802 B2 | 12/2009 | White et al. |
| 8,226,707 B2 | 7/2012 | White |
| 8,603,160 B2 | 12/2013 | Salahieh et al. |
| 8,685,080 B2 | 4/2014 | White |
| 2003/0005567 A1* | 1/2003 | Pommer ............... B32B 37/10 29/433 |
| 2003/0014105 A1 | 1/2003 | Cao |
| 2003/0040791 A1 | 2/2003 | Oktay |
| 2003/0191524 A1 | 10/2003 | Hong et al. |
| 2005/0137688 A1 | 6/2005 | Salahieh et al. |
| 2005/0283231 A1 | 12/2005 | Haug et al. |
| 2006/0111772 A1 | 5/2006 | White et al. |
| 2006/0135964 A1 | 6/2006 | Vesely |
| 2008/0004696 A1 | 1/2008 | Vesely |
| 2008/0071356 A1 | 3/2008 | Greenhalgh et al. |
| 2008/0125859 A1 | 5/2008 | Salahieh et al. |
| 2008/0183275 A1 | 7/2008 | Schmid et al. |
| 2009/0054969 A1 | 2/2009 | Salahieh et al. |
| 2009/0082844 A1 | 3/2009 | Zacharias et al. |
| 2009/0210052 A1 | 8/2009 | Forster et al. |
| 2009/0240320 A1 | 9/2009 | Tuval et al. |
| 2010/0004739 A1 | 1/2010 | Vesely |
| 2011/0106115 A1 | 5/2011 | Haselby et al. |
| 2011/0219603 A1 | 9/2011 | White |
| 2011/0224781 A1 | 9/2011 | White |
| 2011/0230956 A1 | 9/2011 | White |
| 2011/0238152 A1 | 9/2011 | Richter |
| 2011/0245918 A1 | 10/2011 | White |
| 2011/0288629 A1 | 11/2011 | White |
| 2011/0288632 A1 | 11/2011 | White |
| 2012/0296418 A1 | 11/2012 | Bonyuet et al. |
| 2013/0025110 A1 | 1/2013 | Stankus et al. |
| 2013/0046373 A1 | 2/2013 | Cartledge et al. |
| 2013/0204359 A1 | 8/2013 | Thubrikar et al. |

FOREIGN PATENT DOCUMENTS

| | | |
|---|---|---|
| EP | 1872743 B1 | 8/2009 |
| EP | 1049425 B1 | 11/2009 |
| EP | 2138132 A2 | 12/2009 |
| JP | 52-62850 A | 5/1977 |
| JP | 59-8499 U | 1/1984 |
| JP | 5-317204 A | 12/1993 |
| JP | 7-2396 U | 1/1995 |
| JP | 3071573 U | 9/2000 |
| JP | 2007-534381 A | 11/2007 |
| JP | 2008-29506 A | 2/2008 |
| WO | 95/13033 A1 | 5/1995 |
| WO | 99/33414 A1 | 7/1999 |
| WO | 02/49540 A2 | 6/2002 |
| WO | 02/49540 A3 | 2/2003 |
| WO | 03/018100 A1 | 3/2003 |
| WO | 03/047468 A1 | 6/2003 |
| WO | 03/075797 A2 | 9/2003 |
| WO | 2005/102015 A2 | 11/2005 |
| WO | 2006/111772 A2 | 10/2006 |
| WO | 2006/116761 A2 | 11/2006 |
| WO | 2006/111772 A3 | 12/2006 |
| WO | 2005/102015 A3 | 4/2007 |
| WO | 2008/015257 A2 | 2/2008 |
| WO | 2008/015257 A3 | 4/2008 |
| WO | 2008/051428 A2 | 5/2008 |
| WO | 2008/051428 A3 | 7/2008 |
| WO | 2008/088835 A1 | 7/2008 |
| WO | 2009/026272 A1 | 2/2009 |
| WO | 2006/116761 A3 | 4/2009 |
| WO | 2009/070180 A1 | 6/2009 |
| WO | 2010/011699 A2 | 1/2010 |
| WO | 2010/011699 A3 | 5/2010 |
| WO | 2012/032187 A1 | 3/2012 |
| WO | 2013/106585 A1 | 7/2013 |

OTHER PUBLICATIONS

International Search Report and Written Opinion received for PCT Patent Application No. PCT/US2009/051324 mailed on Mar. 30, 2010, 10 pages.

International Preliminary Report on Patentability received for PCT Patent Application No. PCT/US2013/021052, mailed on Jul. 24, 2014, 9 pages.

International Search Report and Written Opinion received for PCT Patent Application No. PCT/US2013/021052, mailed on Jun. 10, 2013, 12 pages.

International Search Report and Written Opinion received for PCT Patent Application No. PCT/US2014/023788, mailed on Sep. 10, 2014, 16 pages.

Invitation to pay additional fees received for PCT Patent Application No. PCT/US2014/023788, mailed on Jul. 1, 2014, 2 pages.

Office Action received for Australian Patent Application No. 2009274131, mailed on May 6, 2014, 4 pages.

(56) References Cited

OTHER PUBLICATIONS

Office Action received for Canadian Patent Application No. 2,731,551, mailed on Nov. 12, 2014, 3 pages.
Decision to Grant received for Chinese Patent Application No. 200980136513.2, mailed on Dec. 2, 2014, 4 pages (2 pages of English Translation and 2 pages of Official Copy).
Office Action received for Chinese Patent Application No. 200980136513.2, mailed on Jul. 28, 2014, 5 pages (2 pages of English Translation and 3 pages of Official Copy).
Office Action Received for Japanese Patent Application No. 2011-520148, mailed on Dec. 22, 2014, 6 pages (3 pages of English Translation and 3 pages of Official Copy).
Final Office Action received for U.S. Appl. No. 13/055,441, mailed on Aug. 23, 2013, 10 pages.
Non-Final Office Action received for U.S. Appl. No. 13/055,441, mailed on Feb. 12, 2013, 9 pages.
Notice of Allowance received for U.S. Appl. No. 13/055,441, mailed on Nov. 12, 2013, 11 pages.
Final Office Action received for U.S. Appl. No. 13/069,037, mailed on Jan. 29, 2014, 5 pages.
Non-Final Office Action received for U.S. Appl. No. 13/069,037, mailed on Jun. 20, 2014, 6 pages.
Notice of Allowance received for U.S. Appl. No. 13/069,037, mailed on Jan. 26, 2015, 7 pages.
Advisory Action received for U.S. Appl. No. 13/111,855, mailed on Jan. 29, 2014, 2 pages.
Final Office Action received for U.S. Appl. No. 13/111,855, mailed on Nov. 26, 2013, 9 pages.
Final Office Action received for U.S. Appl. No. 13/111,855, mailed on Oct. 6, 2014, 8 pages.
Non-Final Office Action received for U.S. Appl. No. 13/111,855, mailed on Jan. 4, 2013, 9 pages.
Non-Final Office Action received for U.S. Appl. No. 13/111,855, mailed on Mar. 28, 2014, 8 pages.
Notice of Allowance received for U.S. Appl. No. 13/111,855, mailed on Dec. 19, 2014, 7 pages.
Final Office Action received for U.S. Appl. No. 13/113,887, mailed on Dec. 16, 2013, 7 pages.
Final Office Action received for U.S. Appl. No. 13/113,887, mailed on Jun. 20, 2014, 7 pages.
Non-Final Office Action received for U.S. Appl. No. 13/113,887, mailed on Apr. 24, 2013, 6 pages.
Notice of Allowance received for U.S. Appl. No. 13/113,887, mailed on Aug. 29, 2014, 7 pages.
Non-Final Office Action received for U.S. Appl. No. 13/113,890, mailed on Aug. 19, 2014, 8 pages.
Final Office Action received for U.S. Appl. No. 13/158,232, mailed on Apr. 11, 2014, 12 pages.
Non Final Office Action received for U.S. Appl. No. 13/158,232, mailed on Oct. 21, 2014, 10 pages.
Non-Final Office Action received for U.S. Appl. No. 13/158,232, mailed on Nov. 8, 2013, 8 pages.
International Search Report and Written Opinion received for PCT Patent Application No. PCT/US2014/065089 mailed on Feb. 24, 2015, 12 pages.
Office Action Received for Israeli Patent Application No. 230266, mailed on Apr. 2, 2015, 4 pages (2 pages of English Translation and 2 pages of Official Copy).

* cited by examiner

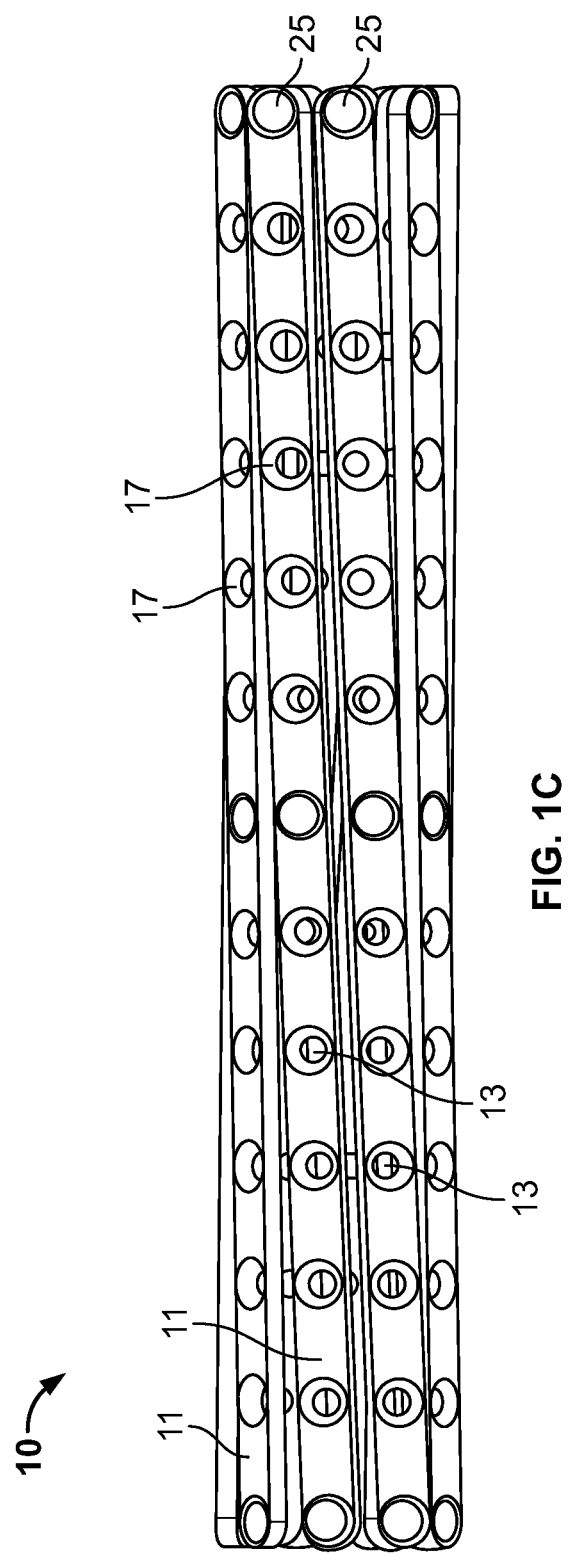

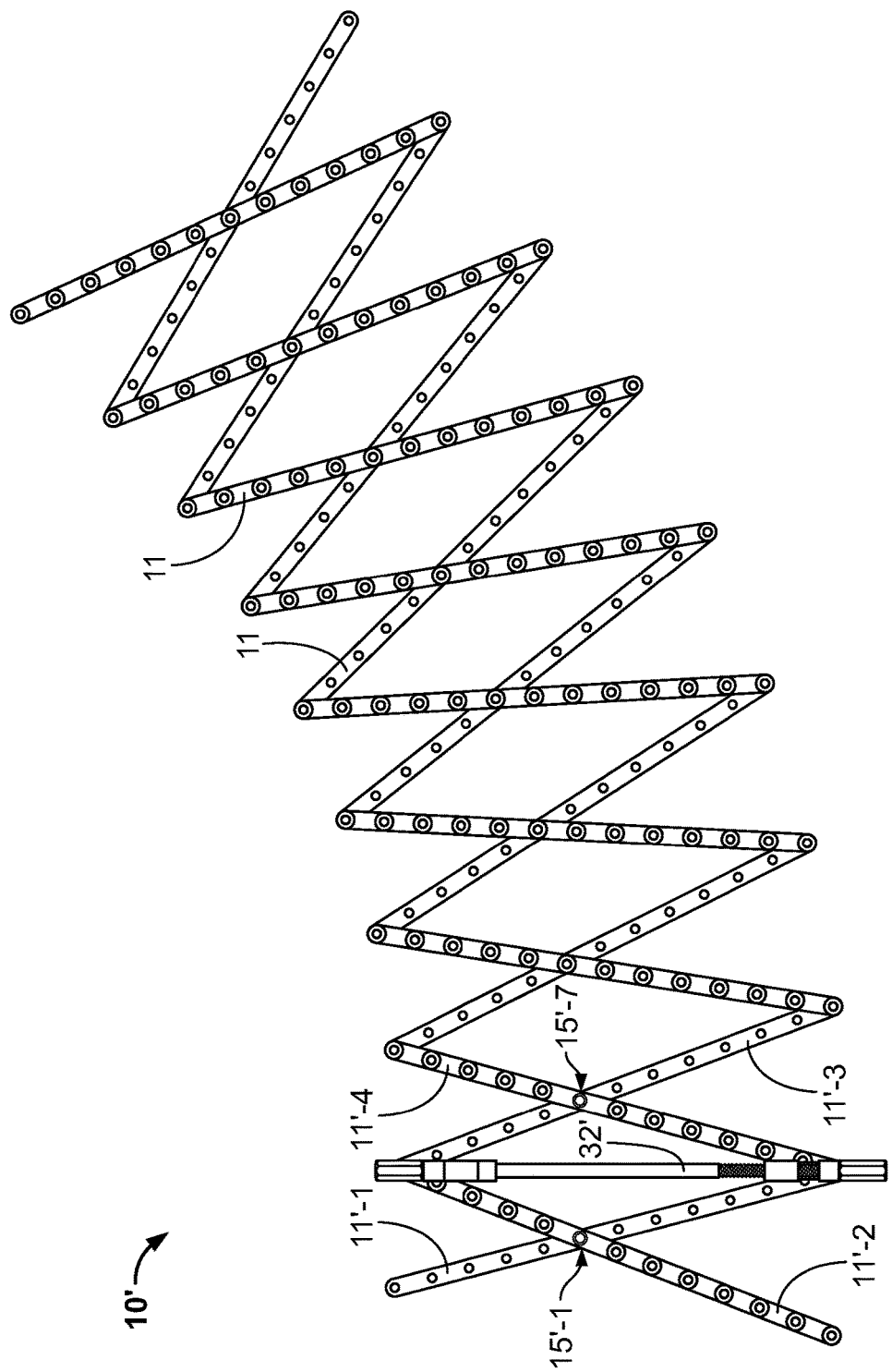

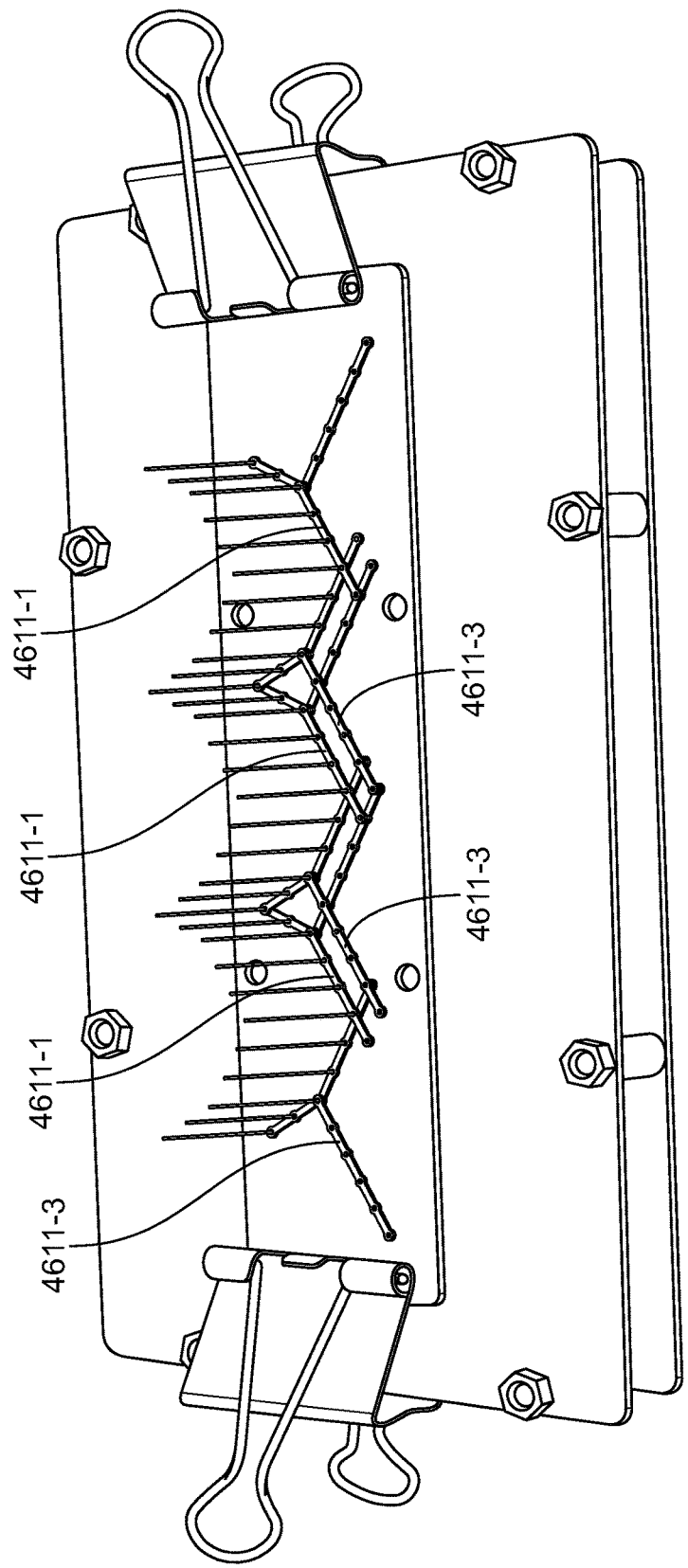

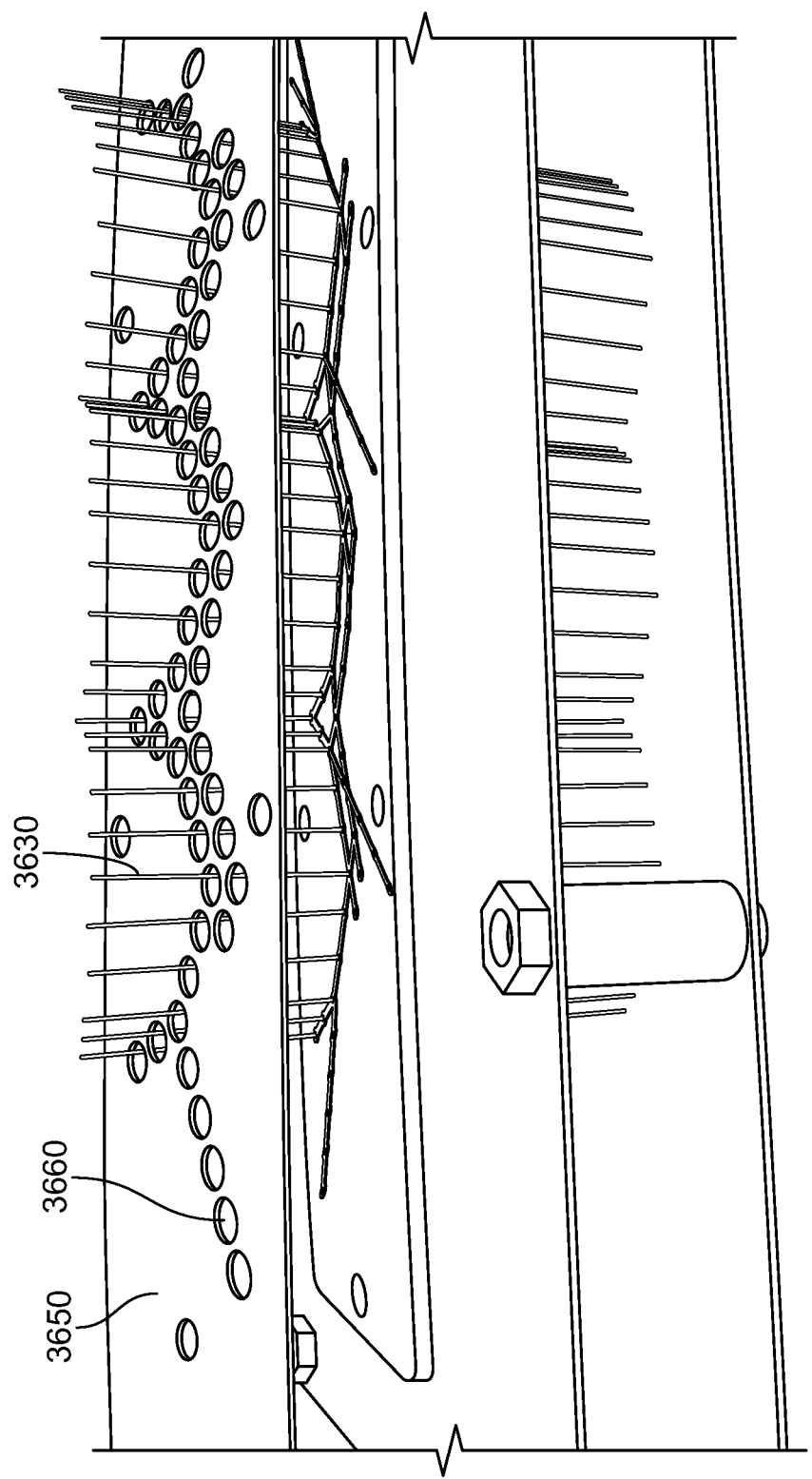

METHODS FOR MANUFACTURING A STENT FRAME

CROSS-REFERENCE TO RELATED APPLICATIONS

This application claims priority to U.S. Provisional Application No. 61/902,726 filed on Nov. 11, 2013, which is hereby incorporated by reference in its entirety.

BACKGROUND

Endoluminal stents can be implanted in a vessel or tract of a patient to help maintain an open lumen. The stents can also be used as a frame to support a prosthetic device or to deliver a therapeutic agent. Stents can be implanted by either an open operative procedure or a closed operative procedure. When an option exists, the less invasive closed procedure is generally preferred because the stent can be guided through a body lumen, such as the femoral artery, to its desired location.

Closed procedures typically use one of two techniques. One closed procedure employs balloon catheterization where an expandable stent encloses an inflatable balloon. In this procedure, the stent is implanted by inflating the balloon, which causes the stent to expand. The actual positioning of the stent cannot be determined until after the balloon is deflated and, if there is a misplacement of the stent, the process cannot be reversed to reposition the stent.

The other closed procedure employs a compressed stent enclosed by a removable sheath. In this procedure, a stent made from a shape memory alloy, such as Nitinol, is held in a compressed state by a sheath. The stent is implanted by withdrawing the sheath, causing the stent to expand to its nominal shape. Again, if there is a misplacement of the stent, the process cannot be reversed to reposition the stent.

Positioning errors are particularly dangerous when the stent is used to support a cardiac valve. Serious complications and patient deaths have occurred due to malpositioning of the valve at the implant site in the body, using the available stent-mounted valves. Malpositioning of the valve has resulted in massive paravalvular leakage, device migration, and coronary artery obstruction. The majority of these complications were unavoidable, but detected at the time of the procedure. However, due to inability to reposition or retrieve the device, these problems were impossible to reverse or mitigate during the procedure.

SUMMARY

An endoluminal support structure or stent in accordance with certain embodiments of the invention solves certain deficiencies found in the prior art. In particular, the support structure can be repositioned within the body lumen or retrieved from the lumen.

A particular embodiment of the invention includes a support apparatus implantable within a biological lumen. The support apparatus can include a plurality of elongated strut members interlinked by a plurality of rotatable joints, wherein the rotatable joints can cooperate with the stent members to adjustably define a shaped structure between a compressed orientation and an expanded orientation.

More particularly, the shaped structure can be one of a cylindrical, a conical, or an hourglass shape. A rotatable joint can form a scissor mechanism with a first strut member and a second strut member. Furthermore, the strut members can be arranged as a series of linked scissor mechanisms. The apparatus can further include an actuator to urge the rotatable joints within a range of motion.

The apparatus can also include a prosthetic valve coupled to the shaped structure.

Another particular embodiment of the invention can include a medical stent implantable within a biological lumen. The medical stent can include a plurality of elongated strut members, including a first strut member and a second strut member, and an articulated joint connecting the first strut member and the second strut member.

In particular, the articulated joint can form a scissor mechanism with the first strut member and the second strut member. The articulated joint can bisect the first strut member and the second strut member. The articulated joint can interconnect a first end of the first strut member with a first end of the second strut member.

The plurality of strut members can be arranged as a series of linked scissor mechanisms. The strut members can also be non-linear. The strut members can be arranged to form one of a cylindrical, a conical, or an hourglass shape.

The stent can further include an adjustment mechanism to exert a force to urge the strut members about the articulated joint within a range of motion.

The stent can include a prosthetic valve coupled to the strut members.

Specific embodiments of the invention can include prosthetic valves that are rotatable or conventional.

A rotatable prosthetic valve can include a first structural member coupled to the strut members, a second structural member rotatable relative to the first structural member, and a plurality of pliable valve members connecting the first structural member with the second structural member such that rotation of the second structural member relative to the first structural member can urge the valve members between an open and a closed state. In particular, the rotation of the second structural member can be responsive to the natural flow of a biological fluid.

A conventional prosthetic valve can include a plurality of pliable valve leaflets having commissures at the intersection of two strut members. The prosthetic valve can further include a skirt material coupled to the strut members.

These structures can also be interconnected in various combinations.

A particular advantage of a support structure in accordance with embodiments of the invention is that it enables a prosthetic valve to be readily retrieved and repositioned in the body. If following deployment, the valve is malpositioned or deemed dysfunctional, the support structure allows the valve to be readily repositioned and re-deployed at a new implant site, or removed from the body entirely. This feature of the device can prevent serious complications and save lives by enabling the repair of mal-positioned devices in the body.

Also described here are methods of fabricating an articulated support structure. In some variations, the method comprises placing a plurality of pins through openings in an alignment plate, placing a plurality of eyelets onto the plurality of pins, layering a plurality of strut members each having a plurality of orifices onto the plurality of pins by placing the pins through the orifices, connecting the plurality of strut members into a chain having a first end and a second end by swaging the eyelets, and wrapping the chain into a tubular structure by connecting the first and second ends of the chain. In some of these variations, the method further comprises placing a plurality of valve leaflets onto the plurality of pins, wherein at least one of the plurality of strut members is layered below each valve leaflet, and at least one of the plurality of strut members is layered above each valve leaflet. In some of these variations, the method further comprises biasing the valve leaflets into a closed configuration after wrapping the chain into a tubular structure, by rotating at least one of the plurality of strut members from a first position to a second position. In some of these variations, the method further comprises placing a skirt material onto the plurality of pins, wherein at least one of the plurality of strut members is layered below the skirt material, and at least one of the plurality of strut members is layered above the skirt material. In some of these variations, the method further comprises attaching an actuator to the articulated support structure, wherein the actuator is configured to reversibly and incrementally adjust the articulated support structure between an expanded configuration and a compressed configuration. In some of these variations, the method further comprises attaching the articulated support structure to a second articulated support structure. In some of these variations, the method further comprises attaching an actuator to the second articulated support structure, wherein the actuator is configured to reversibly and incrementally adjust the articulated support structure and the second articulated support structure between an expanded configuration and a compressed configuration. In some variations, the method further comprises placing a skirt material onto the plurality of pins, wherein at least one of the plurality of strut members is layered below the skirt material, and at least one of the plurality of strut members is layered above the skirt material. In some of these variations, the method further comprises attaching the articulated support structure to a second articulated support structure. In some of these variations, the method further comprises attaching an actuator to the articulated support structure, wherein the actuator is configured to reversibly and incrementally adjust the articulated support structure and the second articulated support structure between an expanded configuration and a compressed configuration. In other variations, the method may comprise placing skirt material onto the plurality of pins prior to placement of any strut members. The method may also comprise tucking the skirt material in between at least two of the plurality of strut members. The tucking may be performed without using any sutures attached to the skirt material, and may comprise using one or more wrapping or folding pin to pierce the skirt material and then pivoting the pin against one strut of the plurality of strut members to wrap the skirt material over the one strut. The wrapping or folding pin may be inserted against an adjacent strut to wrap the skirt material around the strut. The wrapping or folding pin may then be further pushed or inserted temporarily under the strut after wrapping the skirt material over the one strut. The skirt material may be held against the strut by piercing the skirt material at two different locations with the pin. A second strut is then attached to the valve assembly and the wrapping or folding may then be removed from the skirt material.

In some variations, the method of fabricating an articulated support structure comprises interlinking a plurality of strut members into a flattened chain having a first end and a second end, wherein each of the plurality of strut members comprises a plurality of orifices, comprising placing a plurality of alignment guides through at least one orifice of each of the plurality of strut members, wherein each of the plurality of alignment guides is placed through the orifices of at least two strut members, securing the at least two strut members together, removing the plurality of alignment guides from the orifice, and connecting the first end of the flattened chain to the second end of the flattened chain to form a tubular structure. In some of these variations, the method further comprises securing a valve comprising a plurality of valve leaflets to the support structure, wherein securing the valve to the support structure comprises sandwiching the valve leaflets between the strut members. In some of these variations, the plurality of strut members comprises a plurality of coaptation strut members. In some of these variations, the method further comprises further comprising rotating the coaptation struts from a first position to a second position to bias the valve toward a closed configuration. In some variations, the method further comprises securing a skirt to the support structure, wherein securing the skirt to the support structure comprises sandwiching the skirt between the strut members. In some of these variations, the method further comprises interlinking a second plurality of strut members into a second flattened chain having a first end and a second end, wherein each of the second plurality of strut members comprises a plurality of orifices, comprising placing a second plurality of alignment guides through at least one orifice of each of the second plurality of strut members, wherein each of the second plurality of alignment guides is placed through the orifices of at least two strut members of the second plurality of strut members, securing the at least two strut members of the second plurality of strut members together, removing the second plurality of alignment guides from the orifice, and connecting the first end of the second flattened chain to the second end of the second flattened chain to form a second tubular structure, and securing a skirt to the second tubular structure, wherein securing the skirt to the second tubular structure comprises sandwiching the skirt between the strut members.

Also described here are articulated support structures configured to be placed in a lumen. In some variations, the articulated support structure comprises a plurality of strut members connected by a plurality of articulated joints into a tubular shape, a plurality of valve leaflets forming a valve, wherein each of the plurality of valve leaflets is sandwiched between at least two of the plurality of strut members, and a skirt configured to help seal the valve in the lumen, wherein the skirt is sandwiched between at least two of the plurality of strut members. In some of these variations, the articulated support structure is reversibly and incrementally adjustable between an expanded configuration and a compressed configuration. In some of these variations, the articulated support structure further comprises an actuator, wherein the actuator is configured to reversibly and incrementally adjust the articulated support structure between an expanded configuration and a compressed configuration. In some variations, the articulated support structure does not comprise any sutures. In some variations, the articulated support structure further comprises a plurality of coaptation struts, wherein the coaptation struts are configured to bias the valve toward a closed configuration.

In another embodiment, an assembly system for an articulated structure, comprising a backing support, the backing support comprising a plurality of backing support strut alignment openings, and a cover plate, the cover support comprising and a plurality of cover support strut alignment openings, wherein the plurality of backing support strut alignment openings are aligned with the plurality of cover support strut alignment openings. The backing support may further comprise indicia along the plurality of backing support strut alignment openings indicating strut positions. The backing support may further comprise at least one swaging alignment structure.

The assembly system may further comprise a plurality of alignment pins configured to reside in the plurality of backing support strut alignment openings and the plurality of cover support strut alignment openings. The assembly system may further comprise a plurality of struts and a plurality of eyelets. The assembly may further comprise a plurality of valve leaflets. The assembly system may further comprise at least one sealing material. Each of the plurality of sealing material sheets may comprise at least one attaching tab. The assembly further comprises a plurality of struts comprising a plurality of primary struts and a plurality of commissure struts. The backing support may further comprise at least one cover support retaining structure. The at least one cover support retaining structure may comprise a clip. At least one of the backing support and the cover support may comprise a support alignment structure configured to facilitate alignment of the backing support and the cover support. The backing support may be a backing plate, and the cover support may be a cover plate. The backing support may further comprise at least one jig alignment structure. The assembly system may further comprise a shim or protective insert. The protective insert may comprise a plurality of alignment openings, and/or may comprise base regions and commissure regions. The base regions may each comprise a triangular shape, and the commissure regions may comprise an elongate shape.

In another embodiment, a medical device is provided, comprising a first plurality of separate struts in a first tubular scissor linkage configuration, wherein at least one strut of the first plurality of separate struts comprises an integrally formed U-shape or V-shape strut. Two or three struts of the first plurality of separate struts may comprise once-piece or integrally formed U-shape or V-shape struts. The first plurality of separate struts may further comprise a plurality of inner struts and a plurality of outer struts configured in the scissor linkage configuration. The integrally formed U-shape or V-shape strut may be attached to one of the first plurality of inner struts and one of the first plurality of outer struts. The U-shape or V-shape strut may comprise an apical opening. The U-shape or V-shape strut may comprise an apical extension the apical opening is located on the apical extension. The medical device may further comprise a sealing structure, the sealing structure comprising at least one base region and at least one extension region, wherein the at least one extension region is coupled to the at least one strut of the first plurality of separate struts comprising the integrally formed U-shape or V-shape strut. The extension region may comprise at least one tab configured to wrap around the at least one strut of the first plurality of separate struts comprising the integrally formed U-shape or V-shape strut. The at least one tab may be sutured to the at least one strut of the first plurality of separate struts comprising the integrally formed U-shape or V-shape strut. The at least one base region comprises may be compressed between two struts of the first plurality of separate struts. The medical device may further comprise a second plurality of separate struts in a second tubular scissor linkage configuration, wherein the first plurality of separate struts is located in a lumen of the second tubular scissor linkage configuration of the secondary plurality of separate struts. The medical device may further comprise at least one valve leaflet attached to at least one strut of the first plurality of separate struts comprises an integrally formed U-shape or V-shape strut.

BRIEF DESCRIPTION OF THE DRAWINGS

The foregoing and other objects, features and advantages of the invention will be apparent from the following more particular description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 1C-1D are perspective views of the support structure of FIG. 1A. FIG. 1D is a perspective view of the support structure of FIG. 1A in a fully expanded state.

FIG. 3 is a perspective view of the arrangement of strut members in a conical-shaped support structure configuration.

DETAILED DESCRIPTION

Figure 1A:
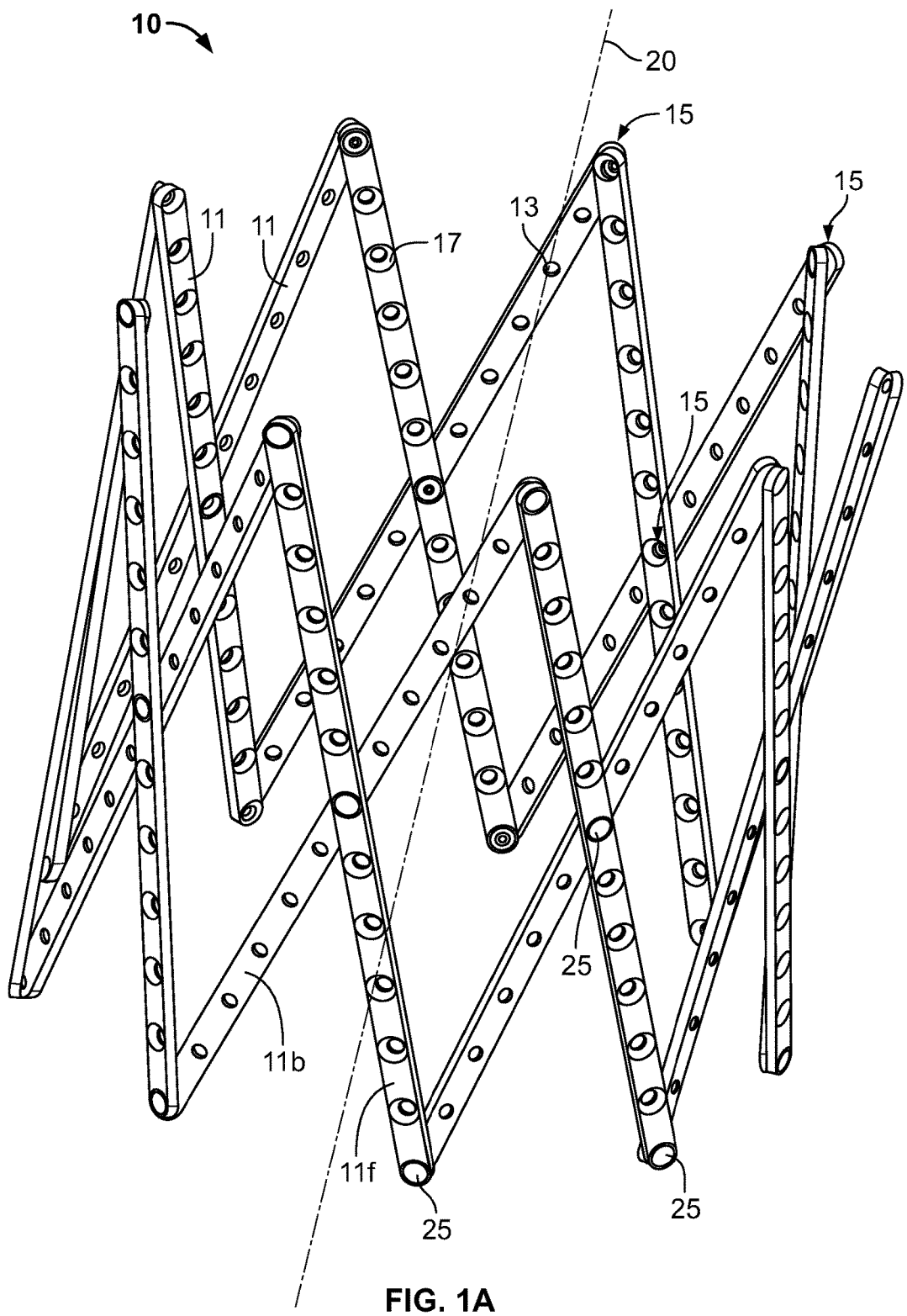
FIG. 1A is a perspective view of a particular endoluminal support structure.

Particular embodiments of the invention include endoluminal support structures (stents) and prosthetic valves. Described herein are endoluminal support structures and valve support structures comprising a plurality of strut members interconnected by articulated joints. The support structures may have a generally cylindrical or tubular shape and may comprise longitudinal axes. The support structures described herein (e.g., support structures 10, 10', 2510, 2710, 3910, 3810, 4610) may be incrementally and reversibly expandable and collapsible between an expanded configuration (i.e., having a greater radius orthogonal to the longitudinal axis) and a compressed or collapsed configuration (i.e., having a smaller radius orthogonal to the longitudinal axis). The longitudinal distances between two strut members may be less in the expanded configuration than in the compressed configuration, while the circumferential distances between two strut members may be greater in the expanded configuration than in the compressed configuration. Similarly, the longitudinal distances between two articulated joints may be less in the expanded configuration than in the compressed configuration, while the circumferential distances between two articulated joints may be greater in the expanded configuration than in the compressed configuration. When compressed, the support structures may be at their maximum length and minimum diameter. When expanded, the support structures may be at their minimum length and maximum diameter. The maximum length may be limited by the length of the strut members, while the minimum diameter may be limited by the width of the strut members. In compressed configurations, the support structure may be highly compact. However, they may retain an open lumen through them while in the compressed configurations.

The strut members may be connected such that the support structures may be moved from compressed configurations to expanded configurations, and the reverse, by a number of different force configurations. For example, the support structures may be moved from an expanded configuration to a compressed configuration by application of radially inward force. The radially inward force may be applied around the full circumference of the support structure, or it may be applied to fewer discrete points about the circumference of the support structure (e.g., two opposing points about the circumference of the support structure, such as two articulated joints on the same diameter of the support structure). Similarly, the support structure may be moved from a compressed configuration to an expanded configuration by application of radially outward force. The radially outward force may be applied around the full circumference of the support structure, or it may be applied to fewer discrete points about the circumference of the support structure (e.g., two opposing points about the circumference of the support structure, such as two articulated joints on the same diameter of the support structure).

The support structure may also be moved from an expanded configuration to a compressed configuration by application of longitudinally oriented forces (i.e., force parallel to the longitudinal axis of the support structure) urging two strut members longitudinally away from each other. The support structure may similarly be moved from a compressed configuration to an expanded configuration by application of longitudinally oriented forces urging two strut members longitudinally toward each other. The application of longitudinally oriented forces at two points may be sufficient to move the support structure from a compressed configuration to an expanded configuration or from an expanded configuration to a compressed configuration.

The support structure may also be moved from an expanded configuration to a compressed configuration by application of circumferentially oriented forces urging two strut members circumferentially toward each other. The support structure may similarly be moved from a compressed configuration to an expanded configuration by application of circumferentially oriented forces urging two strut members circumferentially away from each other. The application of circumferentially oriented forces at two points may be sufficient to move the support structure from a compressed configuration to an expanded configuration or from an expanded configuration to a compressed configuration. In some variations, the forces described above may be applied by an actuator (such as those described herein), and thus an actuator may be used to move the support structure between compressed and expanded configuration, as described in more detail below.

The support structures may comprise a chain of linkages, which may be configured such that the expansion or compression of any individual linkage, in the manner described above, may cause the other linkages to also expand or compress. In such a way, the support structures may be reversibly expanded or compressed by application of force two only two points on the support structure (e.g., force urging two articulated joints apart or towards each other along a longitudinal axis, or force urging two articulated joints apart or towards each other along the circumference of the support structure).

The articulated joints of the support structures described herein may comprise two or more (e.g., three, four, five, six, or more) separate components that may articulate. The articulated joints may in some variations be rotatable joints, such that the two or more components may rotate in one or more planes relative to each other. In some variations, the rotatable joints may be pin joints, such that the two or more components may rotate within a single plane (i.e., single-axis rotation) relative to each other. The axes of rotation of the articulated joints may be perpendicular to the longitudinal axes of the support structures. In some variations, the articulated joints may comprise primary axes of rotation, but may also allow some movement along one or more additional axes (e.g., perpendicular to the primary axis of rotation). In some of these variations, the support structures may comprise longitudinal axes, and the primary axes of rotation of the articulated joints may be perpendicular to the longitudinal axes of the support structures.

This type of articulation may be achieved by any number of methods of interconnection between strut members, but in some variations may use fasteners such as rivets, eyelets, capped pins, screws, bolts, ball-in-socket structures, or nails, which may be integrally formed in the struts (such as a peened semi-sphere interacting with an indentation or orifice, or a male-female coupling) or may be a separate structure. In some variations, the fasteners may be received by orifices spaced along the length of the strut members. The orifices may be countersunk on one side of the strut members to receive the head of a fastener. In some variations the orifices may be of uniform diameter and spacing along the strut member, but neither is required. In addition to being configured to receive fasteners, the orifices may provide an additional pathway for tissue growth-over to stabilize and encapsulate the support structure over time.

Endoluminal Support Structures

FIG. 1A is a perspective view of a particular endoluminal support structure. As shown, the support structure 10 is a medical stent that includes a plurality of longitudinal strut members 11 interconnected by a plurality of articulated joints 15. In particular, the articulated joints 15 may allow the interconnected strut members 11 to rotate relative to each other. The articulated joints may be able to be rotated about an axis of rotation, and/or may be swivelable. As shown, there are eighteen struts 11.

Figure 1B:
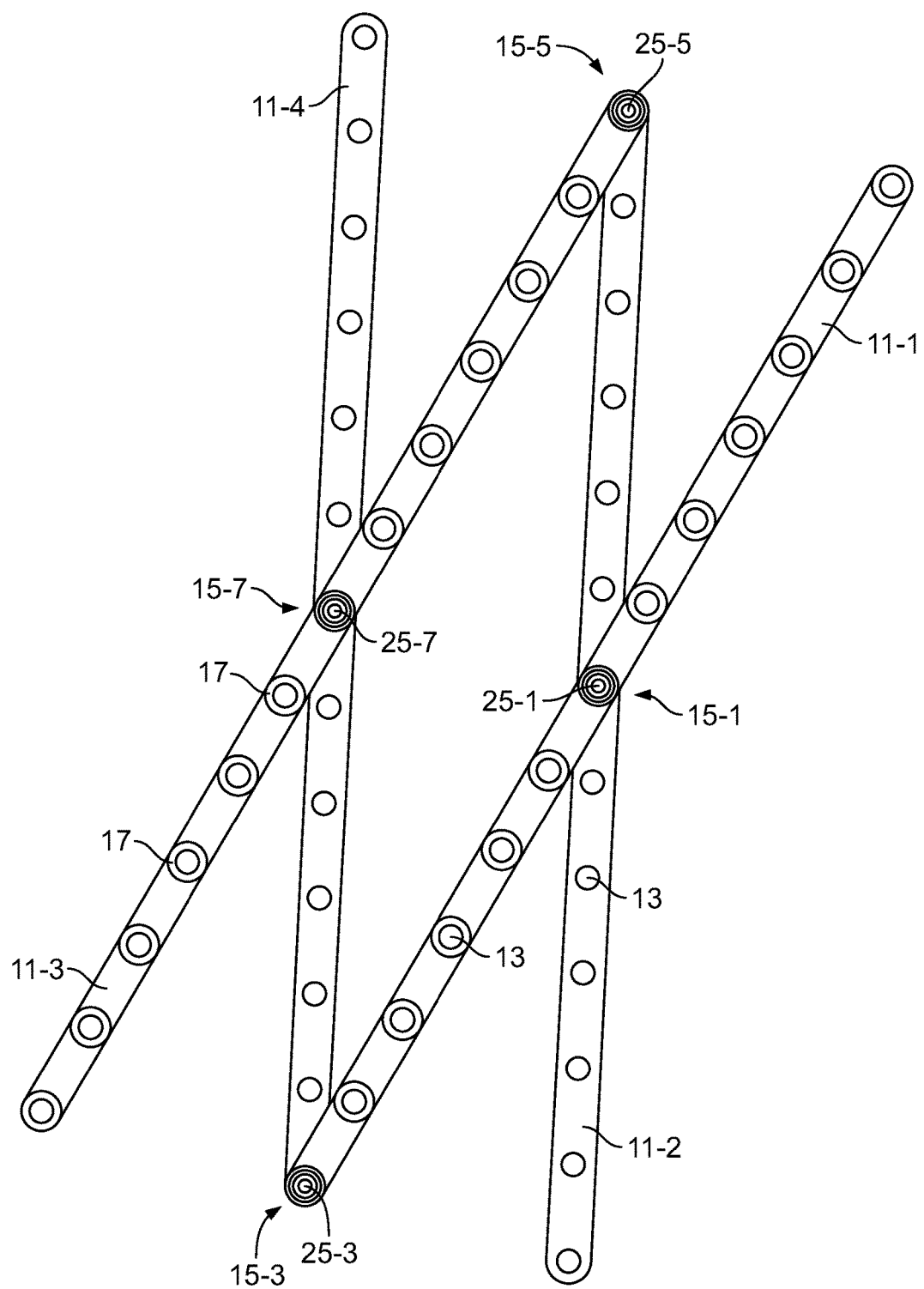
FIG. 1B is a perspective view of a four strut section of the stent of FIG. 1A.
Figure 1D:
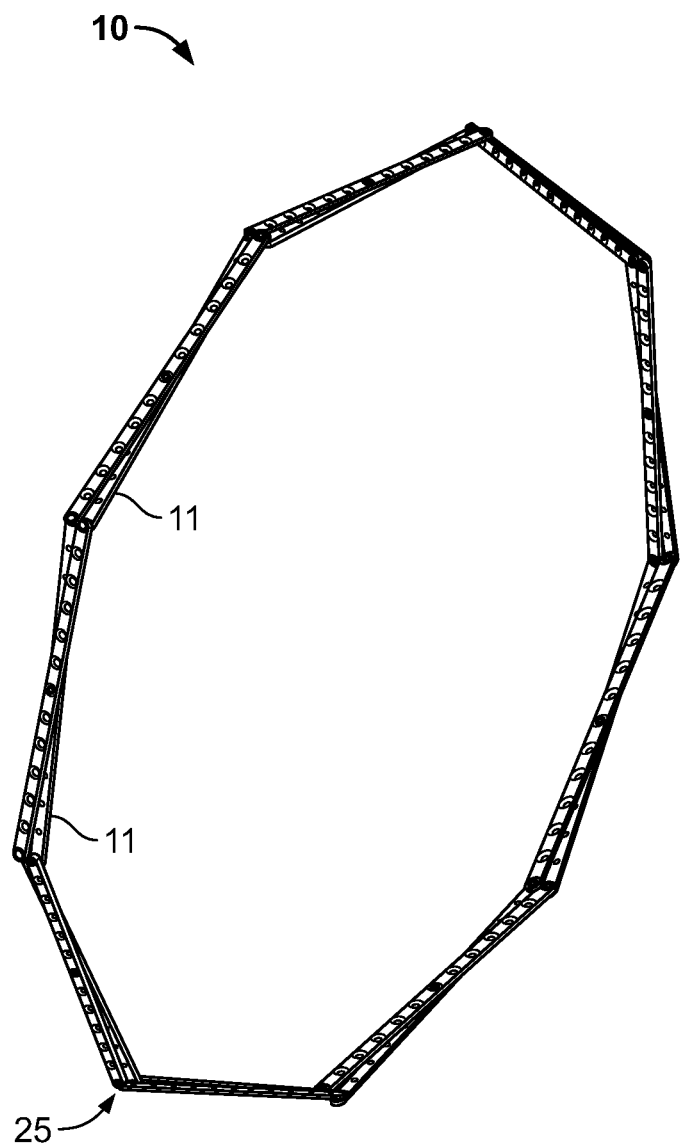

The support structure 10 may have a generally cylindrical shape, with a longitudinal axis 20. The articulated joints may have an axis of rotation perpendicular to the longitudinal axis 20 of the support structure 10. In some variations, the articulated joints may also allow rotation about other axis, while in other variations, the articulated joints may be pin joints allowing rotation about only a single axis perpendicular to the longitudinal axis, as described in more detail above. The support structure 10 may be incrementally and reversibly expandable and collapsible between an expanded configuration, as shown in FIG. 1D, and a compressed or collapsed configuration, as shown in FIG. 1C, as described in more detail above. The strut members 11 may be connected such that the support structure 10 may be moved from the compressed configuration to the expanded configuration, and the reverse, by a number of different force configurations, including radially, longitudinally, and circumferentially directed force, as described in more detail above.

The strut members 11 may have a bar shape and may have a front surface 11f and a back surface 11b. The strut members 11 may be interconnected by fasteners 25, described in more detail above. As described above, each strut member 11 may also include a plurality of orifices 13 spaced along the length of the strut member 11. On the front surface 11f, the orifices may be countersunk 17 to receive the head of a fastener. In a particular embodiment, there are thirteen equally spaced orifices 13 along the length of each strut member 11, but more or fewer orifices can be used.

The strut members 11 can be arranged as a chain of four-bar linkages. FIG. 1B is a perspective view of a four strut section of the stent of FIG. 1A. As shown, two outer strut members 11-1, 11-3 overlap two inner strut members 11-2, 11-4, with their back surfaces in communication with each other. In particular, the first strut member 11-1 may be rotatably connected to the second strut member 11-2 by a middle articulated joint 15-1 using a rivet 25-1, which utilizes orifices 13 that bisect the strut members 11-1, 11-2. Similarly, the third strut member 11-3 may be rotatably connected to bisect the fourth strut member 11-4 by a middle articulated joint 15-7 using a rivet 25-7. It should be understood that the middle articulated joints 15-1, 15-7 can function as a scissor joint in a scissor linkage or mechanism. As shown, the resulting scissor arms are of equal length. It should also be understood that the middle articulated joint 15-1, 15-7 need not bisect the joined strut members, but can instead utilize orifices 13 offset from the longitudinal centers of the strut members resulting in unequal scissor arm lengths.

In addition to the middle scissor articulated joint 15-1, the second strut member 11-2 may be rotatably connected to the third strut member 11-3 by a distal anchor articulated joint 15-5, located near the distal ends of the strut members 11-2, 11-3. Similarly, the first strut member 11-1 may be rotatably connected to the fourth strut member 11-4 by a proximal anchor articulated joint 15-3, located near the proximal ends of the strut members 11-1, 11-4. To reduce stresses on the anchor rivets 25-3, 25-5, the distal and proximal ends of the struts 11 can be curved or twisted to provide a flush interface between the joined struts. As a result of these rotatable connections, the linkage can be reversibly expanded and compressed. When the linkage is laterally compressed, the two strut members 11-4 and 11-2 move to be directly adjacent to each other, and the two strut members 11-3 and 11-1 move to be directly adjacent to each other, such that center diamond-shaped opening is substantially closed. When the linkage is laterally expanded, the center diamond-shaped opening is widened.

As can be seen, the support structure 10 (FIG. 1A) may be fabricated by linking together a serial chain of scissor mechanisms. The chain may then be wrapped to join the last scissor mechanism with the first scissor mechanism in the chain. By actuating the linkage the links can be opened or closed, which results in expanding or compressing the stent 10 (FIG. 1A). FIG. 1C is a perspective view of a compressed support structure of FIG. 1A. When compressed, the stent 10 is at its maximum length and minimum diameter. The maximum length may be limited by the length of the strut members, which in a particular embodiment may be 15 mm. The minimum diameter may be limited by the width of the strut members, which in a particular embodiment may be about 0.052 inch. In compressed as shown in FIG. 1C, the support structure is highly compact. However, the support structure may retain an open lumen through it while in the compressed state.

FIG. 1D is a perspective view of the support structure of FIG. 1A in a fully expanded state. As shown, the fully expanded support structure 10 forms a ring. Once in a fully expanded state, support structure 10 may enter a locked state such that radial inward pressure does not cause the support structure to re-compress and the support structure 10 is in an unstressed state. The ring formed can be used as an annuloplasty ring. In particular, if one end of the stent circumference is attached to tissue, the compression of the stent may enable the tissue to cinch. Because the stent may have the ability to have an incremental and reversible compression or expansion, the device could be used to provide an individualized cinching of the tissue to increase the competency of a heart valve. This could be a useful treatment for mitral valve diseases, such as mitral regurgitation or mitral valve prolapse.

The dimensions of each strut can be chosen in accordance with its desired use (e.g., depending on the implant site). In a particular embodiment, each strut member may be about 0.001-0.100 inch thick. More particularly, each strut can be about 0.01 inch thick. In a particular embodiment, each strut member may be about 0.01-0.25 inches wide and about 0.25-3 inches long. More particularly, each strut can be about 0.06 inches wide and about 0.5 inches long. However, the thickness, width, and length of the struts may be variable, as described below.

The strut members can however be of different geometries. For example, the struts can be non-flat structures. In particular, the struts can include a curvature, such as in a concave or convex manner in relationship to the inner diameter of the stent structure. The struts can also be twisted. The nonflatness or flatness of the struts can be a property of the material from which they are constructed. For example, the struts can exhibit shape-memory or heat-responsive changes in shape to the struts during various states. Such states can be defined by the stent in the compressed or expanded configuration.

While the above-described embodiments have featured a support structure having linear strut bars and equal length scissor arms, other geometries may be employed. The resulting shape may be other than cylindrical and may have different performance characteristics in certain applications.

Figure 2A:
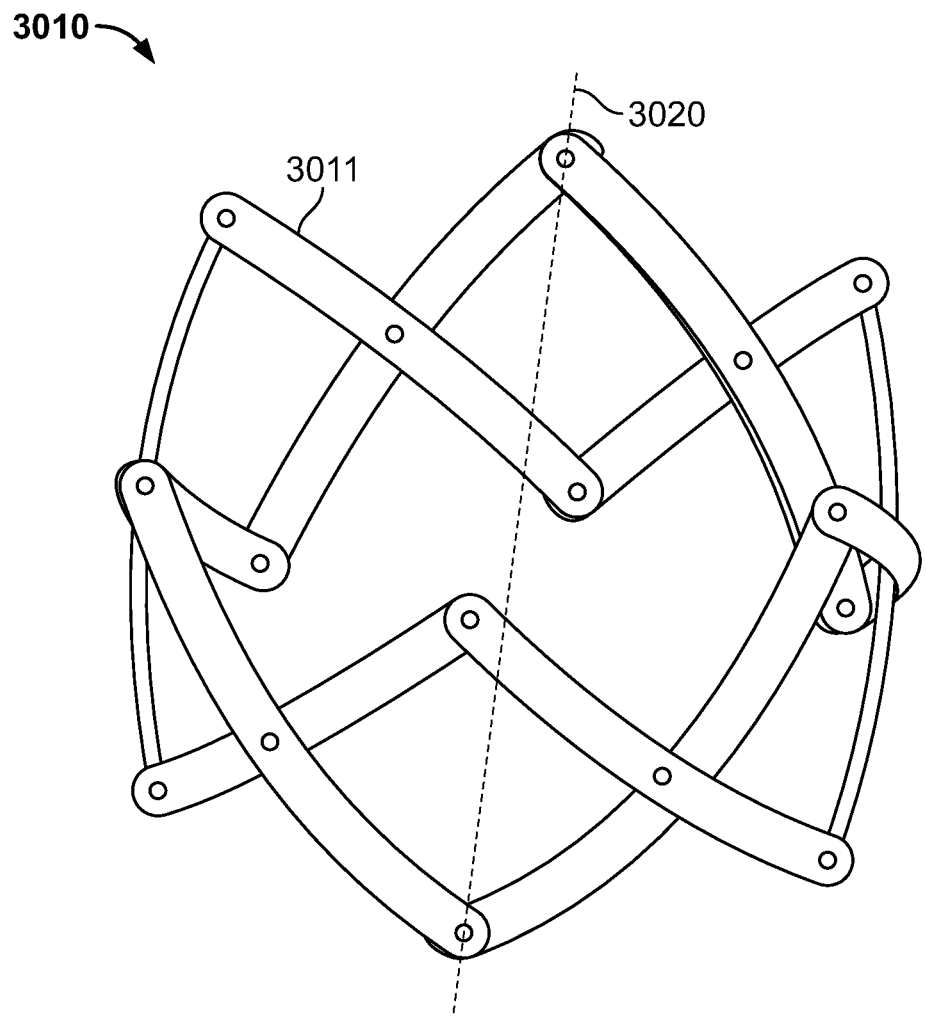
FIGS. 2A-2C illustrate perspective views of variations of a particular endoluminal support structure.

FIG. 1A shows a serial chain of scissor mechanisms such that there are eighteen struts 11, but other numbers of struts 11 can be used, including more than eighteen struts or fewer than eighteen struts. FIG. 2A, for example, shows a support structure 3010 with a serial chain of scissor mechanisms having twelve struts 3011. Like support structure 10, the support structure 3010 may have a generally cylindrical shape, with a longitudinal axis 3020. The articulated joints may have an axis of rotation perpendicular to the longitudinal axis 3020 of the support structure 3010. In some variations, the articulated joints may also allow rotation about other axis, while in other variations, the articulated joints may be pin joints allowing rotation about only a single axis perpendicular to the longitudinal axis, as described in more detail above. The support structure 3010 may be incrementally and reversibly expandable and collapsible between an expanded configuration and a compressed or collapsed configuration, as described in more detail above. The strut members 3011 may be connected such that the support structure 3010 may be moved from the compressed configuration to the expanded configuration, and the reverse, by a number of different force configurations, including radially, longitudinally, and circumferentially directed force, as described in more detail above.

Figure 2B:
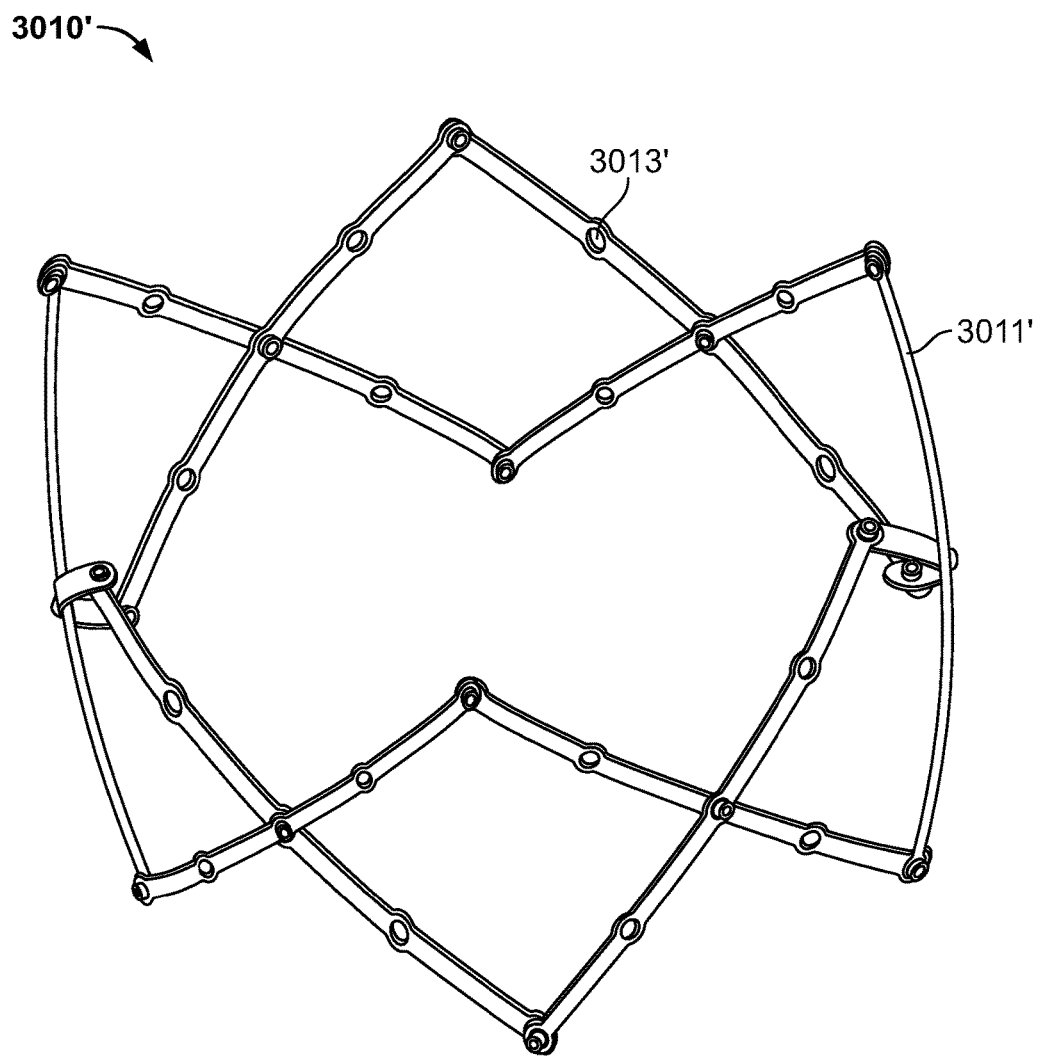
Figure 2C:
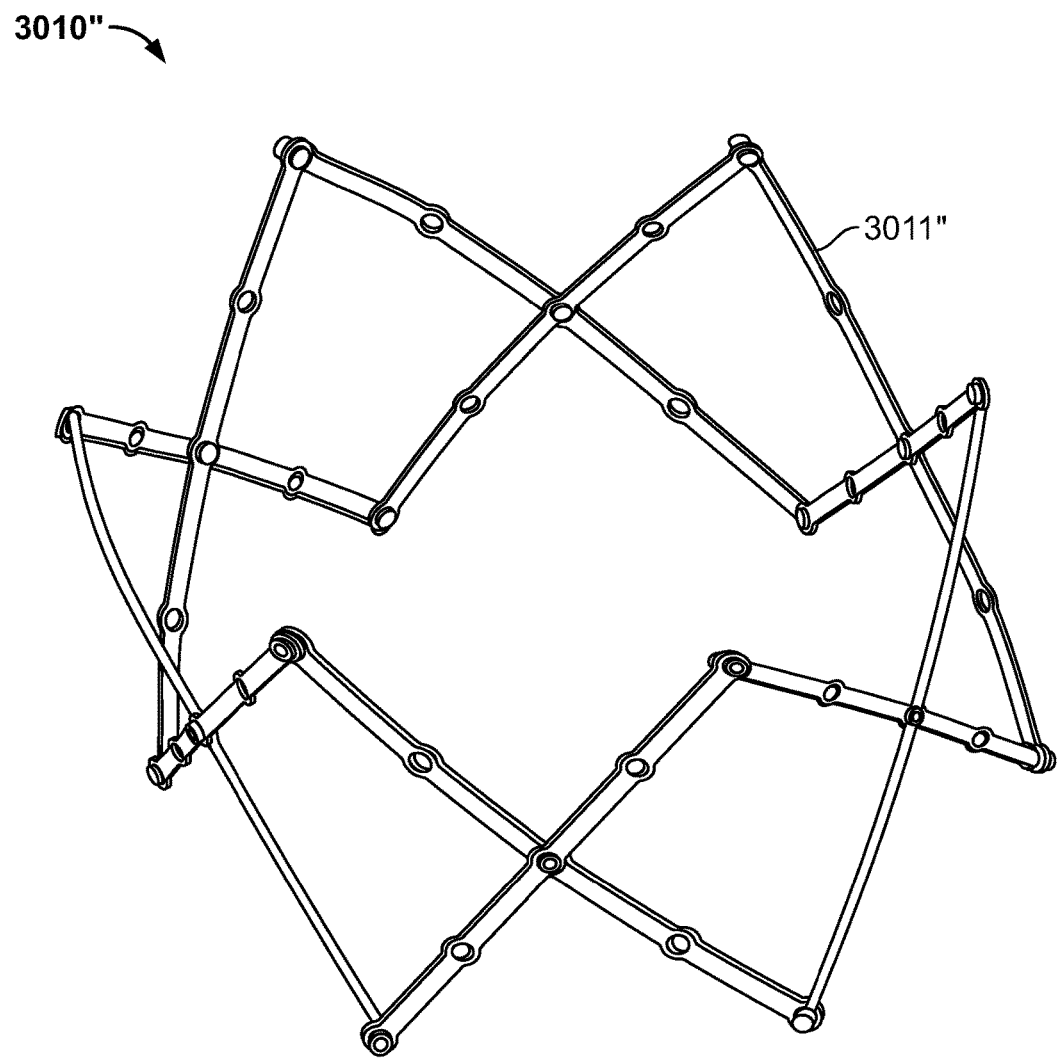

As shown in FIG. 2A, the struts 3011 need not have orifices. In other variations, however, support structures having twelve struts as in FIG. 2A may have orifices 3013, as shown in FIG. 2B. FIGS. 2A-2B also show struts 3011 and 3011', respectively, having an inward curvature. In other variations, such as the variation shown in FIG. 2C, a support structure having twelve struts may have straight struts 3011". Support structures 3010, 3010', and 3010", or support structures having other numbers struts arranged in a similar serial chain of scissor mechanisms, can be reversibly expanded, reversibly compressed, fully expanded to form a ring, implanted, used with an actuator and control catheter assembly, and/or used to support a prosthetic valve in the same manner as support structure 10, described in detail herein.

FIG. 3 is a perspective view of the arrangement of strut members in a conical-shaped support structure configuration. In the conical structure 10', the strut members 11 may be arranged as shown in FIGS. 1A-1D, except that the middle scissor pivots may not bisect the struts. In particular, the middle scissor pivots (e.g. 15'-1, 15'-7) may divide the joined strut members (e.g. 11'-1, 11'-2 and 11'-3, 11'4) into unequal segments of 5/12 and 7/12 lengths. When fully assembled, the resulting support structure may thus conform to a conical shape when expanded. For illustration purposes, the stent 10' is shown with a single-threaded actuator rod 32' (described in more detail below), but it is not a required element for this stent embodiment.

The stent 10' can also assume a cone shape in its expanded configuration by imposing a convex or concave curvature to the individual strut members 11 that comprise the stent 10'. This could be achieved by using a material with memory, such as shape-memory or temperature sensitive Nitinol.

A valve can be orientated in the cone-shaped stent 10' such that the base of the valve was either in the narrower portion of the cone-shaped stent, with the nonbase portion of the valve in the wider portion of the cone. Alternatively, the base of the valve can be located in the widest portion of the stent with the non-base portion of the valve in the less-wide portion of the stent.

The orientation of a cone-shaped stent 10' in the body can be either towards or away from the stream of blood flow. In other body lumens (e.g. respiratory tract or gastrointestinal tract), the stent could be orientated in either direction, in relationship to the axial plane.

Figure 4:
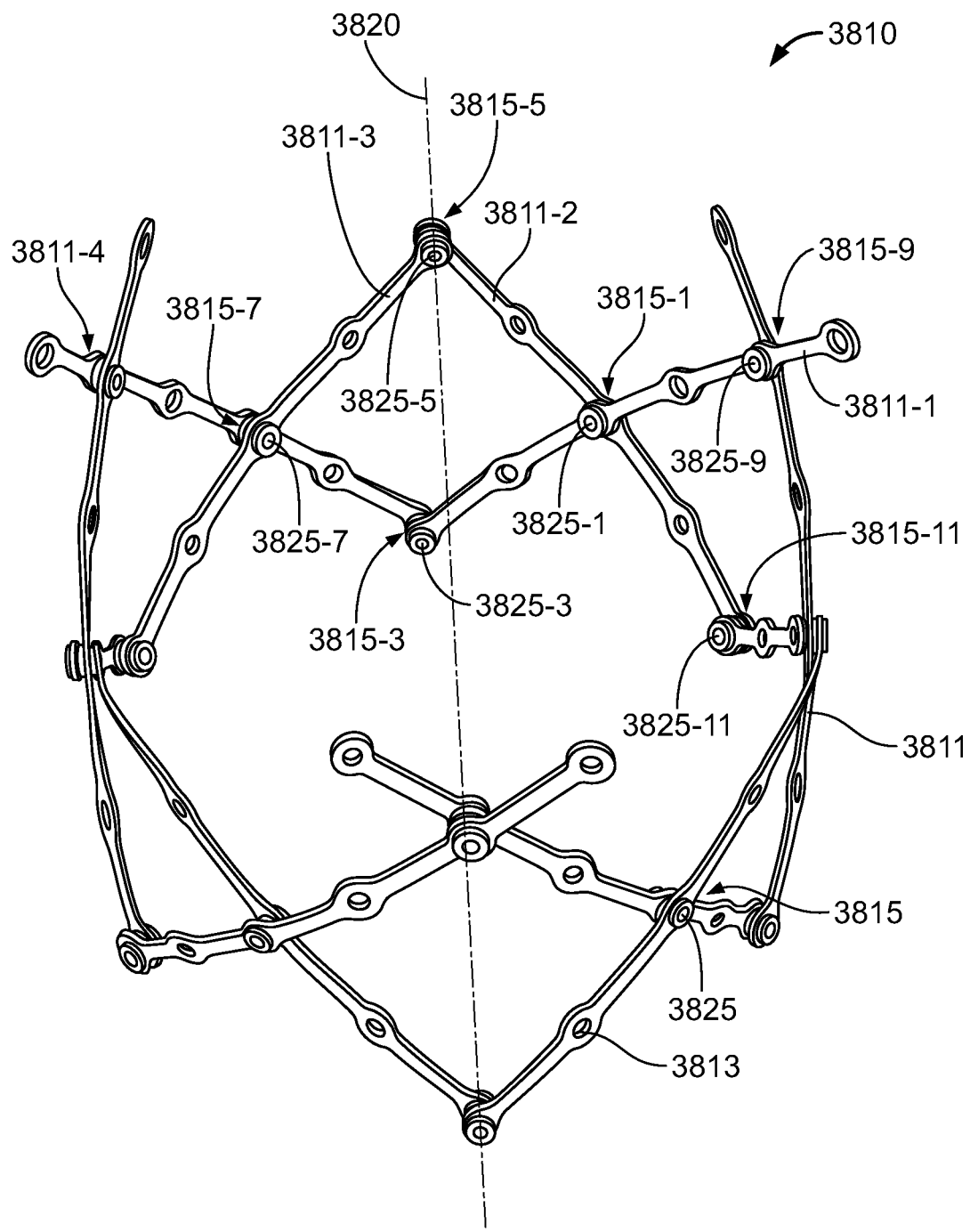
FIG. 4 is a side perspective view of a particular endoluminal support structure.

FIG. 4 shows another example of an endoluminal support structure 3810 with a serial chain of scissor mechanisms having twelve strut members 3811. The support structure 3810 may have a generally cylindrical shape, with a longitudinal axis 3820. The strut members may be interlinked by articulated joints. The articulated joints may have an axis of rotation perpendicular to the longitudinal axis 3820 of the support structure 3810. In some variations, the articulated joints may also allow rotation about other axis, while in other variations, the articulated joints may be pin joints allowing rotation about only a single axis perpendicular to the longitudinal axis, as described in more detail above. The support structure 3810 may be incrementally and reversibly expandable and collapsible between an expanded configuration and a compressed or collapsed configuration, as described in more detail above. The strut members may be connected such that the support structure 3810 may be moved from the compressed configuration to the expanded configuration, and the reverse, by a number of different force configurations, including radially, longitudinally, and circumferentially directed force, as described in more detail above.

Like the stent of FIGS. 1A-1D, the support structure 3810 may comprise a chain of four-bar linkages, each comprising two inner strut members 3811 and two outer strut members 3811 interconnected by fasteners 3825, as described in more detail above. The strut members 3811 may have orifices 3813. In each four-bar linkage, the first strut member 3811-1 (an inner strut member) may be rotatably connected to the second strut member 3811-2 (an outer strut member) by an articulated joint 3815-1 using a rivet 3825-1, which may utilize orifices 3813 located at points spaced apart from the proximal and distal ends of the strut members 3811-1, 3811-2. Similarly, the third strut member 3811-3 (an inner strut member) may be rotatably connected to the fourth strut member 3811-4 (an outer strut member) by an articulated joint 3815-7 using a rivet 3825-7, which may utilize orifices 3813 located at points spaced apart from the proximal and distal ends of the strut members 3811-3, 3811-4. It should be understood that the articulated joints 3815-1, 3815-7 may thus function as a scissor joint in a scissor linkage or mechanism. As shown, the resulting scissor arms are of equal length. It should also be understood that the joints 3815-1, 3815-7 may utilize orifices 3813 offset from the longitudinal centers of the strut members, resulting in unequal scissor arm lengths, or may bisect the joined strut members, resulting in scissor arms of equal lengths.

In addition to the scissor articulated joint 3815-1, the second strut member 3811-2 may be rotatably connected to the third strut member 3811-3 by an articulated joint 3815-5 using rivet 3825-5. Whereas in the four-bar linkages of the stent of FIGS. 1 and 2A-2C, the articulated joint 15-5 is an anchor joint (i.e., it is located near the distal ends of the strut members 11-2, 11-3), the strut members 3811-2, 3811-3 extend distally beyond the articulated joint 3815-5. Strut members 3811-2, 3811-3 may thus be longer than strut members 3811-1, 3811-4. The first strut member 3811-1 may be rotatably connected to the fourth strut member 3811-4 by a proximal anchor articulated joint 3815-3 using rivet 3825-3, located near the proximal ends of the strut members 3811-1, 3811-4. The strut members 3811 may be curved. As a result of these rotatable connections, the linkage can be reversibly expanded and compressed. When the linkage is laterally compressed, the two strut members 3811-2 and 3811-4 move to be closer to each other, and the two strut members 3811-1 and 3811-3 move to be closer to each other, such that center diamond-shaped opening is substantially closed. When the linkage is laterally expanded, the center diamond-shaped opening is widened.

The linkages may be combined into a continuous chain to form a support structure. In the variation of FIG. 4, three linkages may be combined to form support structure 3810. The linkages may be combined by connecting strut member 3811-1 of one linkage with strut member 3811-4 of another linkage at an articulated joint 3815-9 using rivet 3825-9; by connecting strut member 3811-2 of one linkage with strut member 3811-3 of another linkage at articulated joint 3815-11 using rivet 3825-11. Once combined, the continuous chain may be configured such that the expansion or compression of any individual linkage, in the manner described above, may cause the other linkages to also expand or compress. In such a way, the support structure 3810 may be reversibly expanded or compressed by application of force two only two points on the support structure 3810 (e.g., force urging two articulated joints apart or towards each other along a longitudinal axis, or force urging two articulated joints apart or towards each other along the circumference of the support structure).

Figure 5:
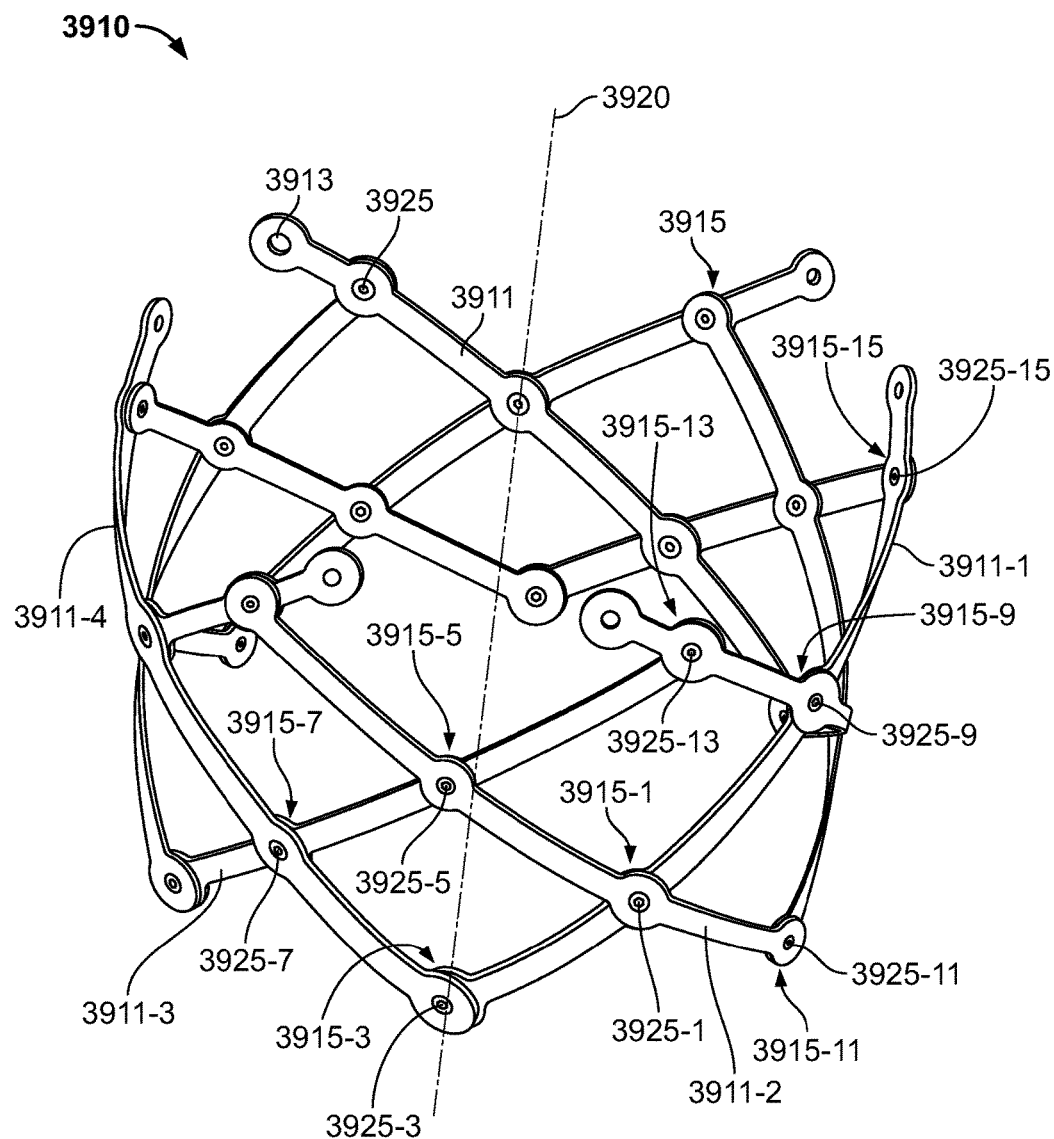
FIG. 5 is a side perspective view of a particular endoluminal support structure with Dacron-sealed struts.

FIG. 5 shows another example of an endoluminal support structure 3910 with a serial chain of scissor mechanisms having twelve struts 3911. The support structure 3910 may have a generally cylindrical shape, with a longitudinal axis 3920. The strut members may be interlinked by articulated joints. The articulated joints may have an axis of rotation perpendicular to the longitudinal axis 3920 of the support structure 3910. In some variations, the articulated joints may also allow rotation about other axis, while in other variations, the articulated joints may be pin joints allowing rotation about only a single axis perpendicular to the longitudinal axis, as described in more detail above. The support structure 3910 may be incrementally and reversibly expandable and collapsible between an expanded configuration and a compressed or collapsed configuration, as described in more detail above. The strut members 3911 may be connected such that the support structure 3910 may be moved from the compressed configuration to the expanded configuration, and the reverse, by a number of different force configurations, including radially, longitudinally, and circumferentially directed force, as described in more detail above.

The support structure 3910 may comprise a chain of four-bar linkages, each comprising strut members 3911 interconnected by articulated joints 3815 using fasteners 3925, as described in more detail above. The strut members may have a coating, described in more detail below. The four-bar linkages may each comprise two outer strut members (3911-2, 3911-4), and two inner strut members (3911-1, 3911-3), where each of the outer strut members may be connected to two inner strut members and no outer strut members, and each of the inner strut members may be connected to two outer strut members and no inner strut members. The four-bar linkages may be combined by connecting each of the outer strut members to two more inner strut members, such that each outer strut member is connected to four inner strut members and no outer strut members, and by connected each of the inner strut members to two more outer strut members, such that each inner strut member is connected to four outer strut members and no inner strut members. It should be appreciated that in other variations, the number of connections may be greater, such that each outer strut member may be connected to greater than four inner strut members, and each inner strut member may be connector to great than four outer strut members. More specifically, the first strut member 3911-1 may be rotatably connected to the second strut member 3911-2 by an articulated joint 3915-1 using a rivet 3925-1, which may utilize orifices 3913 located at points spaced apart from the proximal and distal ends of the strut members 3911-1, 3911-2. Similarly, the third strut member 3911-3 may be rotatably connected to the fourth strut member 3911-4 by an articulated joint 3915-7 using a rivet 3925-7, which may utilize orifices 3913 located at points spaced apart from the proximal and distal ends of the strut members 3911-3, 3911-4. It should be understood that the articulated joints 3915-1, 3915-7 may thus function as a scissor joint in a scissor linkage or mechanism. Similarly, the second strut member 3911-2 may be rotatably connected to the third strut member 3911-3 by an articulated joint 3915-5 using a rivet 3925-5, located at points spaced apart from the proximal and distal ends of the strut members 3911-2, 3911-3, but distal to articulated joints 3915-1 and 3915-7. In addition, the first strut member 3911-1 may be rotatably connected to the fourth strut member 3911-4 by a proximal anchor articulated joint 3915-3 using rivet 3925-3, located near the proximal ends of the strut members 3911-1, 3911-4.

The strut members 3911 may be curved inwardly in a helical fashion. As a result of these rotatable connections, the linkage can be reversibly expanded and compressed. When the linkage is laterally compressed, the two strut members 3911-4 and 3911-2 move to be closer to each other, and the two strut members 3911-3 and 3911-1 move to be closer to each other, such that center diamond-shaped opening is substantially closed. When the linkage is laterally expanded, the center diamond-shaped opening is widened. Unlike the strut members of FIGS. 1A-1D, however, strut members 3911-1 and 3911-4 may be longer than strut members 3911-2, 3911-3, such that when three four-bar linkages are linked to form support structure 3910, the ends of strut members 3911-1, 3911-4 extend beyond the articulated joints linking the four-bar linkages, as shown in FIG. 5.

The linkages may be combined into a continuous chain to form a support structure. In the variation of FIG. 5, three linkages may be combined to form support structure 3910. The linkages may be combined by connecting strut member 3911-1 of one linkage with strut member 3911-4 of another linkage at an articulated joint 3915-9 using rivet 3925-9 at locations spaced away from the distal end of strut members 3911-1 and 3911-4; by connecting strut member 3911-2 of one linkage with strut member 3911-3 of another linkage at articulated joint 3915-11 using rivet 3925-11 at a location at the distal ends of strut members 3911-2 and 3911-3; by connecting strut member 3911-3 of one linkage with strut member 3911-4 of another linkage at an articulated joint 3915-13 using rivet 3925-13 at a location at the distal end of strut member 3911-3 and spaced away from the distal end of strut member 3911-4; and by connecting strut member 3911-1 of one linkage with strut member 3911-2 of another linkage at an articulated joint 3915-15 using rivet 3925-15 at a location at the distal end of strut member 3911-2 and spaced away from the distal end of strut member 3911-1 but distal to articulated joint 3915-9. Once combined, the continuous chain may be configured such that the expansion or compression of any individual linkage, in the manner described above, may cause the other linkages to also expand or compress. In such a way, the support structure 3910 may be reversibly expanded or compressed by application of force two only two points on the support structure 3910 (e.g., force urging two articulated joints apart or towards each other along a longitudinal axis, or force urging two articulated joints apart or towards each other along the circumference of the support structure).

The dimensions of each strut can be chosen in accordance with its desired use (e.g., depending on the implant site). In a particular embodiment, each strut member may be about 0.001-0.100 inches thick. More particularly, each strut may be about 0.01 inches thick. In other variations, some struts may be thinner than other struts, which may provide increased flexibility. In a particular embodiment, each strut may be about 0.01-0.25 inches wide. More particularly, each strut may be about 0.06 inches wide. However, the thickness, width, and length of the struts may be variable, as described below.

As shown, each strut member may be bar shaped. The strut members can however be of different geometries. For example, instead of a uniform width, a strut can vary in width along its length. Furthermore, an individual strut can have a different width than another strut in the same deployment structure. Similarly, the strut lengths can vary from strut to strut within the same deployment structure. The particular dimensions can be chosen based on the implant site. Furthermore, the struts can be non-flat structures. In particular, the struts can include a curvature, such as in a concave, or convex manner in relationship to the inner diameter of the deployment structure. The struts can also be twisted. The nonflatness or flatness of the struts can be a property of the material from which they are constructed. For example, the struts can exhibit shape-memory or heat-responsive changes in shape to the struts during various states. Such states can be defined by the deployment structure in the compressed or expanded configuration.

In other embodiments, articulated support structures may comprise bow struts, as described in PCT/US13/21052, 61/585,165, 61/780,670, which are hereby fully incorporated by reference. In yet other embodiments, articulated support structures may comprise longer struts with more than one middle articulation and end articulations, as described in PCT/US13/21052, 61/585,165, 61/780,670. In yet other embodiments, articulated support structures may comprise radial struts, as described in PCT/US13/21052, 61/585,165, 61/780,670.

It should be noted that any of the above-described support structures may be extended beyond the anchor joints at either of both ends of the stent. By coupling a series of stents in an end-to-end chain fashion, additional stent lengths and geometries can be fabricated. In particular, an hourglass-shaped stent could be achieved by joining two cone-shaped stents at their narrow ends.

Valve Support Structures

Described herein are also valve support structures. These support structures may have similar designs and features to the endoluminal support structures described above, but may comprise commissure strut members configured to have attached valve leaflets. In general, the commissure strut members may extend distally beyond the distal ends of the longitudinal strut members, and may be configured to support valve leaflets in a way that allows the leaflets to form a shape suitable for a prosthetic valve.

Figure 6A:
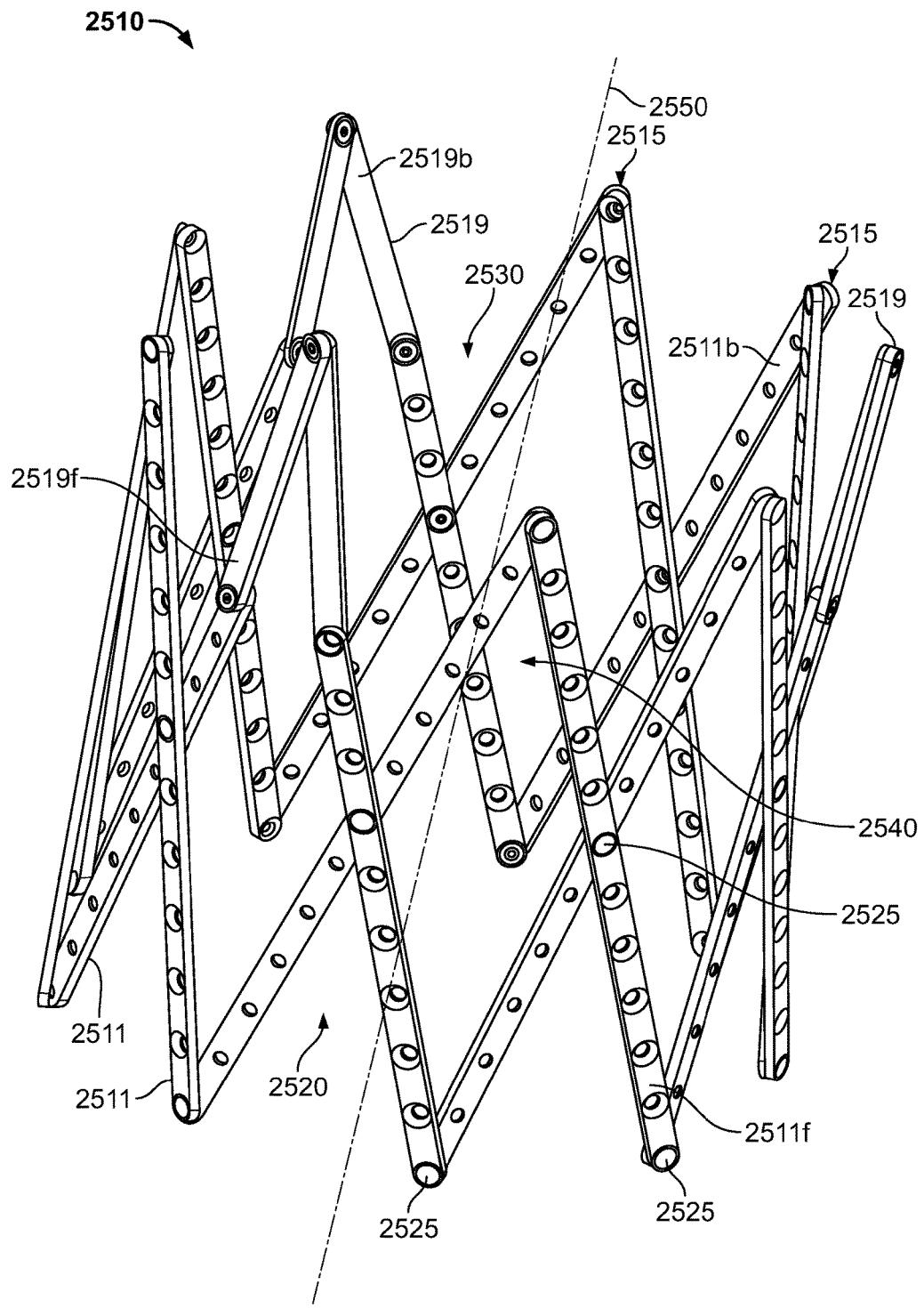
FIG. 6A is a perspective view of a particular endoluminal support structure.

FIG. 6A is a perspective view of a support structure to which a tissue valve may be mounted. The support structure 2510 may have a generally tubular shape comprising a proximal opening 2520, distal opening 2530, and a lumen 2540 therebetween. The tubular shape may be shorter and ring like as in the support structure 2510 in FIG. 6A, or in other variations it may be elongate. The support structure 2510 may have a longitudinal axis 2550 and may comprise a plurality of strut members interlinked by articulated joints. The articulated joints may have an axis of rotation perpendicular to the longitudinal axis 2550 of the support structure 2510. In some variations, the articulated joints may also allow rotation about other axis, while in other variations, the articulated joints may be pin joints allowing rotation about only a single axis perpendicular to the longitudinal axis, as described in more detail above. The support structure 2510 may be incrementally and reversibly expandable and collapsible between an expanded configuration and a compressed or collapsed configuration, as described in more detail above. The strut members may be connected such that the support structure 2510 may be moved from the compressed configuration to the expanded configuration, and the reverse, by a number of different force configurations, including radially, longitudinally, and circumferentially directed force, as described in more detail above.

The support structure 2510 may comprise a plurality of longitudinal strut members 2511 and a plurality of commissure strut members 2519. The longitudinal strut member 2511 and commissure strut members 2519 may be interconnected by a plurality articulations comprising pin or articulated joints 2515. The commissure strut members 2519 and their articulations may permit regions of the support structure to extend further beyond the structure provided by the longitudinal strut members 2511, and which may expand and contract along with the configurational changes to the longitudinal strut members 2511, without generating significantly more resistance or stress in the structure, if any. As shown, there are eighteen struts 2511 and six struts 2519. The articulated joints 2515 may have an axis of rotation with a radial orientation and which may allow the interconnected strut members 2511 and 2519 to rotate relative to each other. One set of articulated joints 2515 connecting longitudinal strut members 2511 may be located at the proximal ends of longitudinal strut members 2511 in a plane aligned with the proximal opening 2520. A second set of articulated joints 2511 connecting longitudinal strut members 2511 may be located at the distal ends of longitudinal strut members 2511 in a plane aligned with the distal opening 2530. A third set of articulated joints 2515 connecting longitudinal strut members 2511 may be located between the proximal opening 2520 and the distal opening 2530. A fourth set of articulated joints 2515 connecting commissure strut members 2519 may be located distal to the plane of distal opening 2530. A fifth set of articulated joints 2515 connecting longitudinal strut members 2511 to commissure strut members 2519 may be located proximal to the plane of distal opening 2530 between the third set of articulated joints 2515 and the plane of distal opening 2530.

The dimensions of each strut can be chosen in accordance with its desired use (e.g., depending on the implant site). In a particular embodiment, each longitudinal strut members may be about 0.001-0.100 inch thick. More particularly, each strut may be about 0.01 inch thick. In a particular embodiment, each longitudinal strut members 2511 may be about 0.01-0.25 inches wide. More particularly, each longitudinal strut members 2511 may be about 0.06 inches wide. However, the thickness, width, and length of the longitudinal strut members 2511 may be variable, as described below. In a particular embodiment, each commissure strut member 2519 may be about 0.001-0.100 inches thick. More particularly, each commissure strut member 2519 may be about 0.01 inches thick. In a particular embodiment, each commissure strut member 2519 may be about 0.01-0.25 inches wide. More particularly, each commissure strut member 2519 may be about 0.06 inches wide. However, the thickness, width, and length of the commissure strut members 2519 may be variable, as described below. Moreover, the thickness and/or material of the commissure strut members 2519 may be such that the commissure strut members 2519 are more flexible than the longitudinal strut members 2511, such as by being thinner or by being made of a more flexible material.

As shown, each longitudinal strut member 2511 is bar shaped and has a front surface 2511f and a back surface 2511b; and each commissure strut member 2519 is bar shaped and has a front surface 2519f and a back surface 2519b. The strut members can, however, optionally comprise different geometries. For instance, the longitudinal struts 2511 and commissure struts 2519 can be non-flat structures. In particular, the struts can include a curvature, such as in a concave or convex manner in relationship to the inner diameter of the support structure 2510. The struts can also be twisted. The nonflatness or flatness of the struts can be a property of the material from which they are constructed. For example the struts can exhibit shape-memory or heat responsive changes in shape to the struts during various states. Such states can be defined by the support structure in the compressed or expanded configuration. The struts can also exhibit changes in shape due to stressed on them while implanted. For instance, if used to support a prosthetic valve assembly as described in detail below, the stress on the commissure struts 2519 during the normal cardiac cycle may cause the commissure struts 2519 to permanently or temporarily bend or otherwise change shape. In variations in which the commissure strut members 2519 are fabricated from biocompatible materials having greater flexibility than the materials from which the longitudinal strut members 2511 are fabricated, if a force including a radially inward component is applied to the commissure strut members, they may flex inward, while the longitudinal strut members 2511 may not substantially deform.

Each longitudinal strut member 2511 may also include a plurality of orifices 2513 spaced along the length of strut members 2511, as described above. On the front surface 2511f, orifices may be countersunk to receive the head of a fastener. FIG. 6A shows commissure strut members 2519 as not having orifices 2513 along their lengths. However, in other instances, the commissure strut members 2519 may have orifices 2513 along their lengths. Orifices 2513 on commissure strut members 2519 can similarly be countersunk on front surface 2519f to receive the head of a fastener. In the support structure of FIG. 6A, longitudinal strut members 2511-1 and 2511-4 (FIG. 6B) may have thirteen orifices 2513 and longitudinal strut members 2511-2 and 2511-3 (FIG. 6B) may have ten orifices 2513. There can, however, be more or fewer orifices on longitudinal strut members 2511.

Figure 6B:
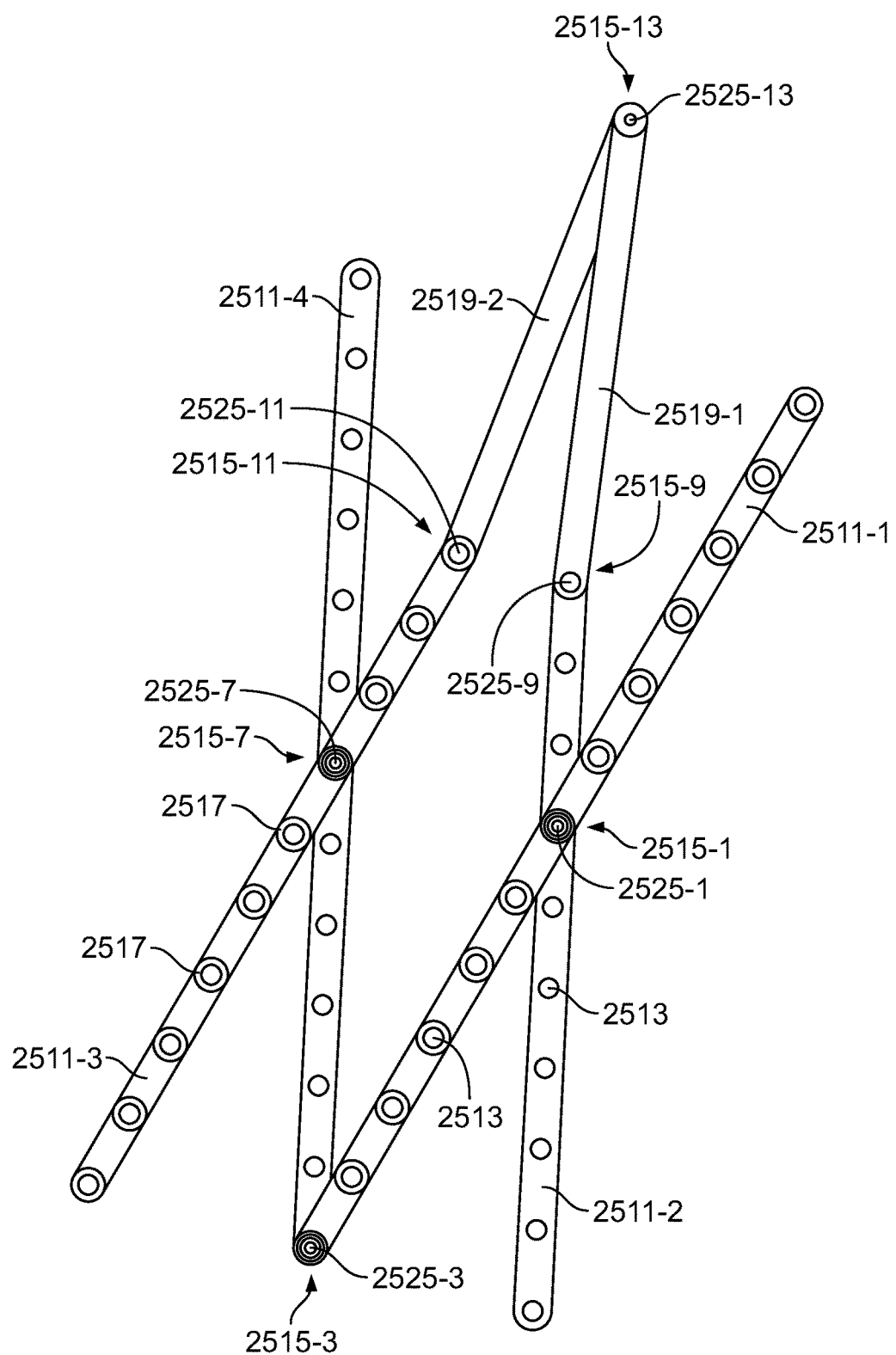
FIG. 6B is a perspective view of a six strut section of the structure of FIG. 6A.

The strut members 2511 and 2519 may be arranged as a chain of four- and six-bar linkages, and wherein at least some, if not all, of the linkage sets share common struts with adjacent linkages and configuration changes to one linkage will generate complementary changes to the other linkages linked by common struts. Complementary changes, however, are not necessarily limited to linkages or struts with common struts. The four-bar linkages may have the same configuration as the four strut section of the stent of FIG. 1B, described in detail above. FIG. 6B is a perspective view of a six-bar linkage of the support structure of FIG. 10A. As shown, two outer strut members 2511-1, 2511-3 overlap two inner strut members 2511-2, 2511-4, with their back surfaces in communication with each other. In addition, two commissure strut members—outer commissure strut member 2519-1 and inner commissure strut member 2519-2—can be connected to inner strut member 2511-2 and outer strut member 2511-3. The strut members 2511, 2519 may be interconnected by fasteners 2525, as described above, extending through aligned orifices.

In particular, the outer strut member 2511-1 may be rotatably or swivelably connected to the inner strut member 2511-2 by an articulated joint 2515-1 using a rivet 2525-1, which utilizes orifices 2913. The articulated joint 2515-1 may bisect outer strut member 2511-1. The articulated joint 2515-1 may not bisect inner strut member 2511-2, but instead utilize an orifice 2513 that is offset distally from the longitudinal center of inner strut member 2511-2. It should be understood that the articulated joint 2515-1 may utilize different orifices 2513 than the ones shown in FIG. 6B.

The outer strut member 2511-3 may be rotatably connected to the inner strut member 2511-4 by an articulated joint 2515-7 using a rivet 2525-7, which utilizes orifices 13. The articulated joint 2515-7 may bisect inner strut member 2511-4. The articulated joint 2525-7 may not bisect outer strut member 2511-3, but instead utilize an orifice 2513 that is offset distally from the longitudinal center on outer strut member 2511-3. It should be understood that the articulated joint 2515-7 may utilize different orifices 2513 than the ones shown in FIG. 6B.

In addition to the articulated joint 2515-1, the outer strut member 2511-1 may be rotatably connected to the inner strut member 2511-4 by a proximal anchor articulated joint 2515-3 using rivet 2525-3, located near the proximal ends of the strut members 2511-1, 2511-4. The inner strut member 2511-2 may also be rotatably connected to the commissure strut member 2519-1 by an articulated joint 2515-9 using a rivet 2525-9, located near the distal end of inner strut member 2511-2 and the proximal end of commissure strut member 2519-1. Likewise, the outer strut member 2511-3 may be rotatably connected to the commissure strut member 2519-2 by an articulated joint 2515-11 using a rivet 2525-11, located near the distal end of outer strut member 2511-3 and the proximal end of commissure strut member 2519-2. Commissure strut member 2519-1 may also be rotatably connected to commissure strut member 2519-2 by a distal anchor articulated joint 2515-13 using rivet 2525-13, located near the distal ends of the commissure strut members 2519-1, 2519-2.

To reduce stress on the anchor rivets 2525-3, 2525-13, the proximal ends of struts 2511-1, 2511-4 and distal ends of commissure struts 2519-1, 2519-2 may be curved or twisted to provide a flush interface between the joined struts.

As can be seen in FIG. 6A, the support structure 2510 may be fabricated by linking together a chain of individual six-strut sections (FIG. 6B) and four-strut sections (FIG. 1B). The chain may then be wrapped or otherwise connected back to itself to join the last section with the first section in the chain. As shown in FIG. 6A, a chain of three six-strut sections and six four-strut sections may be joined, such that every third section is a six-strut section. It should be understood that different numbers of four-strut sections may be linked with the three six-strut sections. In some variations, the support structure may have zero four-strut sections and consist only of six-strut sections. As in the support structure 10 shown in FIG. 1A, actuating the linkage may cause the links to be opened or closed, which may result in expanding or compressing the support structure 2510 (FIG. 6A). When the support structure is in neither a fully expanded nor fully compressed state, the angle between commissure strut members 2519-1, 2519-2 at distal anchor articulated joint 2515-13 may be less than the angle between two longitudinal strut members 2511 at an anchor articulated joint 2515 located near the distal ends of the two longitudinal strut members 2511.

Strut members 2511, 2519 may have lengths chosen based on the implant site. In a particular embodiment, outer longitudinal strut 2511-1 and inner longitudinal strut 2511-4 may have approximately the same length, inner longitudinal strut 2511-2 and outer longitudinal strut 2511-3 may have approximately the same length, and commissure struts 2519-1, 2519-2 may have approximately the same length. In that embodiment the length of outer longitudinal strut 2511-1 and inner longitudinal strut 2511-4 may be greater than the length of inner longitudinal strut 2511-2 and outer longitudinal strut 2511-3. In that embodiment, the combined longitudinal length of longitudinal strut member 2511-2 and commissure strut member 2519-1 may be greater than the length of longitudinal strut member 2511-1 or longitudinal strut member 2511-4. In that embodiment, the combined longitudinal length of longitudinal strut member 2511-3 and commissure strut member 2519-2 may be greater than the length of longitudinal strut member 2511-1 or longitudinal strut member 2511-4. In some embodiments the combined length of longitudinal strut member 2511-2 and commissure strut member 2519-1 may be at least 20% longer than the length of longitudinal strut members 2511-1 or 2511-4. Similarly the combined longitudinal length of longitudinal strut member 2511-3 and commissure strut member 2519-2 may be at least 20% longer than the length of longitudinal strut members 2511-1 or 2511-4. Distal anchor articulated joint 2515-13, located near the distal ends of commissure strut members 2519-1 and 2519-2 may extend beyond the plane of the distal opening 2530 by a longitudinal distance that is at least 20% of the longitudinal distance between the planes of the proximal opening 2520 and distal opening 2530. In one embodiment outer longitudinal strut 2511-1 and inner longitudinal strut 2511-4 may be about 0.250-3.00 inches long; inner longitudinal strut 2511-2 and outer longitudinal strut 2511-3 may be about 0.1-2.5 inches long; and commissure struts 2519-1, 2519-2 may be about 0.1-2.5 inches long. More particularly, outer longitudinal strut 2511-1 and inner longitudinal strut 2511-4 may be about 0.5 inches long; inner longitudinal strut 2511-2 and outer longitudinal strut 2511-3 may be about 0.375 inches long; and commissure struts 2519-1, 2519-2 may be about 0.2 inches long.

The diameter of support structure 2510 can be chosen based on the implant site. In a particular embodiment for implantation at the mitral valve opening, the diameter may be about 0.5-1.55 inches. More particularly, the diameter may be about 0.8 inches.

Figure 7A:
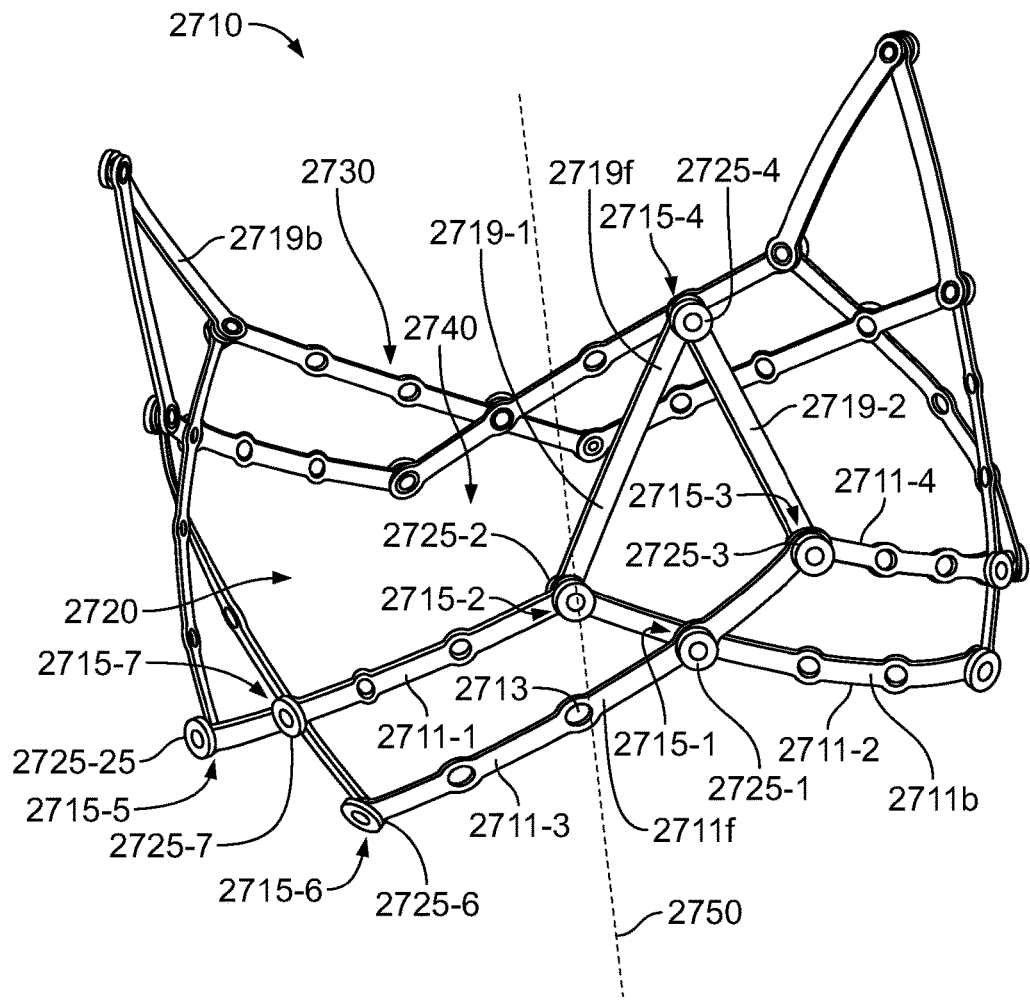
FIG. 7A is a perspective view of another embodiment of an endoluminal support structure.

FIG. 7A is a perspective view of another articulated support structure to which a tissue valve may be able to be mounted. The support structure may have a tubular shape having a proximal opening 2720, distal opening 2730, and a lumen 2740 therebetween. The tubular shape may be shorter and ring like as in the support structure 2710 in FIG. 7A, or in other variations it may be elongate. The support structure 2710 may have a longitudinal axis 2750 and may comprise a plurality of strut members interlinked by articulated joints. The articulated joints may have an axis of rotation perpendicular to the longitudinal axis 2750 of the support structure 2710. In some variations, the articulated joints may also allow rotation about other axis, while in other variations, the articulated joints may be pin joints allowing rotation about only a single axis perpendicular to the longitudinal axis, as described in more detail above. The support structure 2710 may be incrementally and reversibly expandable and collapsible between an expanded configuration and a compressed or collapsed configuration, as described in more detail above. The strut members may be connected such that the support structure 2710 may be moved from the compressed configuration to the expanded configuration, and the reverse, by a number of different force configurations, including radially, longitudinally, and circumferentially directed force, as described in more detail above.

Like the support structure of FIG. 6A, support structure 2710 may include a plurality of longitudinal strut members 2711 and commissure strut members 2719 interconnected by a plurality of articulated joints 2715. As shown, there are twelve struts 2711 and six struts 2719. The articulated joints 2715 may have an axis of rotation with radial orientation, which may allow the interconnected strut members 2711 and 2719 to rotate relative to each other. One set of articulated joints 2715 connecting longitudinal strut members 2711 may be located at the proximal ends of strut members 2711 in a plane aligned with proximal opening 2720. A second set of articulated joints 2711 connecting longitudinal strut members 2711 to each other and to commissure strut members 2719 may be located at the distal ends of longitudinal strut members 2711 and the proximal ends of commissure strut members 2719 and in a plane aligned with the distal opening 2730. A third set of articulated joints 2711 connecting longitudinal strut members 2711 may be located between the proximal opening 2720 and distal opening 2730 and proximal to the midpoint between the proximal opening 2720 and distal opening 2730. A fourth set of articulated joints 2711 may be located between the proximal opening 2720 and distal opening 2730 and distal to the midpoint between the proximal opening 2720 and distal opening 2730. A fifth set of articulated joints 2711 connecting commissure strut members 2719 may be located distal to the plane of distal opening 2730.

The dimensions of each strut can be chosen in accordance with its desired use (e.g., depending on the implant site). In a particular embodiment, each longitudinal strut member 2711 may be about 0.001-0.100 inches thick. More particularly, each longitudinal strut member 2711 may be about 0.01 inches thick. In a particular embodiment, each longitudinal strut member 2711 may be about 0.01-0.25 inches wide. More particularly, each longitudinal strut member 2711 may be about 0.06 inches wide. In a particular embodiment, each commissure strut member 3719 may be about 0.001-0.100 inch thick. More particularly, each commissure strut member 3719 may be about 0.01 inches thick. In a particular embodiment, each commissure strut member 2719 may be about 0.010-0.250 inches wide. More particularly, each commissure strut member 2719 may be about 0.06 inches wide. However, the thickness, width, and length of the commissure strut members 2719 may be variable, as described below. Moreover, the thickness and/or material of the commissure strut members 2719 may be such that the commissure strut members 2719 are more flexible than the longitudinal strut members 2711, such as by being thinner or by being made of a more flexible material.

As shown, each longitudinal strut member 2711 is bar shaped and has a front surface 2711f and a back surface 2711b; and each commissure strut member 2719 is bar shaped and has a front surface 2719f and a back surface 2719b. The strut members may, however, be of different geometries. For instance, the longitudinal struts 2711 and commissure struts 2719 can be non-flat structures. In particular, the struts can include a curvature, such as in a concave or convex manner in relationship to the inner diameter of the support structure 2710. The struts can also be twisted. The nonflatness or flatness of the struts can be a property of the material from which they are constructed. For example the struts can exhibit shape-memory or heat responsive changes in shape to the struts during various states. Such states can be defined by the support structure in the compressed or expanded configuration. The struts can also exhibit changes in shape due to stressed on them while implanted. For instance, if used to support a prosthetic valve assembly as described in detail below, the stress on the commissure struts 2719 during the normal cardiac cycle may cause the commissure struts 2719 to permanently or temporarily bend or otherwise change shape. In variations in which the commissure strut members 2719 are fabricated from biocompatible materials having greater flexibility than the materials from which the longitudinal strut members 2711 are fabricated, if a force including a radially inward component is applied to the commissure strut members 2719, they may flex inward, while the longitudinal strut members 2711 may not substantially deform.

Figure 7B:
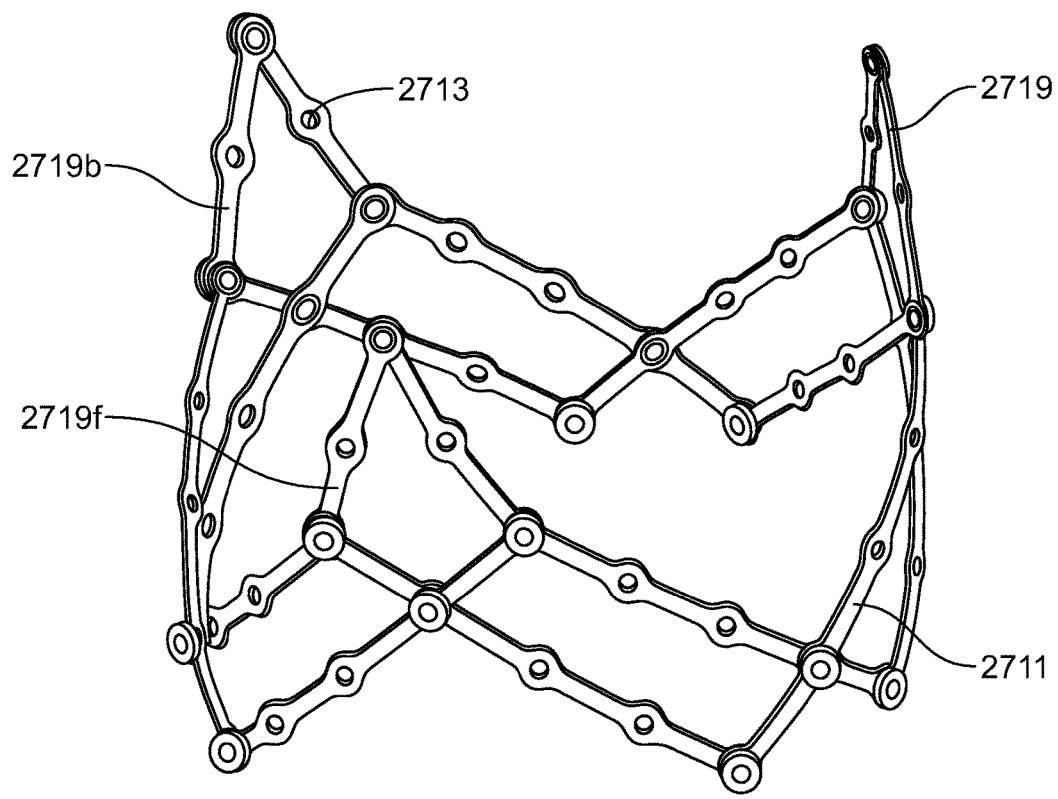
FIG. 7B is a perspective view of a variation of the structure of FIG. 7A.

Each longitudinal strut member 2711 may also include a plurality of orifices 2713 spaced along the length of strut members 2711, as described above. On the front surface 2711f, orifices may be countersunk to receive the head of a fastener. FIG. 7A shows commissure strut members 2719 as not having orifices 2713 along their lengths. However, in other instances the commissure strut members 2719 may have orifices 2713 along their lengths, as shown in the variation in FIG. 7B. Orifices 2713 on commissure strut members 2719 may similarly be countersunk on front surface 2719f to receive the head of a fastener. In FIG. 7A, longitudinal strut members 2711 have five orifices 2713. There can, however, be more or fewer orifices on longitudinal strut members 2711. For example, in another embodiment, longitudinal struts 2711-2, 2711-3 may have four orifices 2713, and longitudinal struts 2711-1, 2711-4 may have no orifices. In another embodiment, longitudinal struts 2711-2, 2711-3 may have no orifices, and longitudinal struts 2711-1, 2711-4 may have four orifices 2713.

The strut members 2711 and 2719 may be arranged as a chain of three six-strut elements. Each six-strut element may contain two outer strut members 2711-1, 2711-3, which overlap two inner strut members 2711-2, 2711-4, with their back surfaces in communication with each other. In addition, each inner and outer strut member may be connected to one of two commissure strut members—outer commissure strut member 2719-1 or inner commissure strut member 2719-2. The strut members 2711, 2719 may be interconnected by fasteners 2725, as described in more detail above, extending through aligned orifices.

In particular, the outer strut member 2711-1 may be rotatably connected to the inner strut member 2711-2 by a distal articulated joint 2715-2 using rivet 2725-2, located near the distal ends of the strut members 2711-1, 2711-2. The outer strut member 2711-3 may be rotatably connected to the inner strut member 2711-4 by a distal articulated joint 2715-3 using rivet 2725-3, located near the distal ends of the strut members 2711-3, 2711-4. The outer strut member 2711-3 may also be rotatably connected to the inner strut member 2711-2 by an articulated joint 2715-1 using a rivet 2725-1, which utilizes orifices 2713. The articulated joint may be offset distally from the longitudinal center on both outer strut member 2711-3 and inner strut member 2711-2. It should be understood that the articulated joint 2715-1 may utilize different orifices 2713 than the ones shown in FIG. 7A, including being offset proximally from the longitudinal center.

The commissure strut member 2719-1 may be rotatably connected at its proximal end to outer strut member 2711-1 and inner strut member 2711-2 at articulated joint 2715-2 using rivet 2725-2. The commissure strut member 2719-2 may be rotatably connected at its proximal end to outer strut member 2711-3 and inner strut member 2711-4 at articulated joint 2715-3 using rivet 2725-3.

Commissure strut member 2719-1 may be rotatably connected to commissure strut member 2719-2 by a distal anchor articulated joint 2715-4 using rivet 2725-4, located near the distal ends of the commissure strut members 2719-1, 2719-2.

As can be seen, the support structure 2710 may be fabricated by linking together a chain of three six-strut elements, and wherein at least some, if not all, of the linkage sets share common struts with adjacent linkages and configuration changes to one linkage will generate complementary changes to the other linkages linked by common struts. Complementary changes, however, are not necessarily limited to linkages or struts with common struts. Two such elements may be connected by rotatably connecting the outer strut member 2711-1 of a first element to the inner strut member 2711-2 of a second element by a proximal anchor articulated joint 2715-5 using rivet 2725-5, located near the proximal ends of strut member 2711-1 of the first element and strut member 2711-2 of a second element. In addition, the outer strut member 2711-3 of the first element may be rotatably connected to the inner strut member 2711-4 of the second element by a proximal anchor articulated joint 2715-6 using rivet 2725-6, located near the proximal ends of strut member 2711-3 of the first element and strut member 2711-4 of the second element. Outer strut member 2711-1 of the first element may also be rotatably connected to inner strut member 2711-4 of the second element by an articulated joint 2715-7 using rivet 2725-7, which utilizes orifices 2713. The articulated joint may be offset proximally from the longitudinal center on both the outer strut member 2711-1 and inner strut member 2711-4. It should be understood that articulated joint 2715-7 may utilize different orifices 2713 than the ones shown in FIG. 7A, including being offset distally from the longitudinal center. A third element may be connected to the second element in the same manner as the second element is connected to the first element. The chain may then be wrapped to join the third element with the first element in the same manner.

When the support structure 2710 is in neither a fully expanded nor fully compressed state, the angles between the commissure strut members 2719-1, 2719-2 at distal anchor articulated joint 2715-4 may be less than the angle between two longitudinal strut members 2711 at other anchor articulated joints 2715-2, 2715-3, 2715-5, and 2715-6. In the embodiment in FIG. 7A the angles between two longitudinal strut members 2711 at anchor articulated joints 2715-2, 2715-3, 2715-5, and 2715-6 are the same. In other embodiments the angles may be different.

Strut members 2711, 2719 may have lengths chosen based on the implant site. In a particular embodiment, longitudinal strut members 2711 may all have approximately the same length, and commissure strut members 2719 may all have approximately the same length. In the variation shown in FIG. 7A, the commissure strut members 2719 have a shorter length than longitudinal strut members 2719. In other variations, the commissure strut members 2719 may be longer than longitudinal strut members 2719. In one embodiment longitudinal strut members 2711 may be about 0.25-3 inches long, and commissure strut members 2719 may be about 0.25-2 inches long. More particularly, longitudinal strut members 2711 may be about 1.75 inches long, and commissure strut members 2719 may be about 1 inch long.

To reduce stress on the anchor rivets 2725-4, 2725-5, and 2725-6, the proximal ends of longitudinal strut members 2711 and distal ends of commissure strut members 2719 can be curved or twisted to provide a flush interface between the joined struts.

The diameter of support structure 2710 can be chosen based on the implant site. In a particular embodiment for implantation at the mitral valve opening, the diameter may be about 0.5-1.5 inches. More particularly, the diameter may be about 0.8 inches. In another embodiment for implantation at the aortic valve opening, the diameter may be larger than the diameter of an embodiment for implantation at the mitral valve opening. More particularly, the diameter may be about 0.5-2.0 inches. In a particular embodiment, the diameter may be about 1 inch. The diameter may be such that the valve is secured in the aortic valve opening by exerting a strong outward radial force against the tissue, forming a friction fit.

In an embodiment at the aortic valve opening, the overall height of the valve support structure may be less than the overall height of an embodiment for implantation at the mitral valve. In an embodiment the height in the expanded configuration may be about 0.2-2.0 inches. More particularly, the height in the expanded configuration may be about 0.6 inches.

Actuators

The support structures described herein may have their diameters compressed by utilizing the articulated joints for insertion through a biological lumen, such as an artery, to a selected position. The support structure can then be expanded to secure the support structure at the selected location. Furthermore, after being expanded, the selected structure can be recompressed for removal from the body or for repositioning. Due to the properties of a scissor linkage wrapped into a cylinder, actuators can exert force to expand the stent diameter by either increasing the distance between neighboring scissor joints, and decreasing the distance between the anchor joints.

The actuators may be attached to the support structures in any suitable manner for reversibly moving the support structures between compressed and expanded configurations. In some variations, the actuator may be attached so as to apply longitudinally oriented forces urging two strut members longitudinally away or towards each other. In order to do so, the actuator may be attached to two longitudinally adjacent articulated joints; that is, the actuator is attached at two articulated joints located along the same longitudinal axis of the support structure. In other variations, the actuator may be attached at points along the strut members not at the location of articulated joints. It should be appreciated that the actuator may be configured to apply longitudinally oriented forces urging two strut members longitudinally away or towards each other while being attached at an angle to the longitudinal axis. In some variations, the actuator may be attached so as to apply circumferentially oriented forces urging two strut members circumferentially away or towards each other. In order to do so, the actuator may be attached to two circumferentially adjacent joints (e.g., at scissor joints between strut members). In other variations, the actuator may be attached at points along the strut members not at the location of articulated joints. It should be appreciated that the actuator may be configured to apply circumferentially oriented forces urging two strut members circumferentially away or towards each other while being attached at an angle to a circumferential plane through the support structure (e.g. at an angle to a plane orthogonal to the longitudinal axis of the support structure). In some variations, the actuator may be attached so as to apply radially oriented forces urging two or more points on the support structure away or towards each other. It should also be appreciated that in some variations, the actuator may comprise more than two ends, and may be attached to the support structure at more than two points. It should be appreciated that the actuator may be attached to the outside of the support structure, the inside of the support structure, or it may be attached in the same plane as the strut members.

While the support structures described herein may be able to be implanted in a patient during an open operative procedure, a closed procedure may also be desirable. As such, the support structures may include an actuator to allow a surgeon to expand or compress the support structure from a location remote from the implant site. In a typical procedure, the support structures may be implanted through a body lumen, such as the femoral artery, using a tethered endoluminal catheter. As such, the actuators may be able to be controlled via a catheter.

Figure 8A:
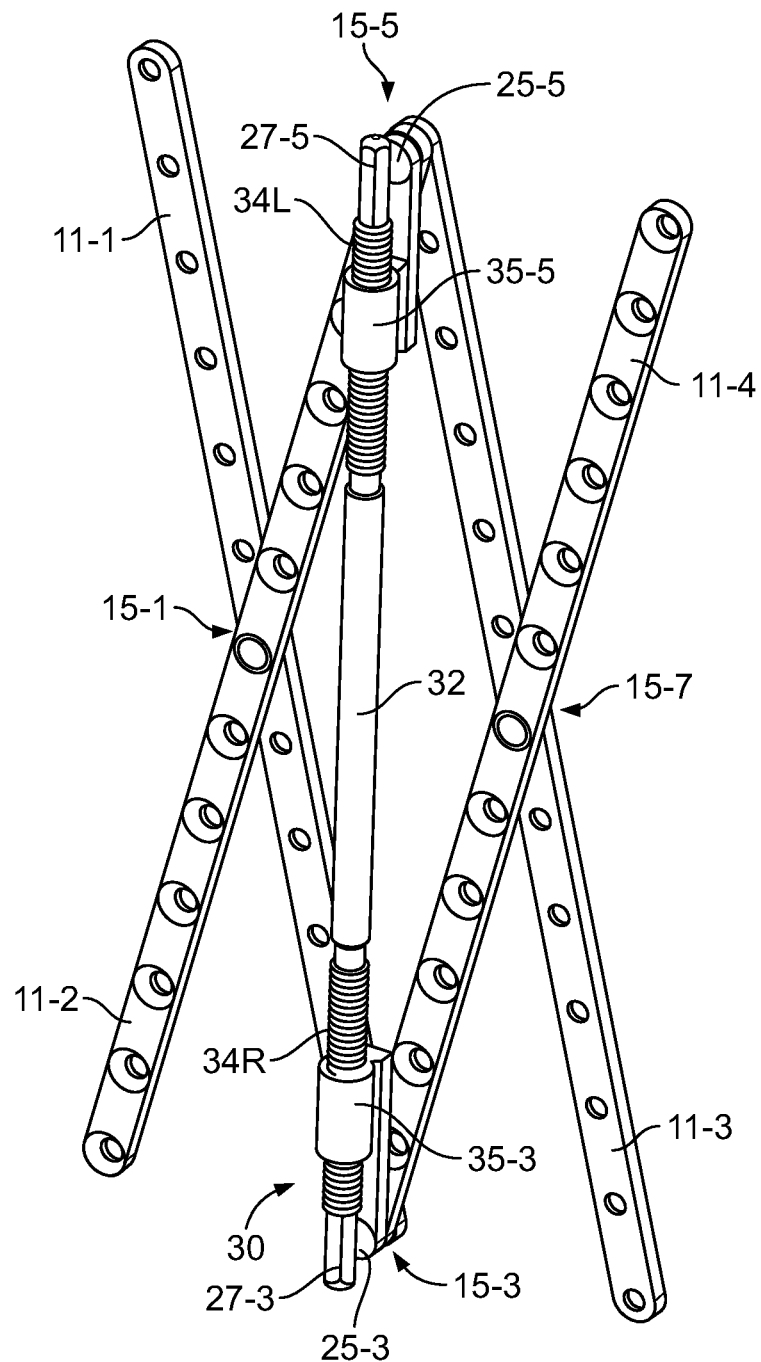
FIG. 8A is a perspective view of a linkage of the support structure of FIG. 1A having a particular actuator.

FIG. 8A is a perspective view of a linkage of the support structure 10 of FIG. 1B having a particular actuator. As shown, the actuator 30 includes a dual-threaded rod 32 positioned on the inside of the support structure 10. It should be understood, however, that the actuator 30 can instead be positioned on the outside of the support structure 10, or within the thickness of the strut members, instead of inside or outside of the stent. Whether positioned on the inside or outside, the actuator 30 may operate in the same way. The rod may include right-hand threads 34R on its proximal end and left-hand threads 34L on its distal end. The rod 32 may be mounted the anchor articulated joints 15-3, 15-5 using a pair of threaded low-profile support mounts 35-3, 35-5. Each end of the rod 32 may be terminated by a hex head 37-3, 37-5 for receiving a hex driver (not shown). As should be understood, rotating the rod 32 in one direction may urge the anchor fasteners 25-3, 25-5 outwardly to compress the linkages while rotating the rod 32 in the opposite direction may urge the anchor fasteners 25-3, 25-5 inwardly to expand the linkages.

Figure 9:
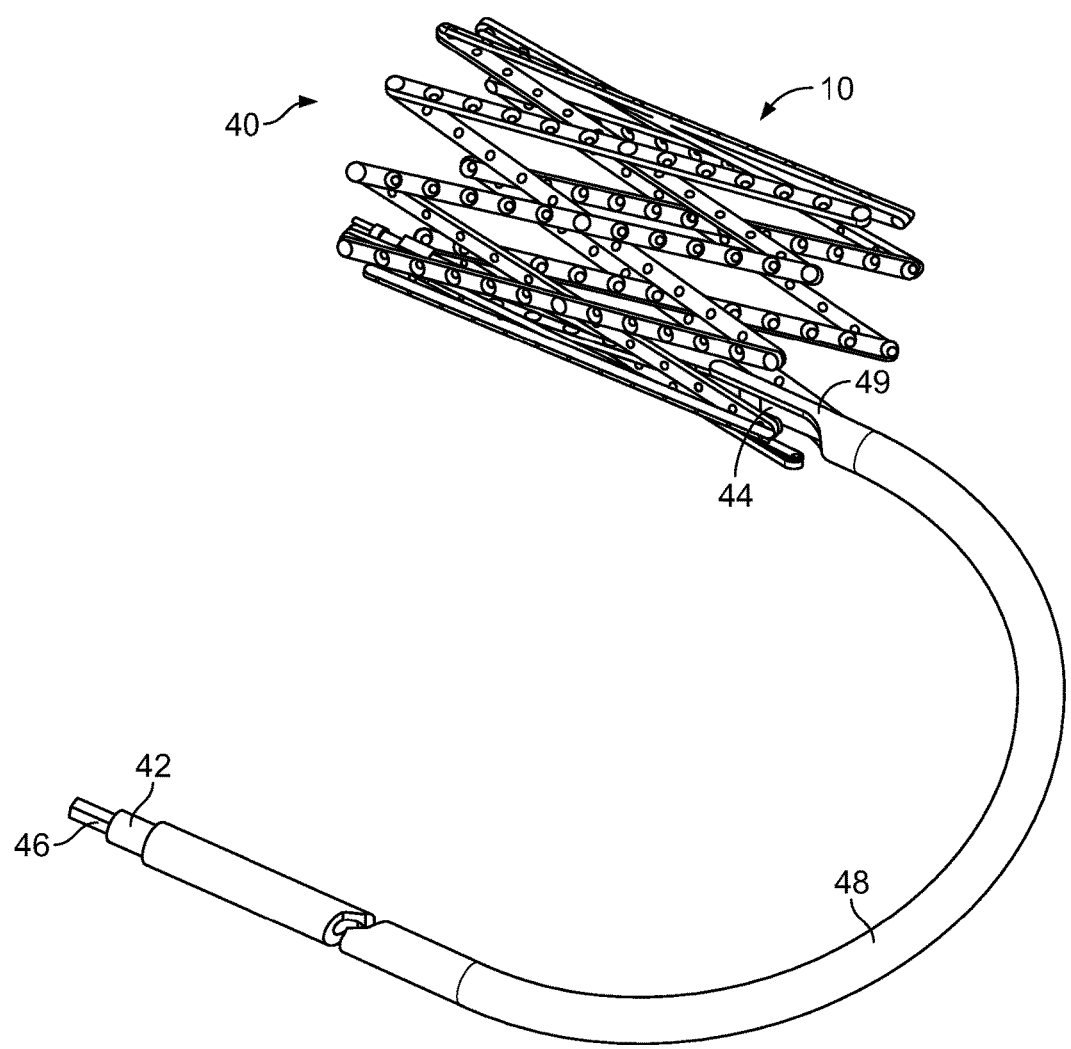
FIG. 9 is a perspective view of a particular support structure and control catheter assembly usable with the actuator of FIGS. 8A and 8B.

FIG. 9 is a perspective view of the support structure of FIG. 1A having another particular actuator. As shown, the actuator 30' includes a single-threaded rod 32' positioned on the inside of the support structure 10 (FIG. 1A). The rod 32' may include threads 34' on one of its ends. The rod 32' may be mounted to low profile anchor articulated joints 15-3, 15-5 using a pair of support mounts 35'-3, 35'-5, one of which is threaded to mate with the rod threads 34'. The unthreaded end of the rod 32' may include a retaining stop 39' that bears against the support mount 35'-5 to compress the support structure. Each end of the rod 32' can be terminated by a hex head 37'-3, 37'-5 for receiving a hex driver (not shown). Again, rotating the rod 32' in one direction may urge the anchor fasteners 25-3, 25-5 outwardly to compress the linkages while rotating the rod 32' in the opposite direction may urge the anchor fasteners 25-3, 25-5 inwardly to expand the linkages.

In a particular embodiment, the rod 32, 32' may have a diameter of about 1.0 mm and a thread count of about 240 turns/inch. By employing threads, the rod may be self-locking to maintain the support structure in the desired diameter. In addition, because the struts overlap, a ratcheting mechanism can be incorporated to be utilized during the sliding of one strut relative to the other. For example, the stent could lock at incremental diameters due to the interaction of features that are an integral part of each strut. An example of such features would be a male component (e.g. bumps) on one strut surface which mates with the female component (e.g. holes) on the surface of the neighboring strut surface, as the two struts slide pass one another. Such structures could be fabricated to have an orientation, such that they incrementally lock the stent in the expanded configuration as the stent is expanded. Such a stent could be expanded using a conventional balloon or other actuator described in this application.

Figure 8B:
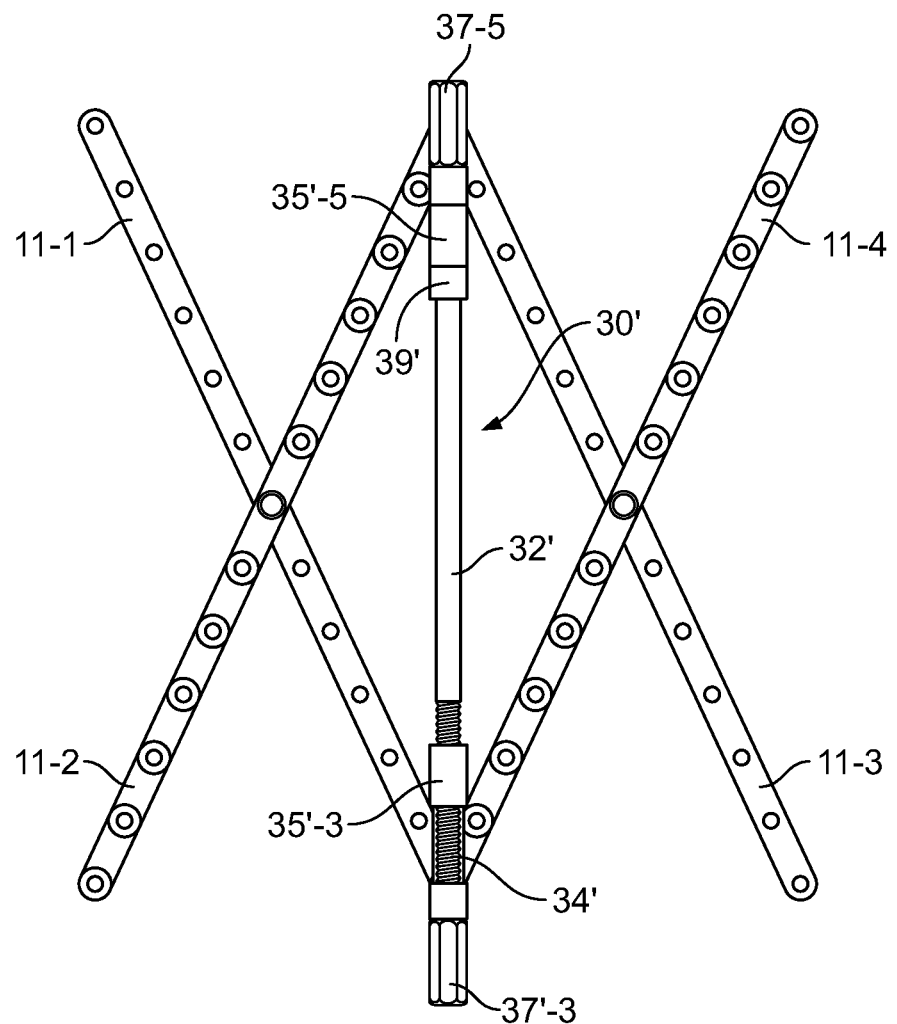
FIG. 8B is a perspective view of a linkage of the support structure of FIG. 1A having another particular actuator.

Because the support structure 10 may be configured to be implanted during a closed surgical procedure, the actuator may be able to be controlled remotely by a surgeon. FIG. 9 is a perspective view of a particular support structure and control catheter assembly usable with the actuators of FIGS. 8A-8B. The control catheter 40 may be dimensioned to be inserted with the support structure through a biological lumen, such as a human artery. As shown, the control catheter 40 includes a flexible drive cable 42 having a driver 44 on its distal end that removably mates with a hex head 37, 37' of the actuator (FIGS. 8A-8B). The proximal end of the cable 42 can include a hex head 46. In operation, the proximal hex head 46 of the cable 42 may be rotated by a surgeon, using a thumb wheel or other suitable manipulator (not shown). Rotation of the hex head 46 may be transferred by the cable 42 to the driver head 44 to turn the actuator rod 30, 30' (FIGS. 8A-8B).

The cable 42 may be encased by a flexible outer sheath 48. The distal end of the outer sheath 48 may include a lip or protuberance 49 shaped to interface with the support structure 10. When the cable 42 is turned, the outer sheath lip 49 may interact with the support structure 10 to counteract the resulting torque.

While a threaded rod and drive mechanism are described, other techniques can be employed to actuate the linkages depending on the particular surgical application. For example, worm gears or a rack and pinion mechanism can be employed as known in the art. One of ordinary skill in the art should recognize other endoluminal actuation techniques. In other situations, the support structure can be implanted during an open procedure, which may not require an external actuator.

Figure 10:
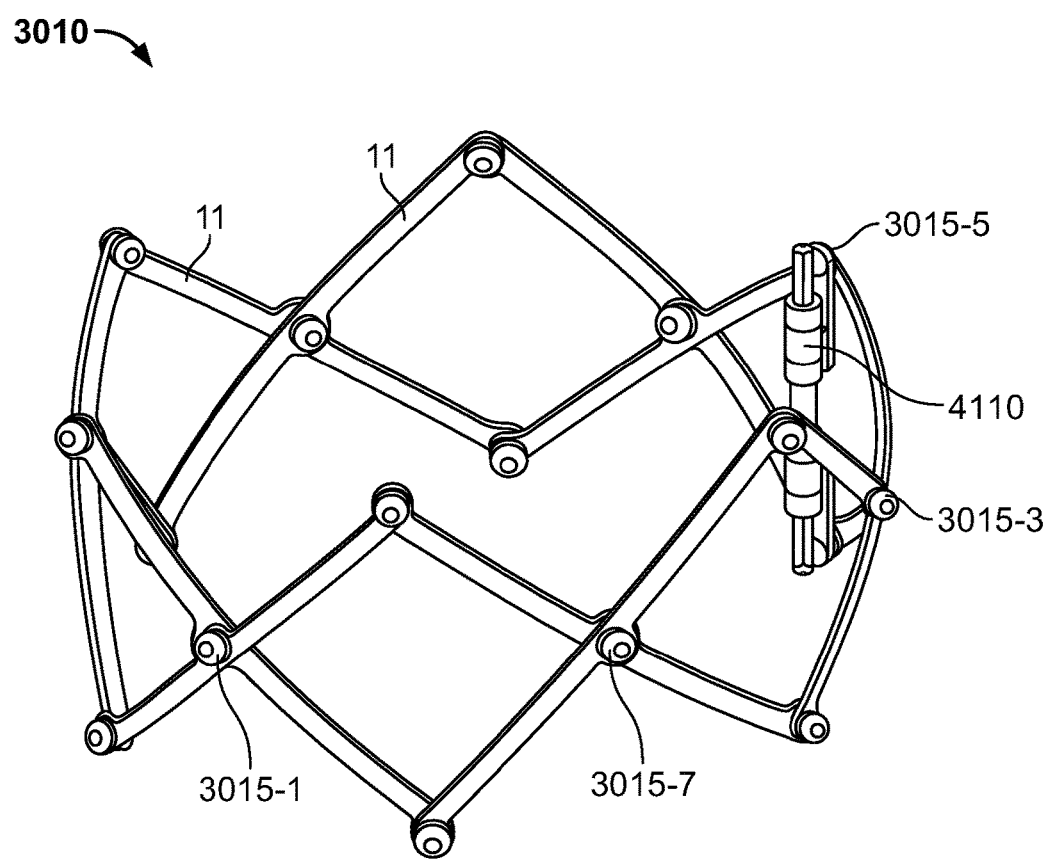
FIG. 10 is a side perspective view of the support structure of FIG. 2A having a particular actuator.

Although the actuators above are described with respect to use with support structure 10, similar actuators may be used with the other support structures and combinations of support structure described herein (e.g., support structures 10, 10', 2510, 2710, 3910, 3810, 4610 and combinations thereof). For example, FIG. 10 shows an actuator similar to the actuator of FIGS. 8A-8B attached to support structure 3010. As shown, the actuator 4110 may have a rod-like shape. The actuator may be attached to the support structure in any suitable manner for reversibly moving the support structure between compressed and expanded configurations, as described in detail above. As shown in FIG. 10, in one variation one end of the actuator 4110 may be attached to the inside of articulated joint 3015-5 of support structure 3010, and the other end of the actuator 4110 may be attached to the inside of articulated joint 3015-3 of support structure 3010. As shown, the actuator 4110 may comprise a rod having an adjustable length. The rod may comprise two components interconnected by threading (e.g., a microscrew); when two components are rotated relative to each other, the length of the rod may be incrementally and reversibly adjustable between and extended configuration with a longer length and a collapsed configuration with a shorter length. Extending the length of the rod 4110 may cause the joints to which the rod is attached to move longitudinally away from each other, causing the support structure to compress. Shortening the length of the rod may cause the joints to which the rod is attached to move longitudinally toward each other, causing the support structure to expand. The actuator 4110 may be controlled remotely by a surgeon. In some variations, the actuator 4110 may be able to be controlled via a catheter, such as the control catheters described herein.

Figure 11A:
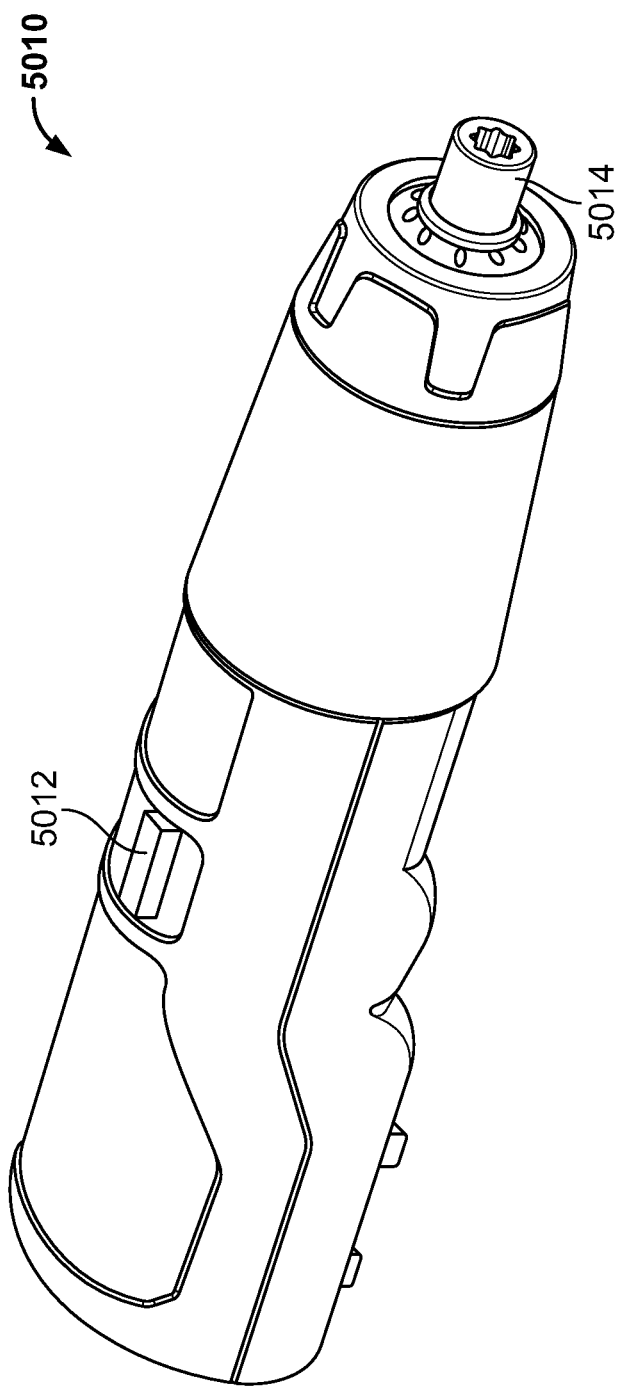
FIG. 11A shows a rotary instrument for controlling an actuator from a location remote from the implant site.
Figure 11B:
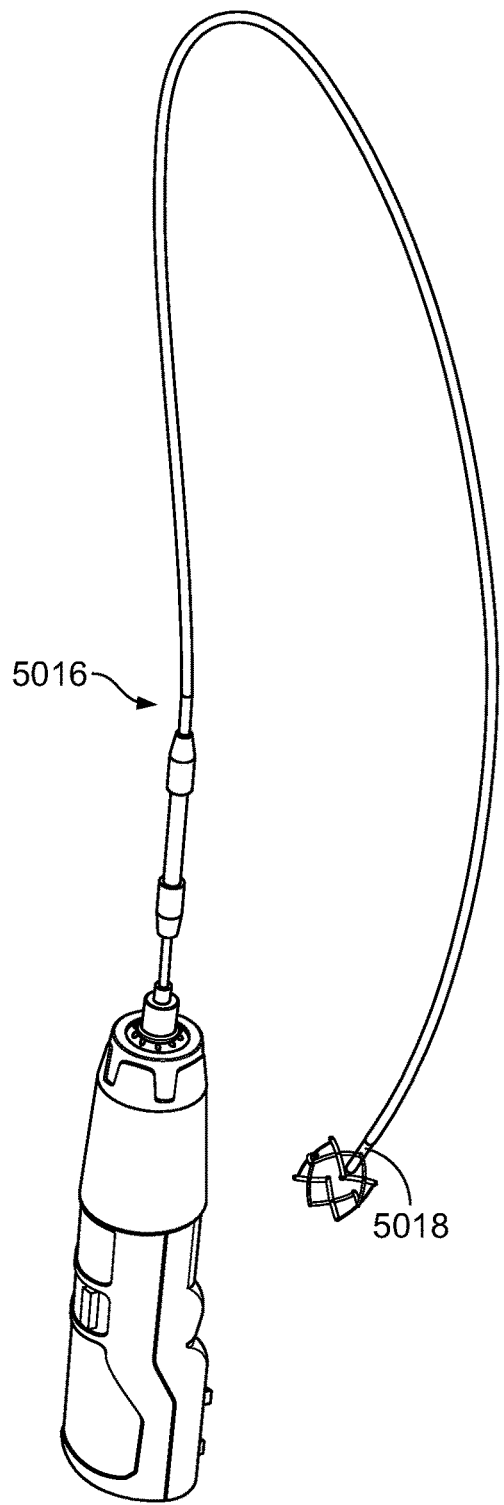
FIG. 11B shows the rotary instrument of FIG. 11A with an attached catheter, attached to the actuator and support structure of FIG. 10.
Figure 11C:
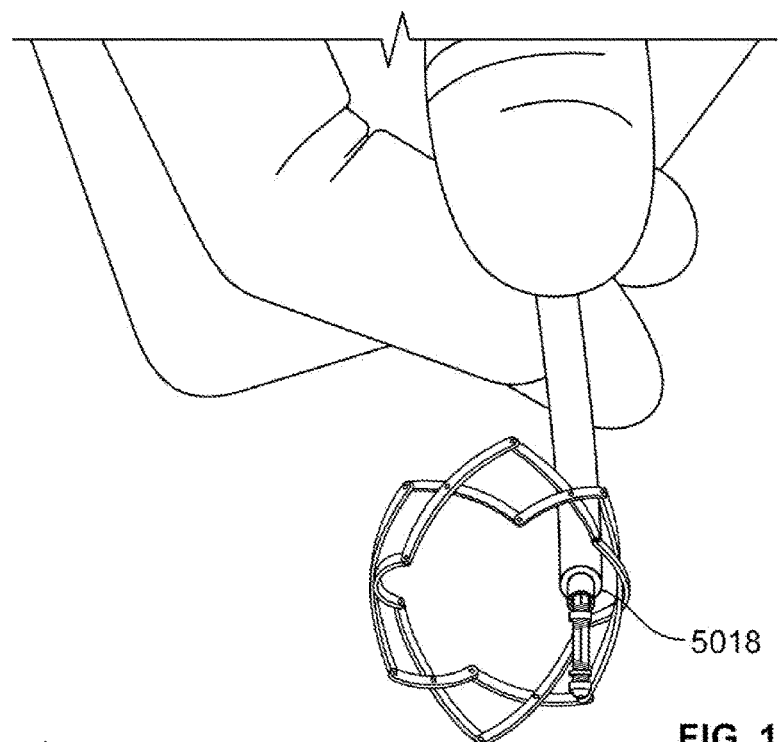
FIGS. 11C-11D show the end of the catheter attached to the actuator and support structure of FIG. 20 in expanded and compressed configurations, respectively.
Figure 11D:
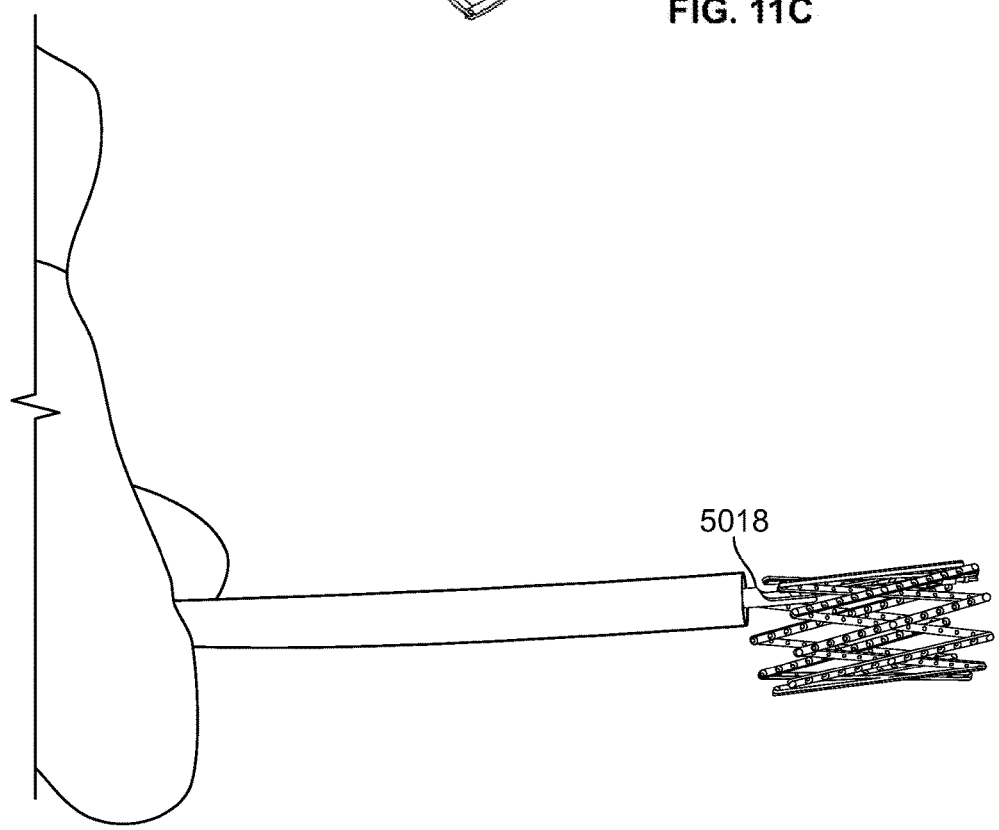
Figure 12:
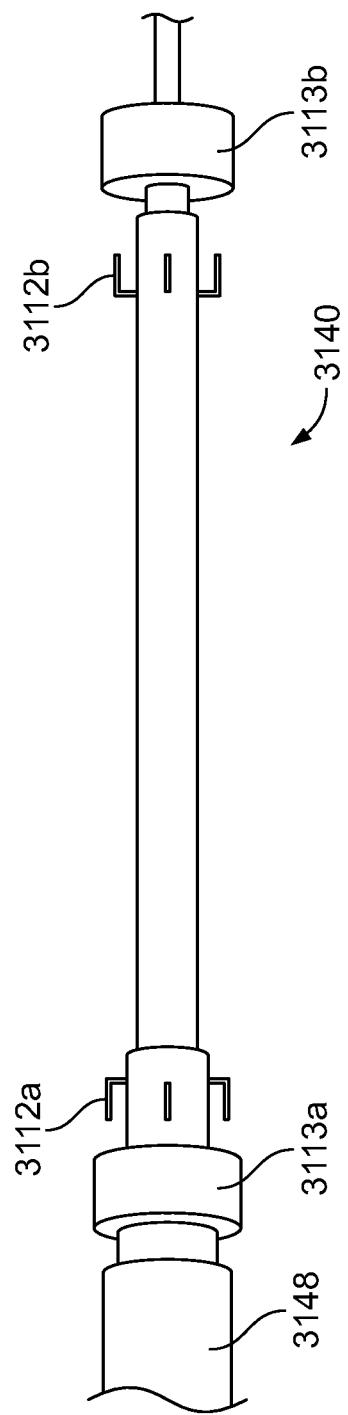
FIG. 12 is a side view of a control catheter assembly.

FIGS. 11A-11B show a rotary instrument 5010 for controlling an actuator, such as the actuators discussed above with respect to FIGS. 8A-18B, 9, and 10 from a location remote from the implant site. The rotary instrument 5010 may be configured to exert a rotational force. In some variations, the rotary instrument 5010 may be configured to exert bi-directional force, and may have a low RPM. The rotary instrument 5010 may comprise a control button 5012 that may be used to turn the rotary instrument 5010 on/off and/or to the control the speed and/or direction of the rotation. The proximal end 5014 of the rotary instrument 5010 may comprise an attachment port for a catheter assembly 5016. The catheter assembly 5016 may comprise a flexible catheter having an outer sheath, as shown in FIG. 11B. The proximal end 5018 of the catheter may attach to an actuator, as shown in FIGS. 11C-11D. By rotating the microscrew of the actuator, as described in more detail above, the rotary instrument may allow for fine, incremental changes in the size of the support structure. The changes may be reversible, and may allow for continuous auto-locking at each size.

Valves

Although there are other uses for the support structures described herein, such as drug delivery, in some variations, the support structures may be configured to support a prosthetic valve. In particular, the support structure may be used in combination with a prosthetic valve, such as for an aortic or mitral valve replacement.

The support structures may support prosthetic valves comprising a plurality of leaflets. The leaflets may be derived from a biocompatible material or materials, which may be either biological or non-biological, or a combination. For example, the leaflets may comprise animal pericardium (e.g. bovine, porcine, equine), human pericardium, chemically treated pericardium, gluteraldehyde-treated pericardium, tissue engineered materials, a scaffold for tissue engineered materials, autologous pericardium, cadaveric pericardium, Nitinol, polymers, plastics, PTFE, or any other material known in the art.

As supported by the support structures described herein, the valves may be configured to be actuated by utilizing the forces exerted by the normal blood flow or pressure changes of the cardiac cycle. More specifically, the heart may eject blood through the fully open valve. Shortly thereafter, the distal or downstream blood pressure may start to rise relative to the proximal pressure across the valve, which may create a backpressure on the valve. In considering the valve as an aortic valve replacement, it may remain closed until the heart enters systole. During systole, as the myocardium forcefully contracts, the blood pressure exerted on the valve's proximal side (the side closest to the heart) may be greater than the pressure on the distal side (downstream) of the closed valve. The valve may passively function to provide unidirectional blood flow.

In some variations, the valves may comprise three leaflets, which may be attached to the support structure in a triangular configuration. This triangular configuration may simulate the angled attachment of the native leaflet and allow for anatomical draping of the tissue. In the native valve this creates an anatomical structure between leaflets, known as the inter-leaflet trigone. Because the anatomical inter-leaflet trigone is believed to offer structural integrity and durability to the native leaflets in humans, it is advantageous to simulate this structure in a prosthetic valve.

Figure 13:
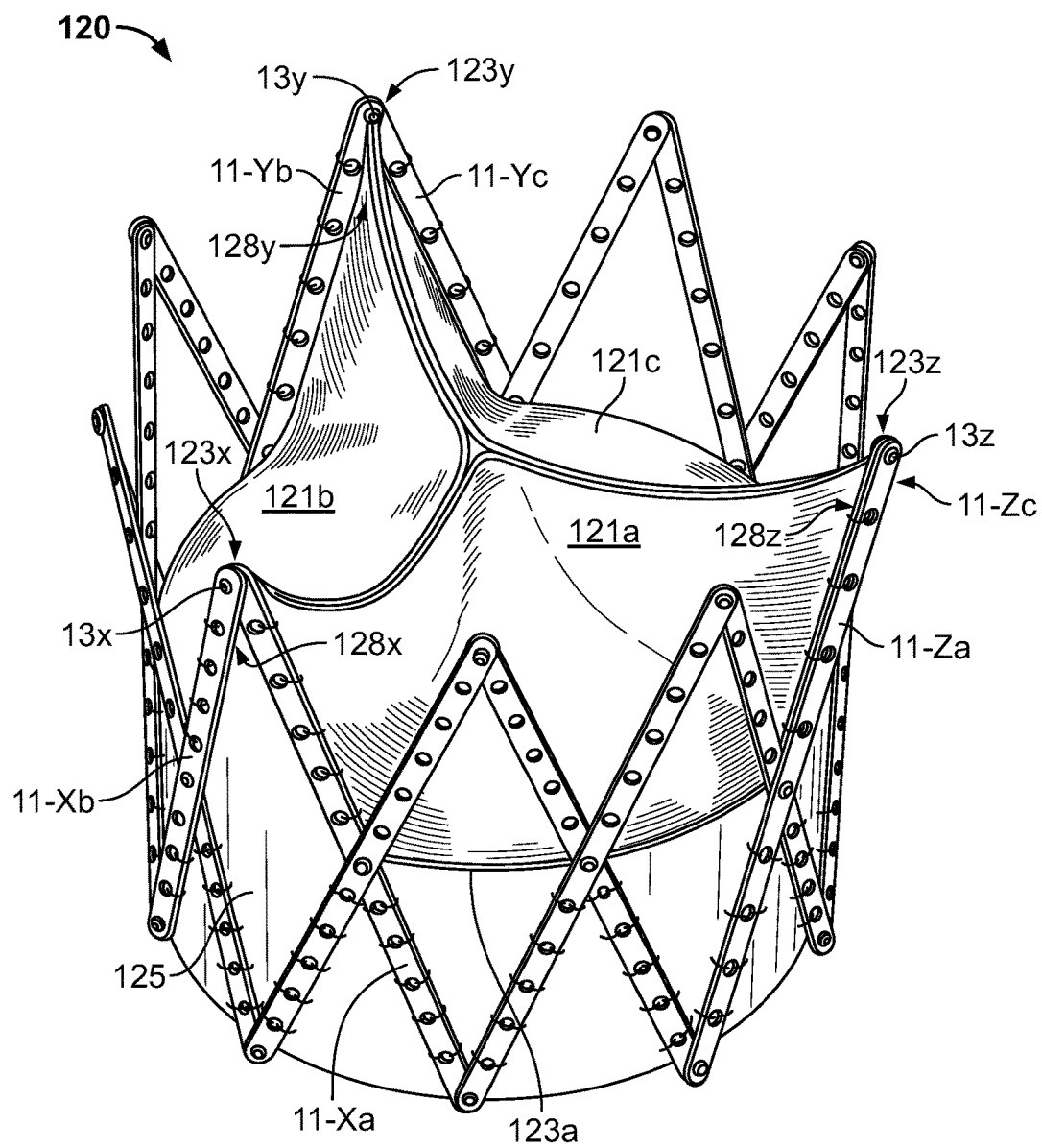
FIG. 13 is a perspective view of a tissue valve mounted to the support structure of FIG. 1A.

FIG. 13 is a perspective view of a tissue valve mounted to the support structure of FIG. 1A. As shown, a stented valve 120 may include a prosthetic tissue valve 121 attached to a support structure 10, such as that described above.

The tissue valve 121 may include three pliable semi-circular leaflets 121a, 121b, 121c, which can be derived from biocompatible materials as noted above. Adjacent leaflets may be attached in pairs to commissures 123x, 123y, 123z on the support structure 10. In particular, the commissures 123x, 123y, 123z correspond to spaced-apart distal anchor points 13x, 13y, 13z on the support structure 10. In an 18-strut stent, the commissures may be attached the structure 10 via corresponding fasteners 25 at every third distal anchor point.

From the commissures, the leaflet sides may be connected to the adjacent diagonal struts. That is, the sides of the first leaflet 121a may be sutured to the struts 11-Xa and 11-Za, respectively; the sides of the second leaflet 121b may be sutured to the struts 11-Xb and 11-Yb, respectively; and the sides of the third leaflet 121c may be sutured to the struts 11-Yc and 11-Zc, respectively. Those sutures may end at the scissor articulated joints on the diagonal struts.

In the configuration shown, neighboring struts 11 may be attached to one another in a manner that creates multiple arches 128 at the ends of the stent. Posts for leaflet attachment, or commissures, may be formed by attaching a corresponding leaflet to each of the struts that define a suitable arch 128x, 128y, 128z. In the configuration shown, there may be three leaflets 121a, 121b, 121c, each of which is attached to a strut along two of its opposing borders. The commissures may be formed by three equidistant arches 128x, 128y, 128z in the stent.

The angled orientation of a strut in relationship to its neighboring strut may permit the leaflets 121a, 121b, 121c to be attached to the stent in a triangular configuration. This triangular configuration simulates the angled attachment of the native aortic leaflet. In the native valve this creates an anatomical structure between leaflets, known as the inter-leaflet trigone. Because the anatomical inter-leaflet trigone is believed to offer structural integrity and durability to the native aortic leaflets in humans, it may be advantageous to simulate this structure in a prosthetic valve.

One method of attachment of the leaflets to the struts is to sandwich the leaflet between a multi-ply strut. The multiple layers may then be held together by sutures, or the attachment may be sutureless. Sandwiching the leaflets between the struts may help to dissipate the forces on leaflets and prevent the tearing of sutures through the leaflets. The remaining side of each leaflet 121a, 121b, 121c may be sutured annularly across the intermediate strut members as shown by a leaflet seam.

Figure 14:
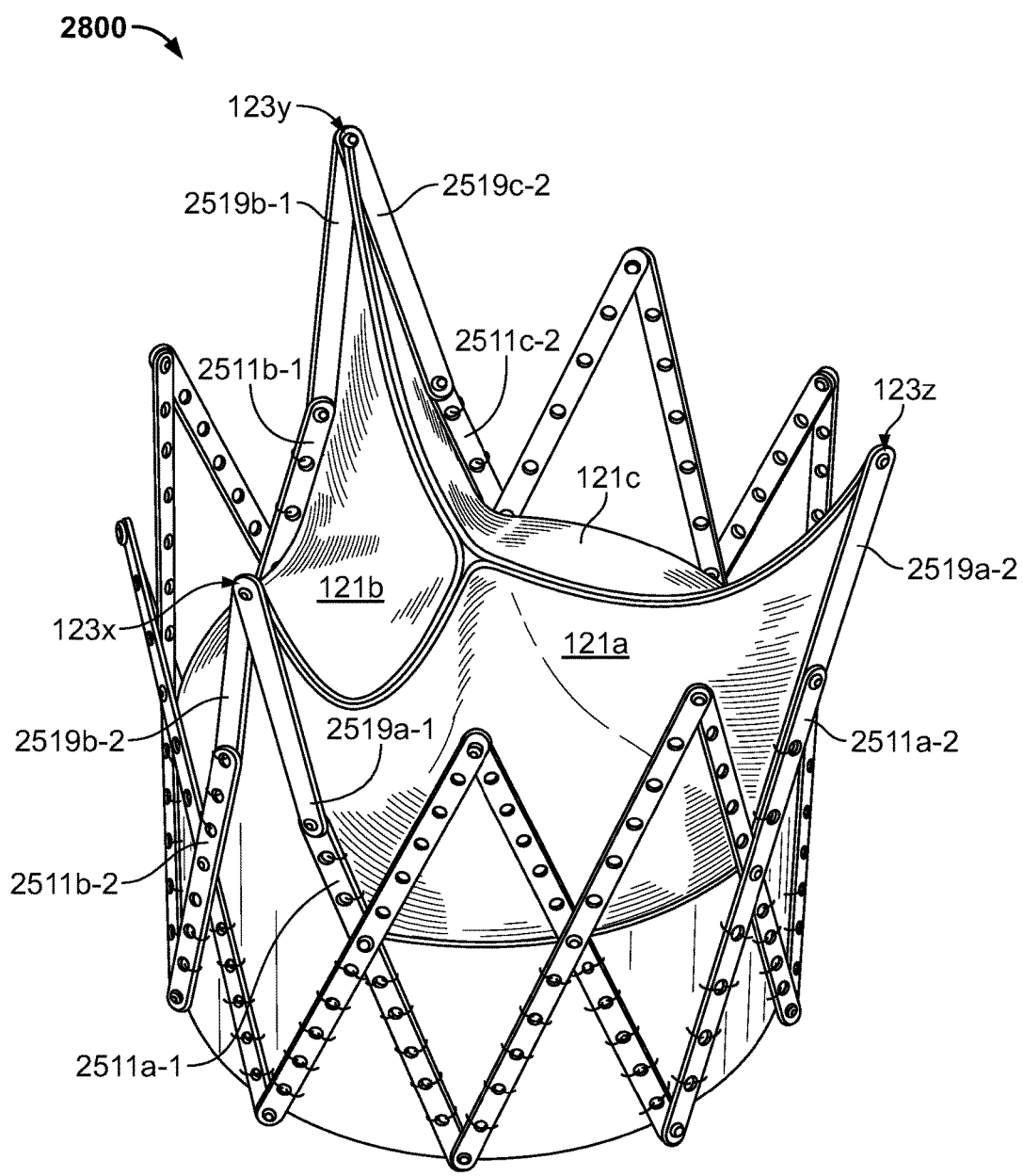
FIG. 14 is a perspective view of a tissue valve mounted to the structure of FIG. 10A.

FIG. 14 is a perspective view of a tissue valve mounted to the support structure of FIG. 6A. As shown, a stented valve 2800 may include a prosthetic tissue valve 121, as described above, to a support structure 2510, as described above. Adjacent leaflets may be attached in pairs to commissures 123x, 123y, 123z on support structure 2510, which correspond to the distal articulated joints 2515 located at the distal ends of commissure strut members 2519.

From the commissures, the leaflet sides may be connected to the adjacent struts. That is, the sides of the first leaflet 121a may be sutured to the struts 2511a-1, 2519a-1, 2511a-2, 2519a-2; the sides of the second leaflet 121b may be sutured to the struts 2511b-1, 2519b-1, 2511b-2, 2519b-2; and the sides of the third leaflet 121c may be sutured to the struts 2511c-1, 2519c-1, 2511c-2, 2519c-2. Those sutures end at the scissor articulated joints 2515 on the longitudinal struts 2511.

Like the attachment of leaflets to support structure 10 shown in FIG. 13, the angled orientation of a strut in relationship to its neighboring strut may enable the leaflets 121a, 121b, 121c to be attached to the stent in a triangular configuration, as described in more detail above.

The tissue valve mounted to support structure shown in FIG. 6A may also be modified to sandwich the leaflets between multi-ply struts, and to drape the open spaces between the struts with a biocompatible skirt, as described in more detail below.

In another embodiment, the tissue valve 121 may be mounted to the support structure 2510 in a secure, sutureless manner. Leaflets 121a, 121b, 121c can be suturelessly attached at the distal tip of commissures 123x, 123y, 123z, and along the distal portion of struts 2511. In some variations, the leaflets 121a, 121b, 121c can also be suturelessly attached along struts 2519. More particularly, the sides of leaflet 121a may be suturelessly attached to the struts 2511a-1, 2511a-2; the sides of leaflet 121b may be suturelessly attached to the struts 2511b-1, 2511b-2; and the sides of leaflet 121c may be suturelessly attached to the struts 2511c-1, 2511c-2. In some variations, the sides of leaflet 121a can be suturelessly attached to the struts 2919a-1, 2519a-2; the sides of leaflet 121b can be suturelessly attached to the struts 2519b-1, 2519b-2; and the sides of leaflet 121c can be suturelessly attached to the struts 2519c-1, 2519c-2.

The sutureless attachments may be formed by draping the leaflets over the distal tips of commissures 123x, 123y, 123z; sandwiching the leaflets between struts at articulated joints; or sandwiching the leaflets between multi-ply struts. More particularly, the sides of leaflet 121a can be sandwiched between the commissure strut 2519c-1 and commissure strut 2519a-2 at the articulated joint at distal tip of commissure 123z; sandwiched between commissure strut 2519a-2 and longitudinal strut 2511a-2 at the connecting articulated joint; sandwiched between longitudinal strut 2511a-2 and the rotatably attached longitudinal strut 2511 at the middle articulated joint 2515; sandwiched between commissure strut 2519a-1 and commissure strut 2519b-2 at the articulated joint at distal tip of commissure 123x; sandwiched between commissure strut 2519a-1 and longitudinal strut 2511a-1 at the connecting articulated joint; and sandwiched between longitudinal strut 2511a-1 and the rotatably attached longitudinal strut 2511 at the middle articulated joint 2515. The rivets 2525 at these articulated joints may pass through the leaflet 121a.

The sides of leaflet 121b can be sandwiched between the commissure strut 2519a-1 and commissure strut 2519b-2 at the articulated joint at distal tip of commissure 123x; sandwiched between commissure strut 2519b-2 and longitudinal strut 2511b-2 at the connecting articulated joint; sandwiched between longitudinal strut 2511b-2 and the rotatably attached longitudinal strut 2511 at the middle articulated joint 2515; sandwiched between commissure strut 2519b-1 and commissure strut 2519c-2 at the articulated joint at distal tip of commissure 123y; sandwiched between commissure strut 2519b-1 and longitudinal strut 2511b-1 at the connecting articulated joint; and sandwiched between longitudinal strut 2511b-1 and the rotatably attached longitudinal strut 2511 at the middle articulated joint 2515. The rivets 2525 at these articulated joints may pass through the leaflet 121b.

The sides of leaflet 121c can be sandwiched between the commissure strut 2519b-1 and commissure strut 2519c-2 at the articulated joint at distal tip of commissure 123y; sandwiched between commissure strut 2519c-2 and longitudinal strut 2511c-2 at the connecting articulated joint; sandwiched between longitudinal strut 2511c-2 and the rotatably attached longitudinal strut 2511 at the middle articulated joint 2515; sandwiched between commissure strut 2519c-1 and commissure strut 2519a-2 at the articulated joint at distal tip of commissure 123z; sandwiched between commissure strut 2519c-1 and longitudinal strut 2511c-1 at the connecting articulated joint; and sandwiched between longitudinal strut 2511c-1 and the rotatably attached longitudinal strut 2511 at the middle articulated joint 2515. The rivets 2525 at these articulated joints may pass through the leaflet 121c.

In another embodiment, struts 2511a-1, 2511a-2, 2511a-3, 2511b-1, 2511b-2, 2511b-3, 2511c-1, 2511c-2, 2511c-3, 2519a-1, 2519a-2, 2519a-3, 2519b-1, 2519b-2, 2519b-3, 2519c-1, 2519c-2, 2519c-3 are multi-ply struts, and the leaflets 121a, 121b, 121c are sandwiched between the two or more layers of the struts. More particularly, one side of leaflet 121a may be sandwiched within the multi-ply strut making up commissure strut 2519a-1 and the multi-ply strut making up the distal portion of longitudinal strut 2511a-1, and the other side of leaflet 121a may be sandwiched within the multi-ply strut making up commissure strut 2519a-1 and the multi-ply strut making up the distal portion of longitudinal strut 2511a-2. One side of leaflet 121b may be sandwiched within the multi-ply strut making up commissure strut 2519b-1 and the multi-ply strut making up the distal portion of longitudinal strut 2511b-1, and the other side of leaflet 121b may be sandwiched within the multi-ply strut making up commissure strut 2519b-1 and the multi-ply strut making up the distal portion of longitudinal strut 2511b-2. One side of leaflet 121c may be sandwiched within the multi-ply strut making up commissure strut 2519c-1 and the multi-ply strut making up the distal portion of longitudinal strut 2511c-1, and the other side of leaflet 121c may be sandwiched within the multi-ply strut making up commissure strut 2519c-1 and the multi-ply strut making up the distal portion of longitudinal strut 2511c-2.

Figure 15:
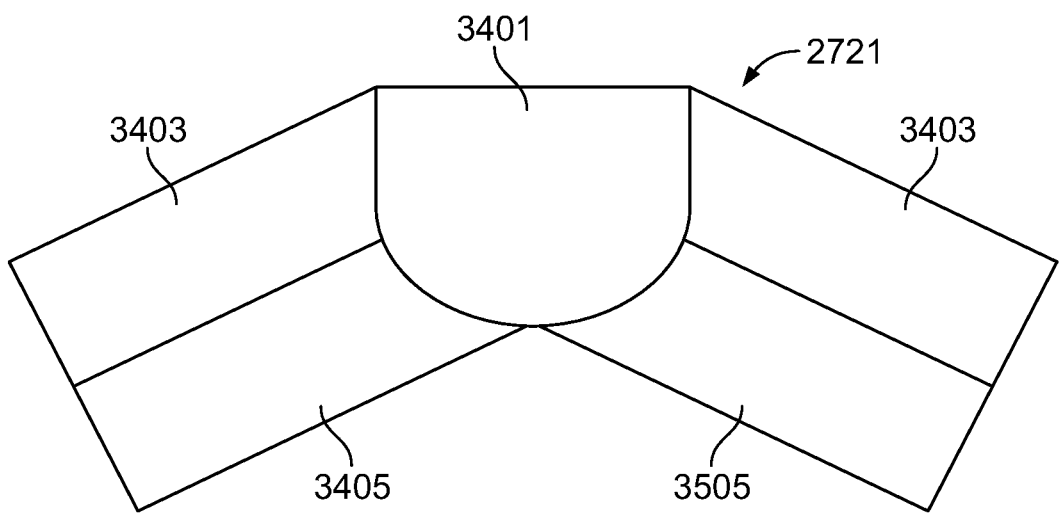
FIG. 15 is a schematic illustration of a valve leaflet.

In order to facilitate secure, suture-free leaflet attachment during fabrication through sandwiching of the leaflets between the struts, the leaflets 121a, 121b, 121c may comprise a shape as shown in FIG. 15 having a central region 3401 having a semicircular or paraboloid shape, with two rectangular regions extending from each side of the central region 3401. The upper rectangular regions 3403 may be sandwiched within multi-ply struts making up commissure struts 2519, and the lower rectangular regions 3405 may be sandwiched within multi-ply struts making up longitudinal struts 2511. After the upper regions 3403 and lower regions 3405 are sandwiched between the struts, the outer portions of the regions 3403, 3405 can be removed (e.g. by being cut off), leaving the central region 3401 suturelessly attached to the support structure 2510.

In other embodiments, tissue valves may be mounted to the other support structures described herein (e.g., support structures 10, 10', 2510, 2710, 3910, 3810, 4610) in the sutureless manner described above.

Skirts

In some variations, the support structures described here may have skirts. The skirt may function to reduce or eliminate leakage around the valve, or "paravalvular leak," and in particular, may have increased sealing when greater pressure is applied to the skirt. The skirt may comprise a thin layer of material that lines all or a portion of the structure. The material may be, but is not limited to, pericardial tissue, polyester, PTFE, or other material or combinations of materials suitable for accepting tissue in growth, including chemically treated materials to promote tissue growth or inhibit infection.

In the variation shown in FIG. 13, the remaining open spaces between the struts after attachment of the valve leaflets can be draped by a biocompatible skirt 125 to help seal the valve against the implant site and thus limit paravalvular leakage. As shown, the skirt 125 may be shaped to cover those portions of the stent below and between the valve leaflets.

In more detail, the skirt 125 at the base of the valve may be a thin layer of material that lines the stent wall. To that end, there are a number of ways to attach the skirt material layer to the stent. The skirt layer may be on the inside or the outside of the stent; it may occupy the lower portion of the stent, the upper portion of the stent, or the lower and upper portion of the stent; it may occupy the area between the struts that define the commissure posts; it may be continuous with the leaflet material; it may be sutured to the struts or a multitude of sites; and/or it may be secured to the lower portion of the stent, and pulled or pushed up to cover the outside of the stent during the deployment in the body. The above list is not necessarily limiting as those of ordinary skill in the art may recognize alternative draping techniques for specific applications.

Method of Fabrication

The support structures described herein, including the attachment of valve leaflets and skirts, may be fabricated via a sutureless assembly method. As such, the fabrication method may avoid the labor-intensive manual sewing generally involved in the fabrication of prosthetic valve replacements. However, it should be appreciated that the fabrication method need not be sutureless. In some variations, the assembly method may be automated. The fabrication method may be used to fabricate a support structure (e.g., an endoluminal support structure or a valve support structure) with or without an attached valve and/or skirt. In some variations, the fabrication method may be used to separately fabricate a valve support structure with an attached valve and skirt, and an endoluminal support structure with an attached skirt, and then these two support structures may be connected. In other variations, the fabrication method may be used to simultaneously fabricate the valve support component and the endoluminal support component.

In general, the fabrication method described herein comprises connecting the strut members, and any valve leaflets and/or skirts, in to a flattened chain. The flattened chain may then be shaped into the desired shape (e.g., a cylindrical shape).

In some variations, this fabrication method may allow the components of the support structure to be arranged in a fixed configuration on a separate support structure before being secured together. The flattened chain may be fabricated by layering the strut members, and any valve leaflets and/or skirts and then securing them together. The valve leaflets and/or skirt may be sandwiched between the strut members, securing them in place without the use of sutures. The components may thus be layered in the order in which they will be in the final support structure. In some variations, the components may be layered from the inner-most components to the outer-most components. In other variations, the components may be layered from the outer-most components to the inner-most components.

The fabrication method may use one or more plates and/or alignment guides to assist with alignment of the components. In general, one plate may be placed below the components, for the components to rest upon as they are layered. This plate may also comprise openings through which alignment guides may be placed, or alternatively, the plate may have permanently attached alignment guides. The alignment guides may comprise pins, which may be configured to fit through orifices in the strut members, valve leaflets, and skirt material. The strut members, valve leaflets, and skirt material may thus be held in alignment by the alignment guides. A second plate may be placed above the components after they are layered. Together, the two plates may allow the components to be removed from the alignment guides after they are layered, while maintaining their configuration, by applying compressive force to hold the components together.

After the components are layered, they may be secured together by securing elements (e.g., eyelets or rivets). In some variations, the securing elements may comprise openings through which the alignment guides may be placed, and the securing elements may be layered with the strut members, valve leaflets, and skirt material between the two plates. For example, in variations in which the securing elements comprise eyelets or rivets comprising a flange, the eyelets or rivets may be placed on the alignment guides above the first plate and before the bottom-most strut member. The flange may thus be sandwiched between the first plate and the bottom-most strut member. The eyelet or rivet may extend through the other components as they are layered onto the strut member, and the top side of the eyelet or rivet may be swaged after the layering is completed in order to secure the components together. In other variations, the eyelets or rivets may be layered after the other components. In variations in which a valve leaflet or skirt material is sandwiched between the strut members, the compressive force from the strut members on the valve leaflet or skirt once the components are secured together may hold the valve leaflet or skirt in place without the need for sutures, although in some variations sutures may also be used.

Figure 16A:
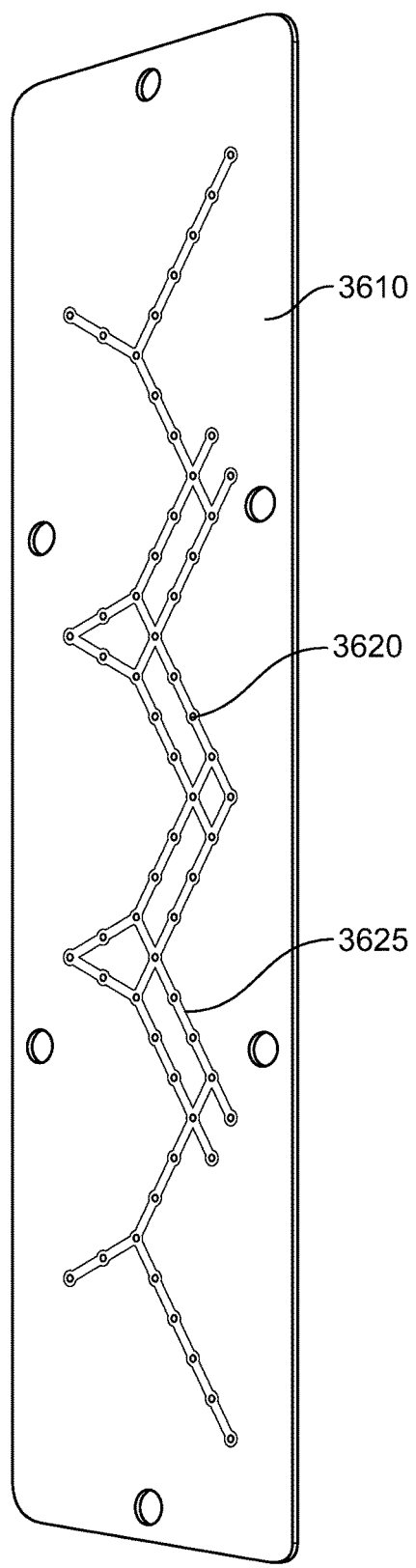
FIG. 16A is a top perspective view of a particular alignment plate.
Figure 16B:
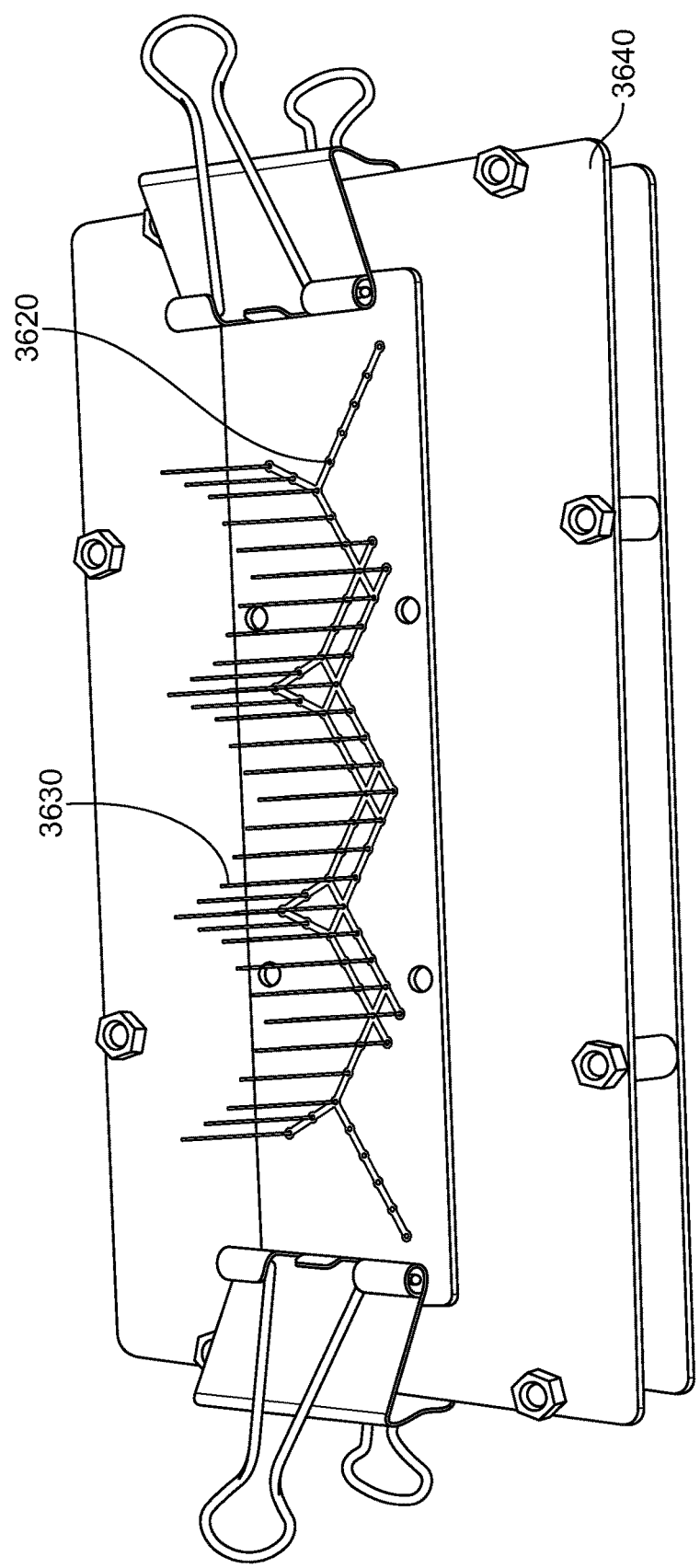
FIGS. 16B-16W show steps in a method of fabrication.
Figure 16C:
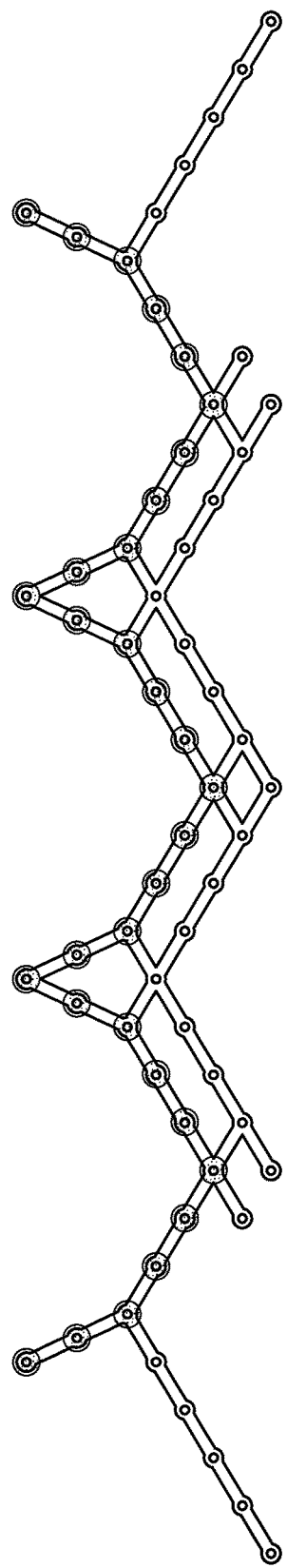
FIG. 16X is a top perspective view of a particular base frame.
Figure 16D:
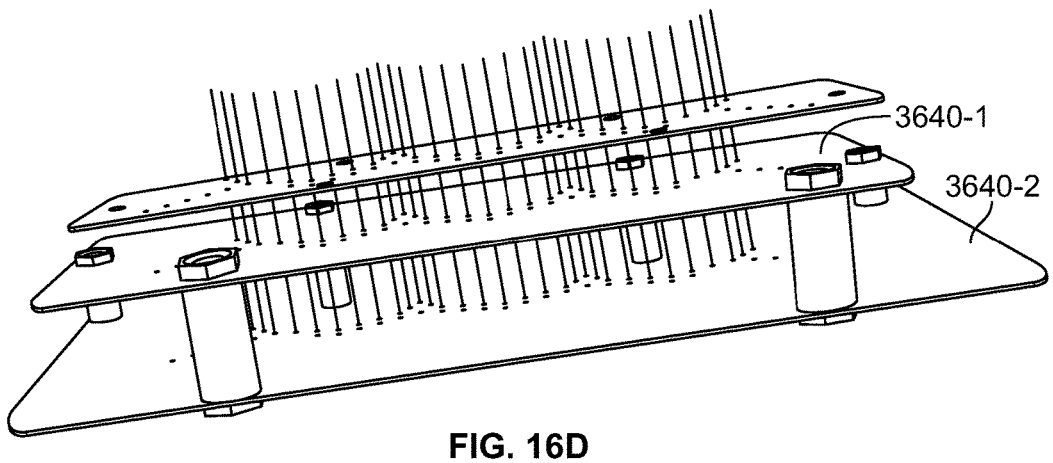
Figure 16E:
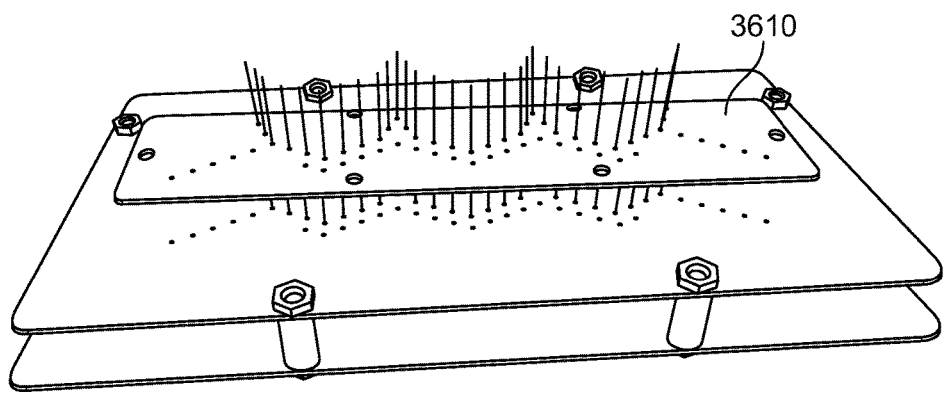
Figure 16F:
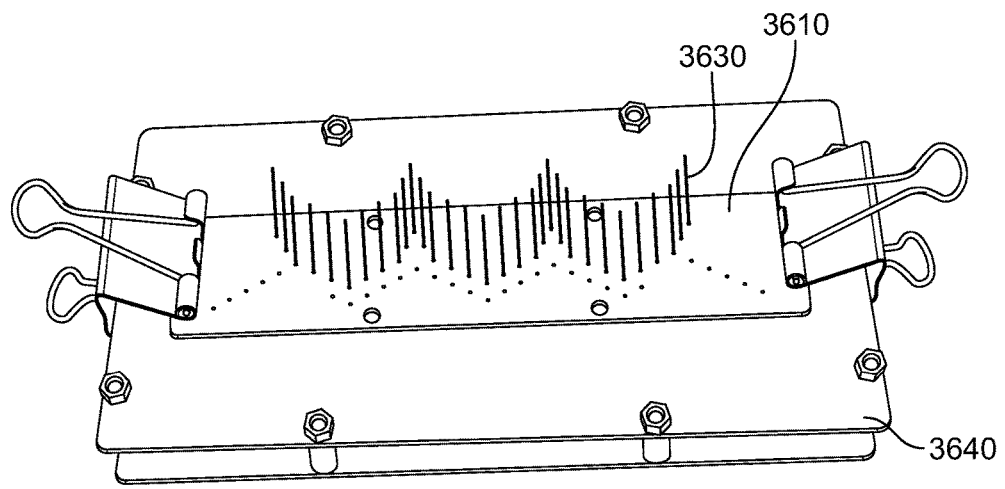
Figure 16G:
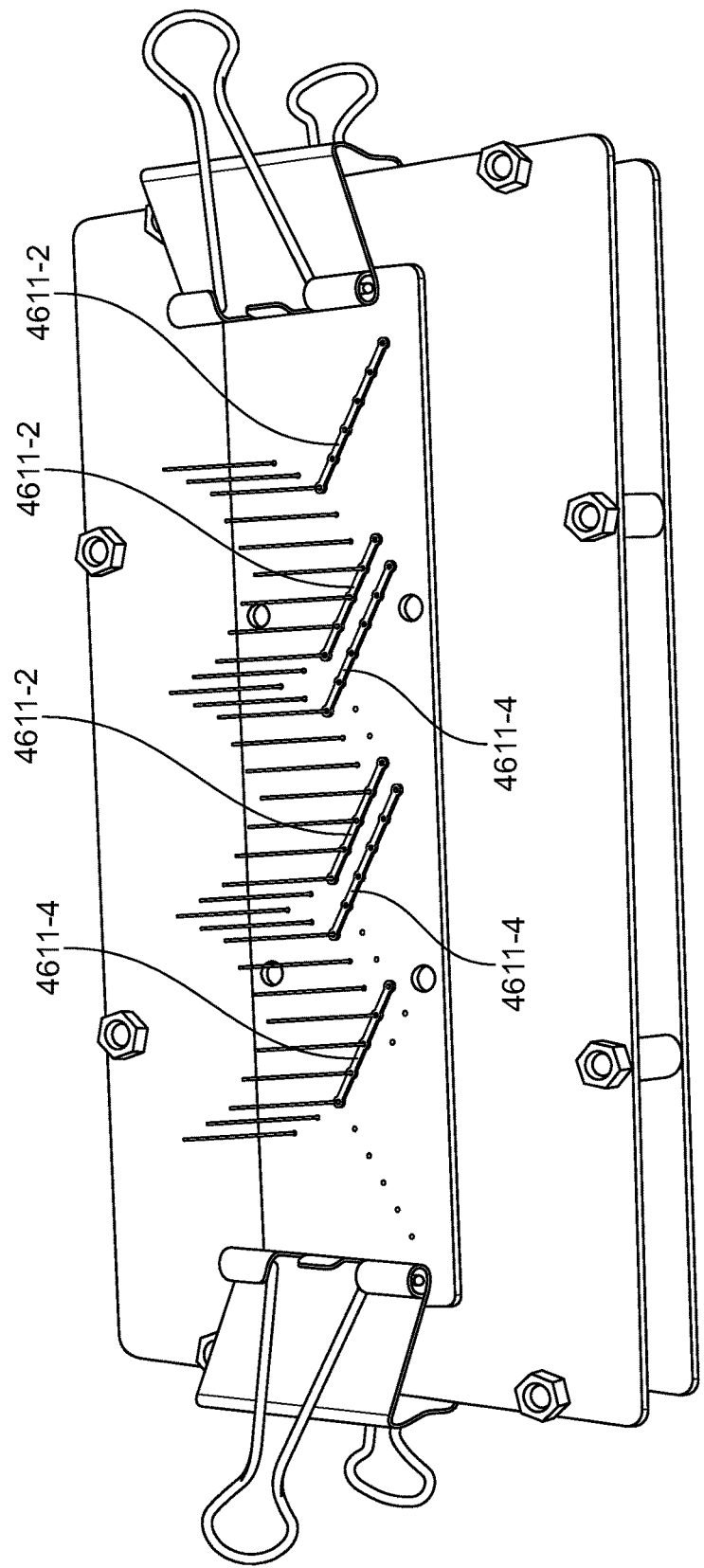
Figure 16H:
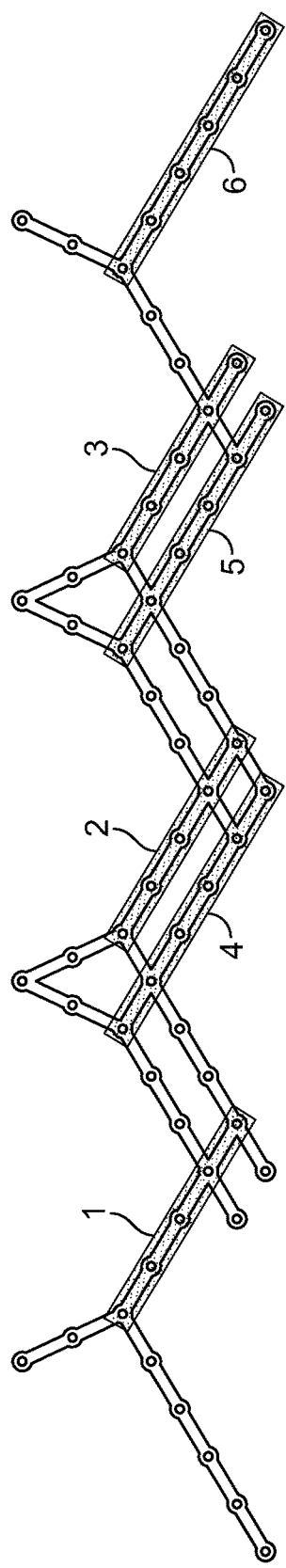
Figure 16I:
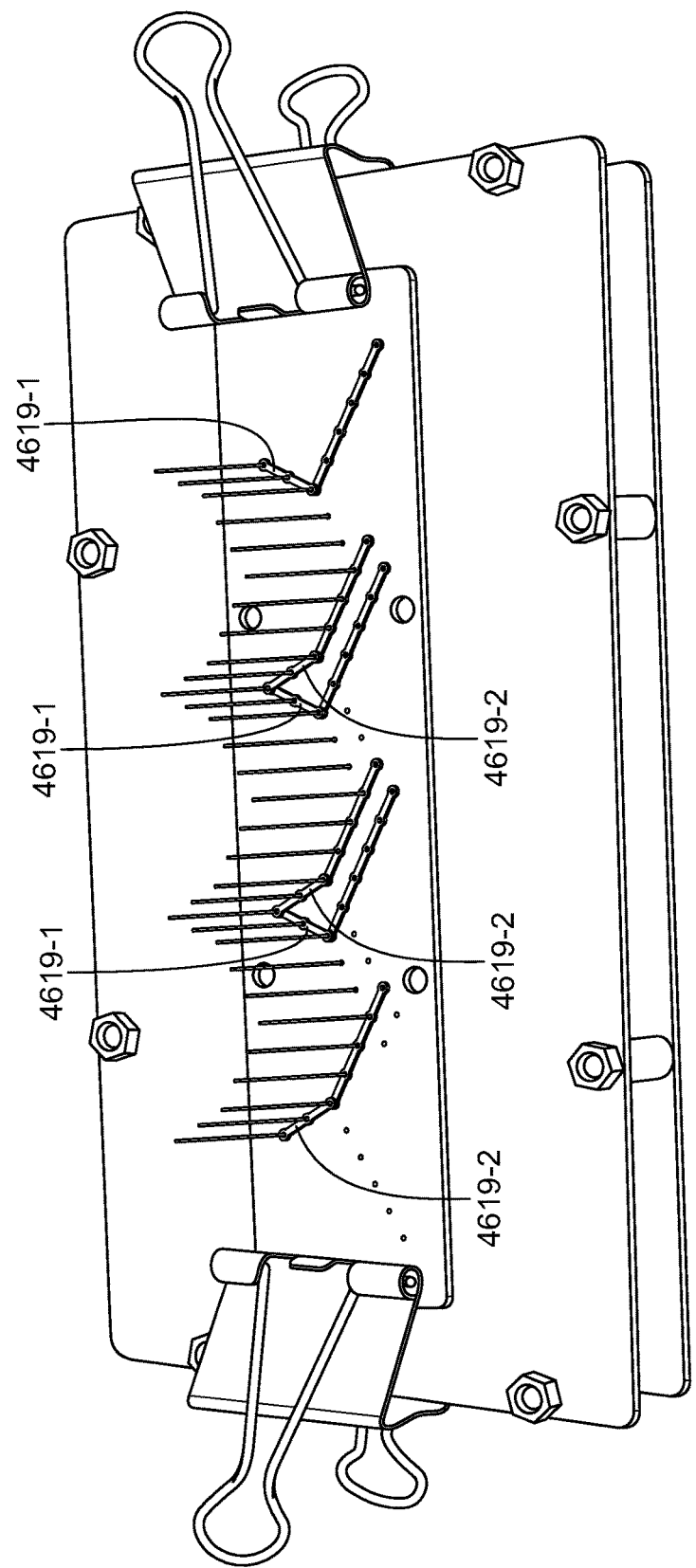
Figure 16J:
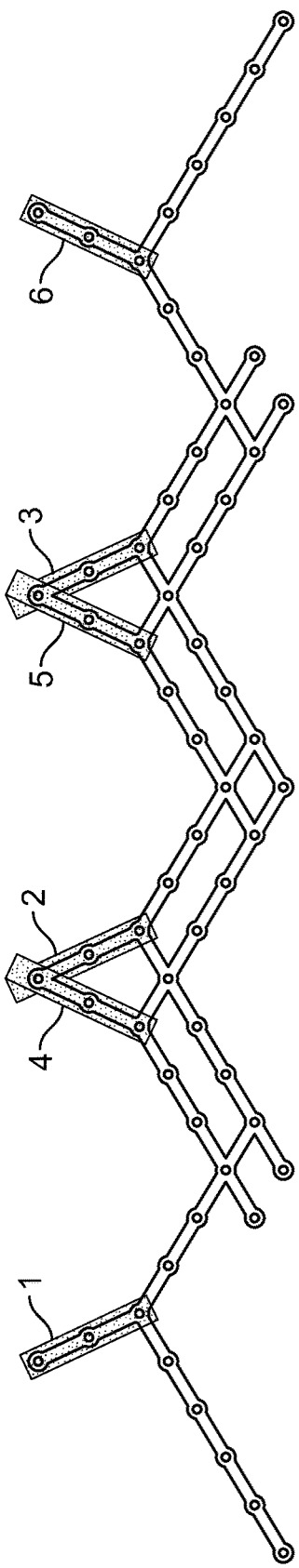
Figure 16L:
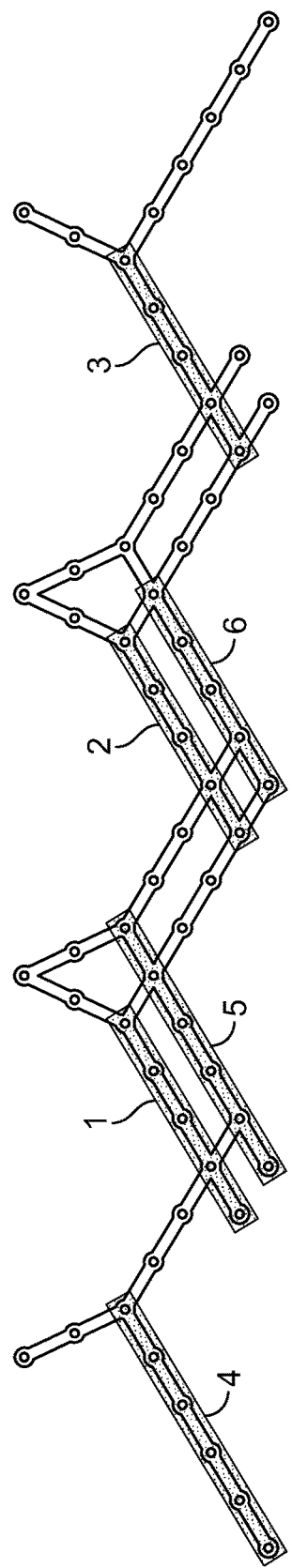
Figure 16M:
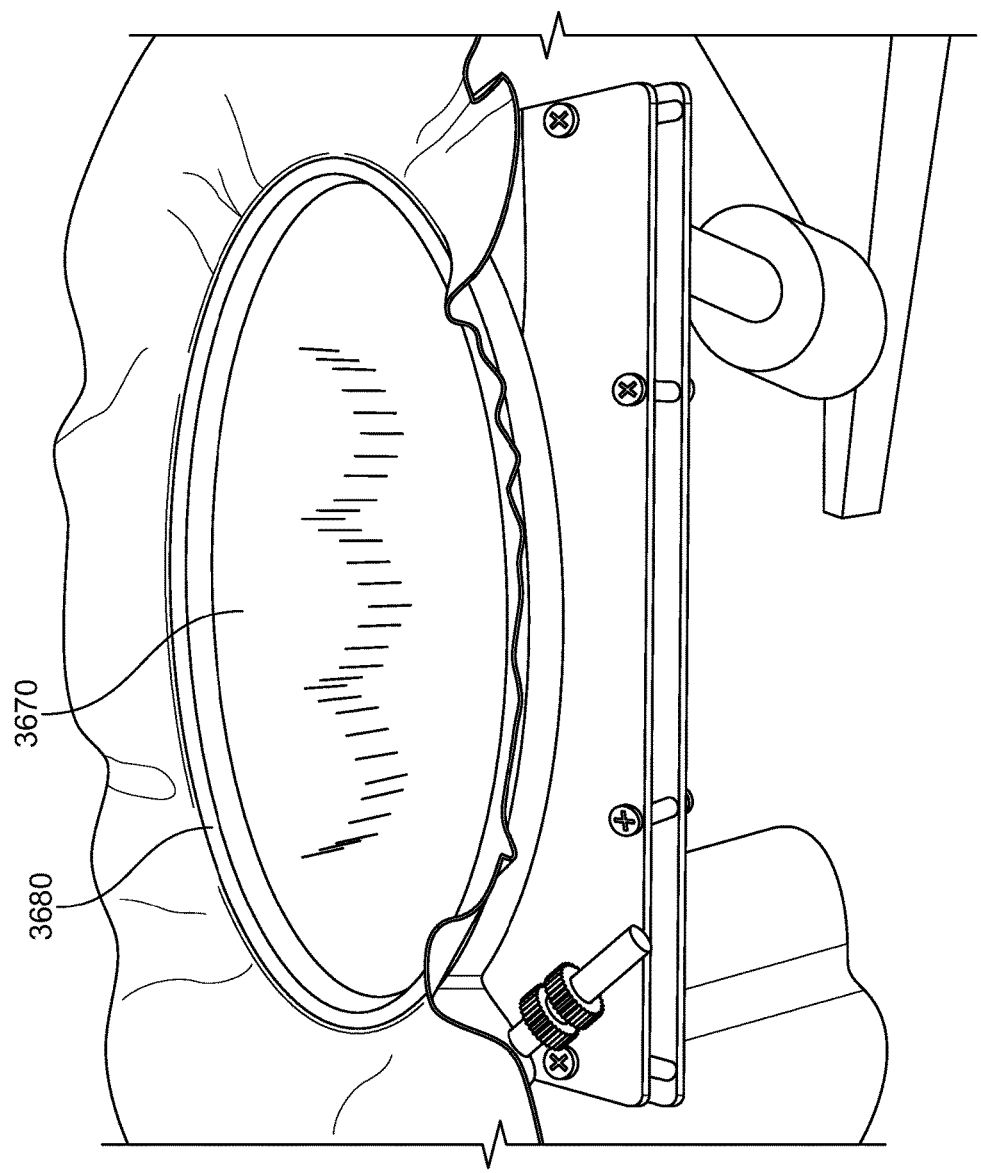
Figure 16N:
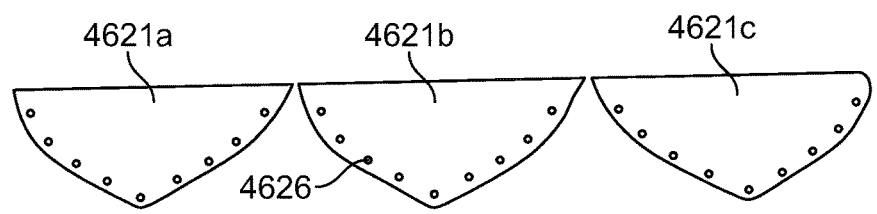
Figure 16O:
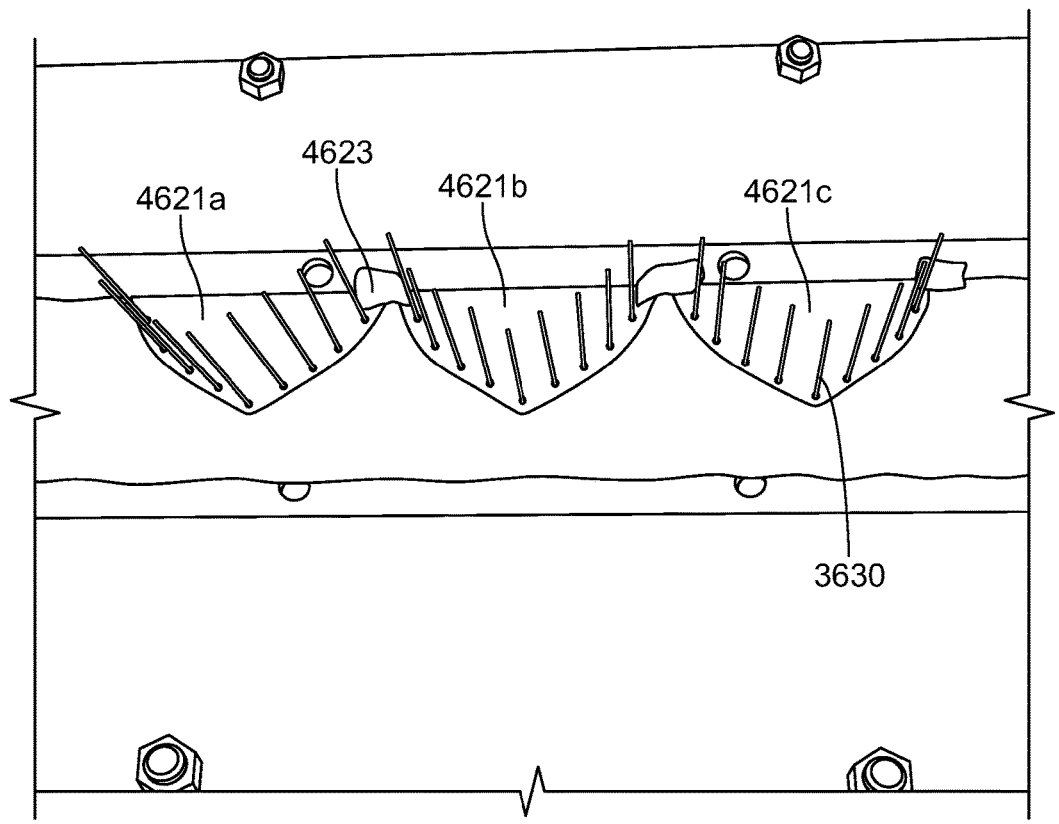
Figure 16P:
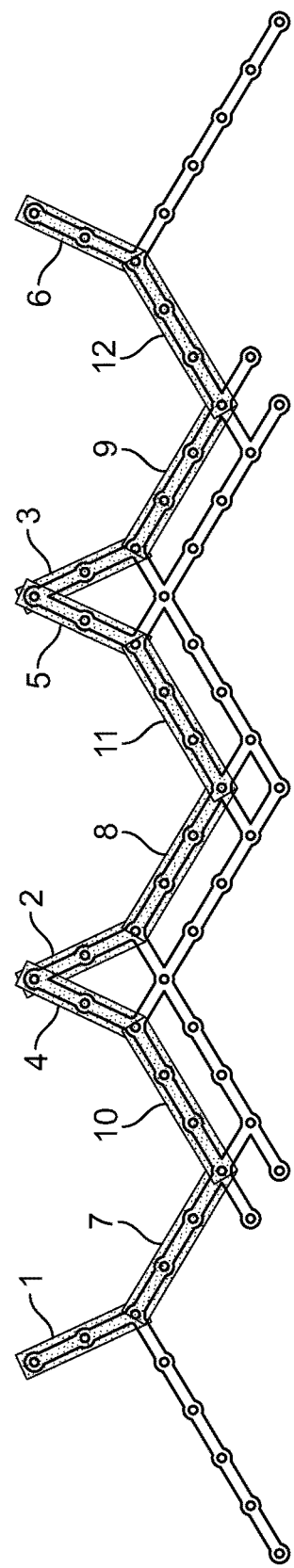
Figure 16Q:
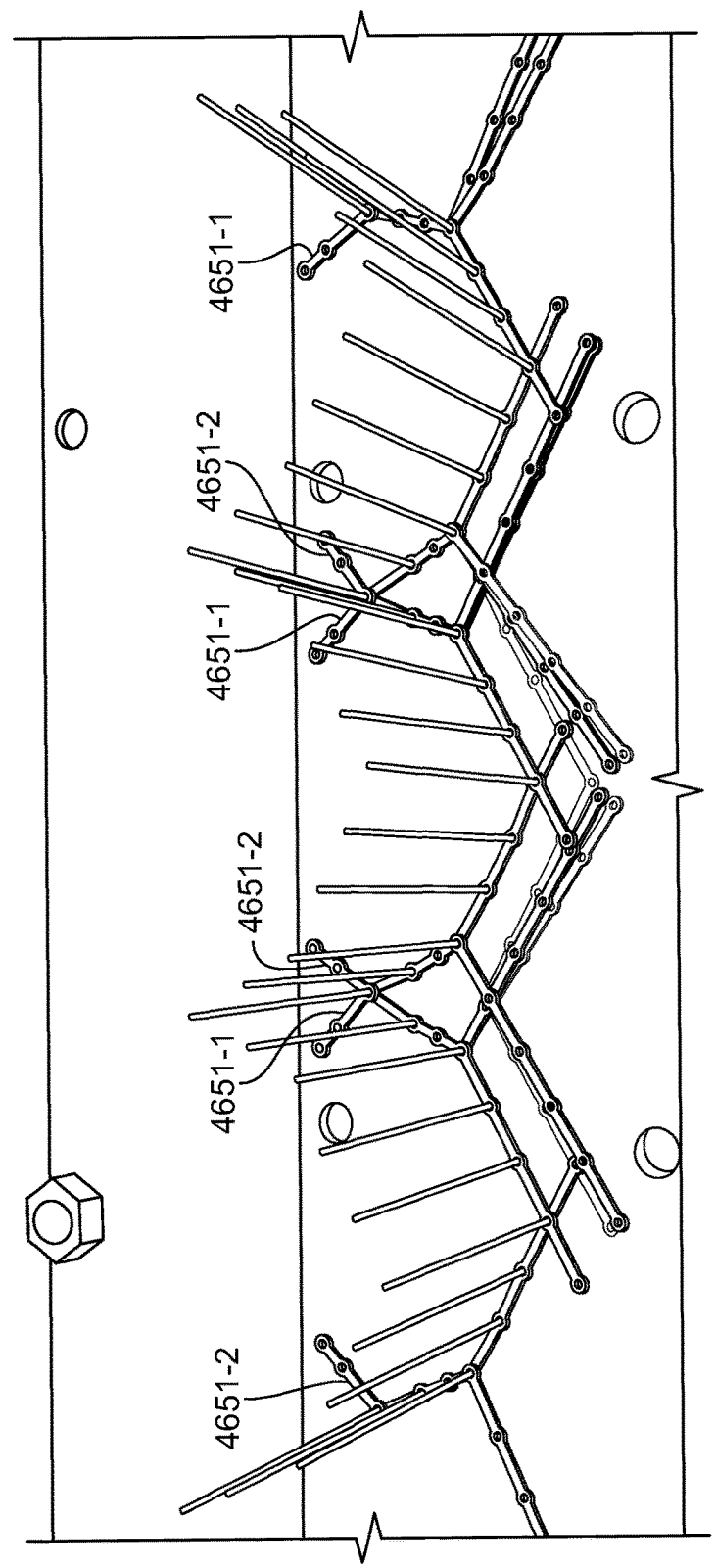
Figure 16R:
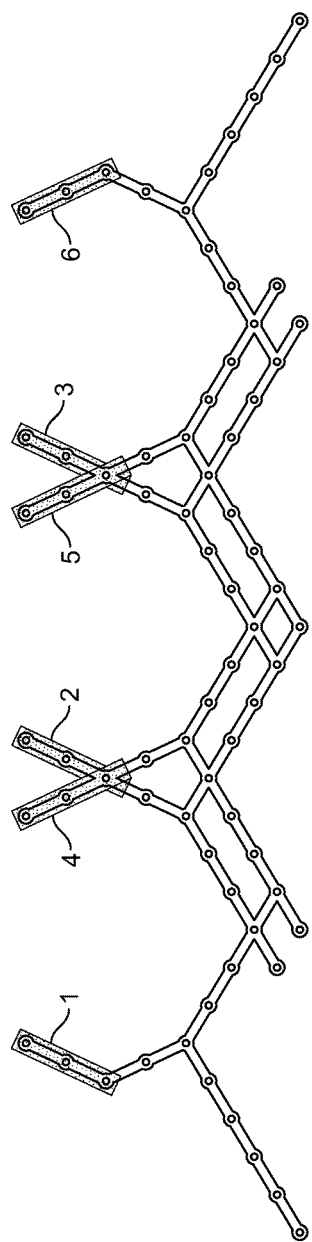
Figure 16T:
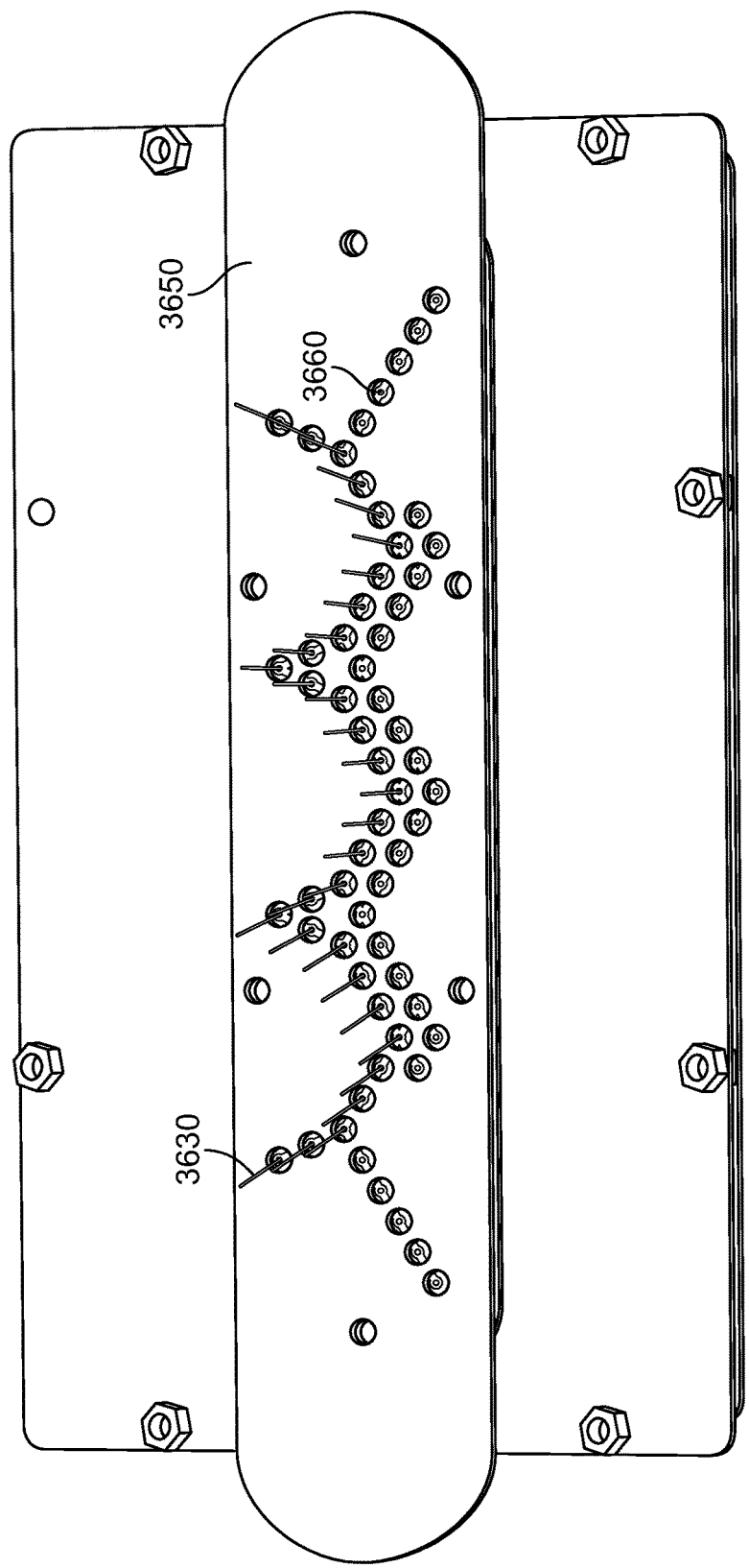
Figure 16U:
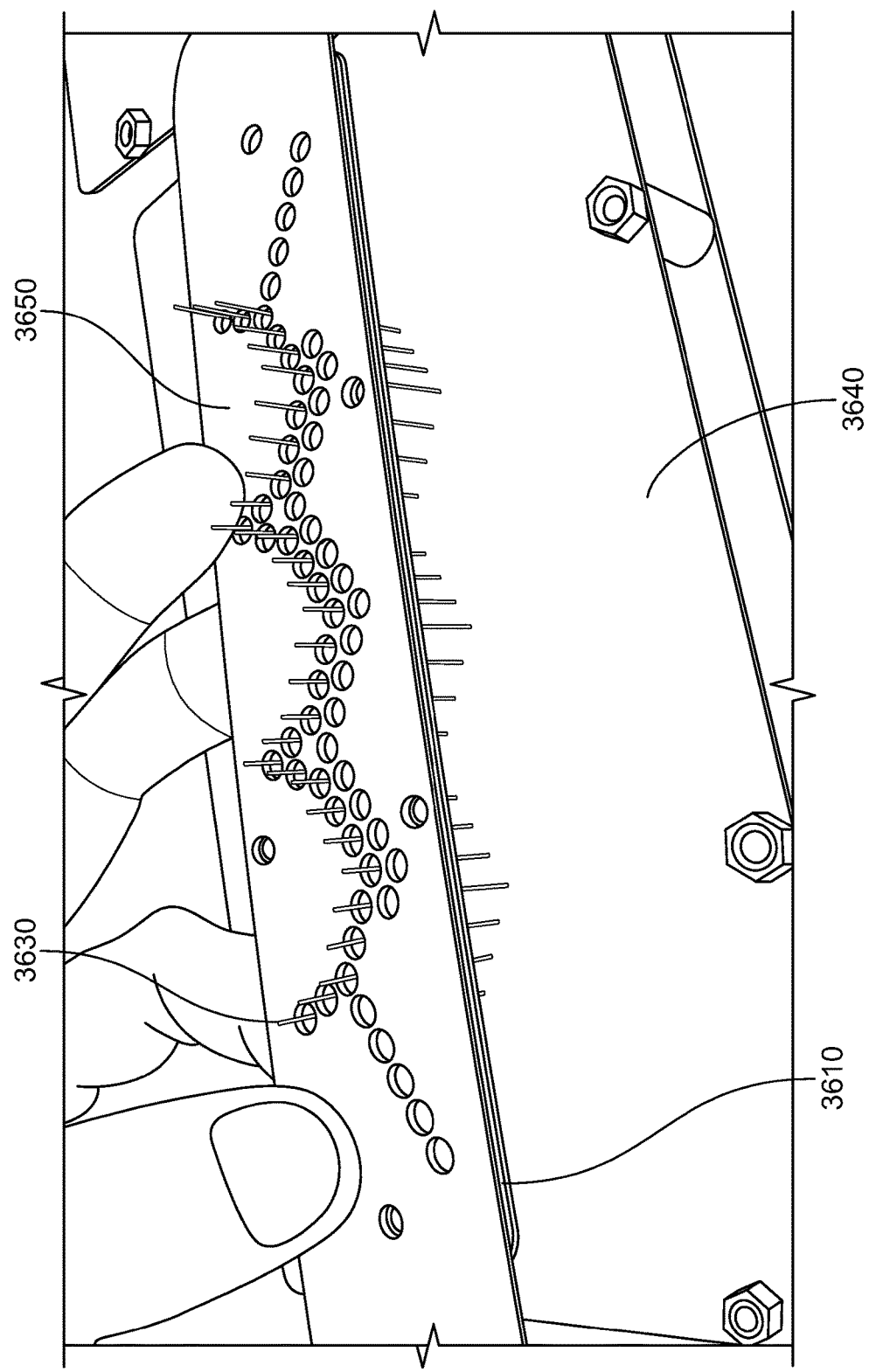
Figure 16V:
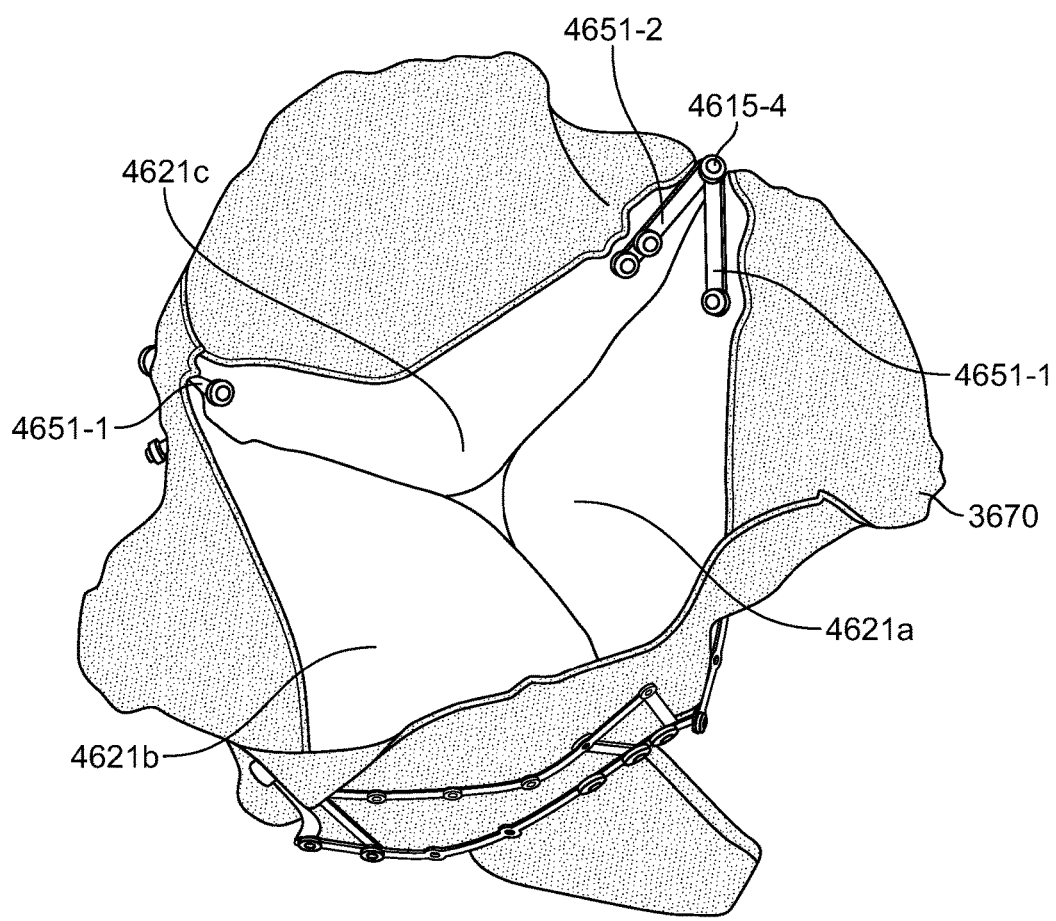
Figure 16W:
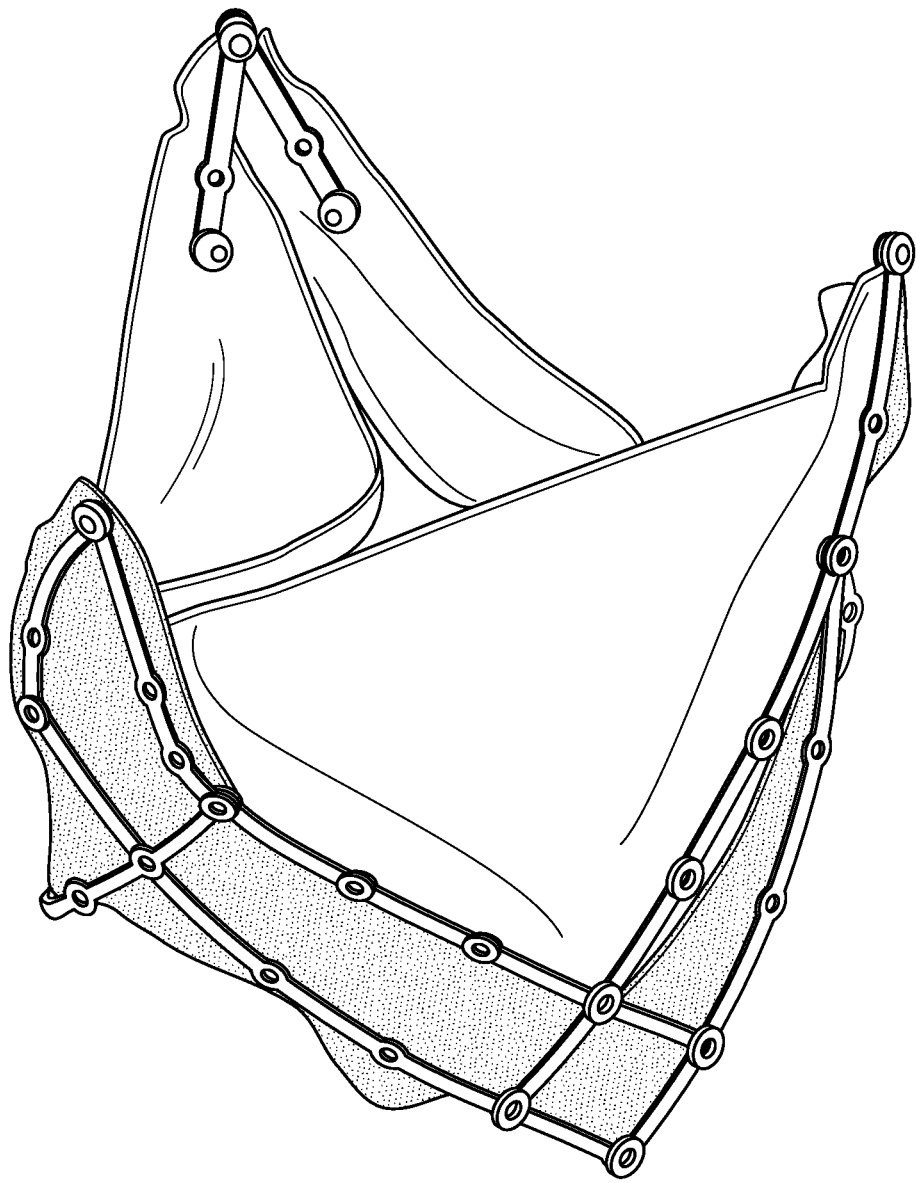

An example of the fabrication method as applied to the valve support structure is shown in FIGS. 16A-16W. FIG. 16A shows a perspective view of an alignment plate 3610. The alignment plate 3610 may be configured particularly for the fabrication of the support structure 4610. The alignment plate 3610 may comprise an opening 3620 corresponding to the location of each orifice 4613 of the strut members of support structure 4610 when in a flattened configuration. In other variations, the alignment plate 3610 may comprise fewer openings, however. For example, the alignment plate 3610 may comprise openings corresponding to the location of each articulated joint of the support structure 4610. In other variations, the alignment plate 3610 may comprise fewer openings, including no openings. The alignment plate 3610 may also comprise markings 3625, which may indicate the locations at which strut members will be placed onto the alignment plate 3610 during the fabrication process, although it should be understood that the markings 3625 are not required.

Alignment guides (e.g., pins 3630) may be placed through the openings 3620, as shown in FIG. 16B. As shown there, not all openings 3620 may have pins 3630 placed through them. Instead, the pins 3630 may be placed through openings 3620 on the distal side of the support structure, through the openings 3620 corresponding to the configuration of orifices 4613 of the commissure strut members 4619 of the support structure 4619 and the orifices 4613 of the longitudinal strut members 4611 forming a contiguous line of openings with those of the corresponding to the commissure strut members. In other variations, pins 3630 may be placed into more or all of the openings 3620 of the plate 3610. For example, pins 3630 may be placed through each opening 3620 of the plate 3610 corresponding to the location of articulated joints of support structure 4610. A schematic of the flattened chain and openings is shown in FIG. 16C, with the openings through which pins may be placed shaded. In other variations, pins 3630 may be placed into fewer openings 3620 of the plate 3610, including no openings. It should also be appreciated that in some variations, the alignment guides may be attached or integral to the alignment plate. For example, the alignment plate may not comprise openings, but may instead comprise alignment guides permanently extending from the same locations at which alignment guides could be placed through openings in the alignment plate described above.

Figure 16X:
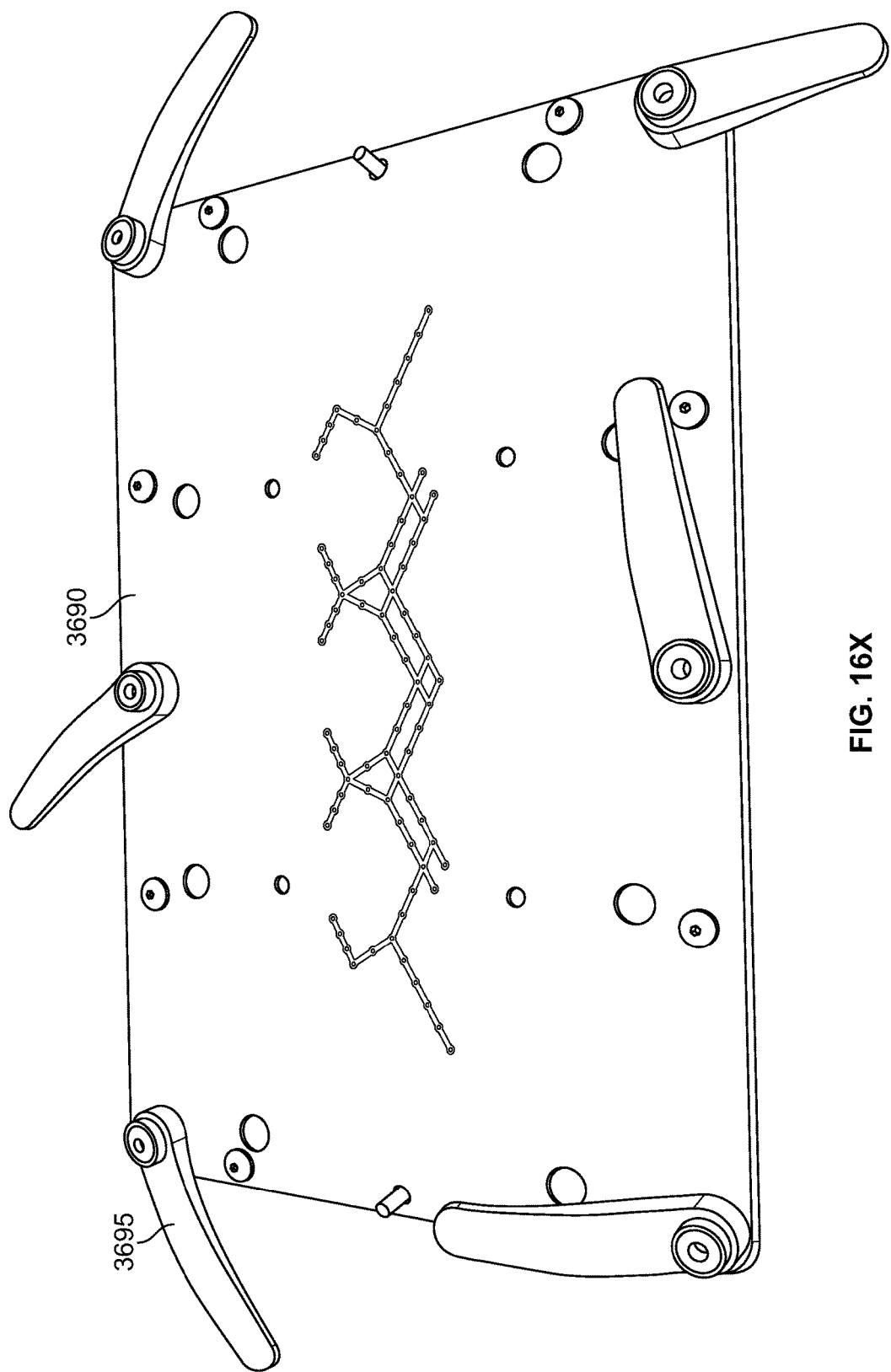

The alignment plate 3610 with loaded pins 3630 may be placed on top of a base frame 3640 and clamped in place, as shown in FIGS. 16D-16F. The base frame 3640 may comprise a top layer 3640-1 and a bottom later 3640-2. In some variations, the base frame may comprise a component or components to help secure the alignment plate in place. Such a variation of a base frame 3690 is shown in FIG. 16X. In the variation shown there, the base frame 3690 may comprise rotating clamps 3695. The rotating clamps 3695 may be rotated over the alignment plate 3610 once it is placed on the base frame, which may hold the alignment plate 3610 in place.

Figure 17A:
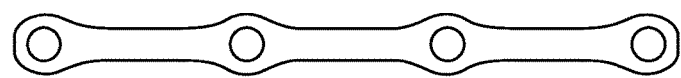
FIGS. 17A-17E illustrate configurations of the strut members used in the method of fabrication shown in FIGS. 16B-16W.
Figure 17B:
Figure 17C:
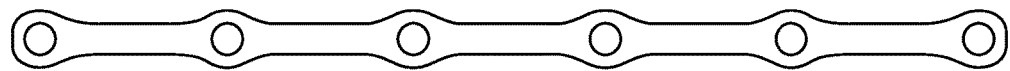
Figure 17D:
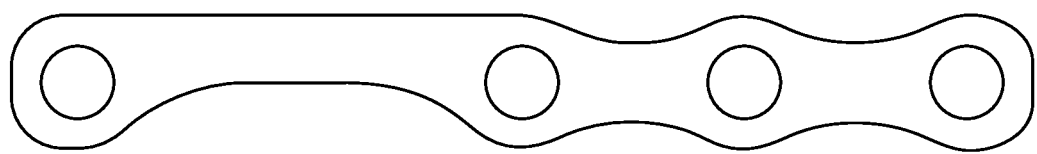
Figure 17E:
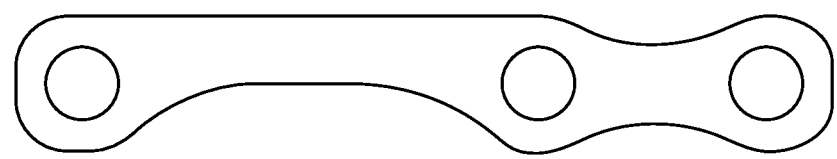
Figure 17F:
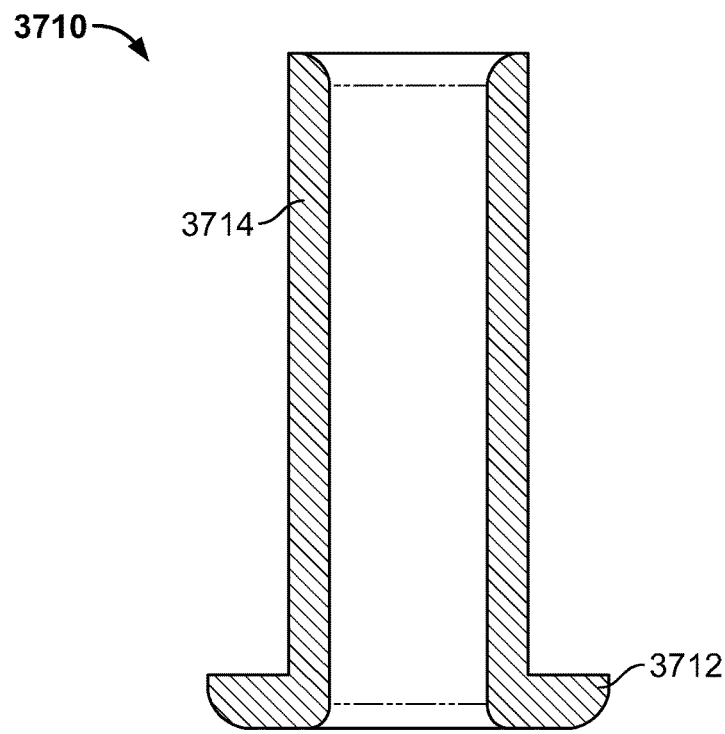
FIGS. 17F-17G illustrate a side cutaway view and a schematic side view, respectively, of an eyelet used in the method of fabrication before and after swaging, respectively.

Eyelets or rivets may then be loaded onto a subset of the pins 3630. The eyelets or rivets may be loaded onto the pins 3630 corresponding to locations of the articulated joints of support structure 4610. A side cut-away view of an example of an eyelet 3710 is shown in FIG. 17F. As shown, the eyelets or rivets may comprise a larger portion 3712 and a smaller portion 3714, where the larger portion 3712 of the eyelet or rivet (i.e., the flange) is larger in at least one cross-sectional dimension (i.e., perpendicular to longitudinal axis 3716) than the smaller portion 3714 of the eyelets or rivets. The eyelet or rivet may be loaded onto the pins such that the eyelet or rivet flange resides against to the plate 3610, and the smaller portion 3714 faces upwards, with the longitudinal axis 3716 perpendicular to the alignment plate 3610. The dimensions of the flange 3712 may be such that it may not pass through the openings 3620 of the plate 3610. The dimensions of the flange 3712 may also be such that it may not pass through the orifices 4613 of the strut members of the support structure 4610, described in more detail below, while the dimensions of the smaller portion 3717 may be such that it may pass through the orifices 4613 of the strut members of the support structure 4610. Thus, when the strut members are placed on the pins 3630, the narrower portion of the eyelets or rivets may pass through the orifices 4613, sandwiching the flange between the plate 3610 and the strut members and holding it in a configuration where the longitudinal axis 3716 is perpendicular to the alignment plate 3610. The eyelets or rivets may remain sandwiched between the plate 3610 and the strut members after the plates and strut members are removed from the pins 3630 (described below). The smaller portion 3714 may have a height (i.e., dimension along the longitudinal axis 3716) sufficient to pass fully through all of the components layered into the pins 3630 during the fabrication process (e.g., the strut members, skirt material, and valve leaflets, as described below) when the flange is sandwiched as described, such that the smaller portion 3714 may be swaged after the components are layered. It should be appreciated that in some variations, an eyelet or rivet may not be placed at each location corresponding to an articulating joint of the support structure. For example, no eyelet or rivet may be placed at articulated joints at which the support structure may be intended to be connected to another support structure (e.g., at articulated joints at which support structure 4610 is intended to be connected to an endoluminal support structure, such as support structure 3810 or 3910).

A subset of the longitudinal strut members 4611 may then be placed on the pins 3630, as shown in FIG. 16G. This subset may correspond to the outermost set of strut members of support structure 4610. A schematic of the flattened chain and openings is shown in FIG. 16H, with the strut members placed onto the shaded areas. The numbers indicate the order in which the strut members may be placed onto the pins. The longitudinal strut members 4611 may be mounted on the pins 3630 by placing the pins 3630 through orifices 4613 of the longitudinal strut members 4611. The smaller portion 3714 of the eyelets may fit through the orifices 4613, while the wider diameter portion of the eyelets may not. The subset of the longitudinal strut members 4611 mounted on the pins 3630 may comprise six longitudinal strut members 4611. The longitudinal strut members mounted on the pins 3630 in this step may all be parallel to each other and may not overlap with each other. More specifically, the longitudinal strut members 4611 first mounted on the pins 3630 may comprise the three outer longitudinal strut members 4611-2 and the three outer longitudinal strut members 4611-4. The three outer longitudinal strut members 4611-4 may be first placed on the pins 3630. While the variation shown in FIG. 16H indicates that the three outer longitudinal strut members 4611-4 may be placed in order from left to right, in other variations, they may be placed in any other order, such as but not limited to right to left. The outer longitudinal strut members 4611-2 may then be placed onto the pins 3630. While the variation shown in FIG. 16H indicates that the three outer longitudinal strut members 4611-4 may be placed in order from left to right, in other variations, they may be placed in any other order, such as but not limited to right to left. The outer longitudinal strut members 4611-2 may be placed onto the pins 3630 in a double layer (i.e., a pair of struts sitting on top of each other), as opposed to the single layer of outer longitudinal strut members 4611-4. The double layer may provide greater flexibility to these areas of the support structure, allowing the support structure to flex to mimic a PERIMOUNT open surgical valve. In so placing the longitudinal strut members 4611 on the pins 3630 as described, a pin may be placed through each orifice 4613 of the longitudinal strut members 4611-2 and 4611-4. In other variations a pin may be placed through fewer than each orifice of the longitudinal strut members. In some variations, the longitudinal strut members 4611-4 may have a thickness of 0.008, and the longitudinal strut members 4611-2 may individually have a thickness of 0.005. One configuration of longitudinal strut members 4611-4 is shown in more detail in FIG. 17B. One configuration of longitudinal strut members 4611-2 is shown in more detail in FIG. 17C.

The commissure strut members 4619 may then be placed on the pins 3630, as shown in FIG. 16I. A schematic of the flattened chain and openings is shown in FIG. 16J, with the strut members placed onto the shaded areas. The numbers indicate the order in which the strut members may be placed onto the pins. More specifically, the three commissure strut members 4619-2 may be first placed on the pins 3630, which may be done from left to right as indicated. The three commissure strut members 4619-1 may then be placed on the pins 3630, which also may be done from left to right. However, it should be appreciated that both sets of the commissure strut members 4619 may be placed onto the pins in other orders, such as but not limited to right to left. A pin may be placed through each orifice 4613 of the commissure strut members 4619. In other variations a pin may be placed through fewer than each orifice of the longitudinal strut members. All of the commissure strut members 4619 may have a thickness of 0.005 and may be placed onto the pins 3630 in a single layer. One configuration of the commissure strut members 4619 is shown in more detail in FIG. 17D.

The remaining longitudinal strut members 4611 of the support structure 4610 may then be placed on the pins 3630, as shown in FIG. 16K. A schematic of the flattened chain and openings is shown in FIG. 16L, with the strut members placed onto the shaded areas. The numbers indicate the order in which the strut members may be placed onto the pins. These remaining longitudinal strut members 4611 may comprise six parallel longitudinal strut members 4611—more specifically, three inner longitudinal strut members 4611-1 and three inner longitudinal strut members 4611-3. The three inner longitudinal strut members 4611-1 may be first placed on the pins 3630. While the variation shown in FIG. 16L indicates that the three inner longitudinal strut members 4611-1 may be placed in order from left to right, in other variations, they may be placed in any other order, such as but not limited to right to left. The three inner longitudinal strut members 4611-3 may then be placed into the pins 3630. While the variation shown in FIG. 16L indicates that the three inner longitudinal strut members 4611-3 may be placed in order from left to right, in other variations, they may be placed in any other order, such as but not limited to right to left. The three inner longitudinal strut members 4611-3 may be placed onto the pins 3630 in a double layer (i.e., a pair of struts sitting on top of each other), as opposed to the single layer of outer longitudinal strut members 4611-1. The double layer may provide greater flexibility to these areas of the support structure, allowing the support structure to flex to mimic a PERIMOUNT open surgical valve. In contrast to the placement of outer longitudinal strut members 4611-2, 4611-4, a pin may not be placed through each orifice of the inner longitudinal strut members 4611-1, 4611-3. A pin may only be placed through the distal-most orifice 4613 of each inner longitudinal strut member 4611-1, 4611-3, at the location corresponding to the articulated joints 4615-2 and 4615-3. In some variations, the longitudinal strut members 4611-1 may have a thickness of 0.008, and the longitudinal strut members 4611-3 may have a thickness of 0.005. One configuration of the longitudinal strut members 4611-1 is shown in more detail in FIG. 17B. One configuration of the longitudinal strut members 4611-3 is shown in more detail in FIG. 17C.

The skirt material 3670 may then be placed over the pins 3630, as shown in FIG. 16M. In some variations, the skirt material 3670 may comprise Dacron. Before being lowered onto the pins 3630, the skirt material 3670 may be stretched taut using an embroidery-hoop like device 3680 that may sandwich the skirt material 3670 between two hoops while being placed over the pins 3630. In variations in which the skirt material is woven, the fibers may be oriented diagonally relative to the horizontal plane of the frame (i.e., along the bias). Orienting the skirt material in this way may allow the material to stretch to accommodate the adjustable diameter of the assembled support structure. In some variations in which the material is woven, the pins 3630 may fit through the natural openings between the woven fibers. In other variations, the skirt material may comprise openings configured to receive the pins 3630 through them. In yet other variations, the pins 3630 may be configured to pierce or cut the skirt material (e.g., by comprising a sharpened or pointed end) in order to allow the pins 3630 to be placed through the skirt material.

Three valve leaflets 4621a, 4621b, 4621c, shown in FIG. 16N, may then be placed onto the pins 3630, as shown in FIG. 16O. The valve leaflets may comprise a substantially rounded triangular shape, as shown. In some variations, the valve leaflets may comprise tabs 4623 on either side to assist with placement of the leaflets onto the pins. In some variations, the valve leaflets 4621 may comprise openings 4626 configured to receive the pins 3630 through them. In other variations, the valve leaflets 4621 may not comprise openings, but the pins 3630 may be configured to pierce or cut the valve leaflets 4621 (e.g., by comprising a sharpened or pointed end) in order to allow the pins 3630 to be placed through the valve leaflets 4621. Once placed onto the pins 3630, the valve leaflets may sit flat against the skirt material, as shown in FIG. 16O.

More strut members may then be placed on the pins 3630 over the valve leaflets. The strut members may be placed in locations corresponding to the edges of the valve leaflets 4621, which may also correspond to the locations of the commissure strut members and a subset of longitudinal strut members of support structure 4610. The strut members may thus sandwich the edges of the valve leaflets between them and the previously placed strut members (with the skirt material intervening). A schematic of the flattened chain and openings is shown in FIG. 16P, with the strut members placed onto the shaded areas. The numbers indicate the order in which the strut members may be placed onto the pins. As indicated, three strut members corresponding to the location of commissure strut members 4619-2 may first be placed on the pins 3630.

While the variation shown in FIG. 16P indicates that the three outer longitudinal strut members 4619-2 may be placed in order from left to right, in other variations, they may be placed in any other order, such as but not limited to right to left. Three strut members corresponding to commissure strut members 4619-1 may then be placed onto the pins 3630, which may also be done from left to right, or in other variations may be done in other orders, such as but not limited to right to left. Three strut members corresponding to outer longitudinal strut members 4611-4 may then be placed onto the pins 3630, which may also be done from left to right, or in other variations may be done in other order, such as but not limited to right to left. Three strut members corresponding to inner longitudinal strut members 4611-1 may then be placed onto the pins 3630 in a single layer, which may also be done from left to right, or in other variations may be done in other order, such as but not limited to right to left. In so placing the strut members onto the pins 3630 as described, a pin may be placed through each orifice 4613 of the struts corresponding to the longitudinal strut members 4611 and commissure strut members 4619. In other variations a pin may be placed through fewer than each orifice of the longitudinal strut members. These struts may have a thickness of 0.005. One configuration of the strut members corresponding to commissure strut members 4619-1, 4619-2 is shown in more detail in FIG. 17D. One configuration of the strut members corresponding to longitudinal strut members 4611-1, 4611-4 is shown in more detail in FIG. 17A.

Coaptation strut members 4651 may then be placed on the pins 3630, as shown in FIG. 16Q. A schematic of the flattened chain and openings is shown in FIG. 16R, with the strut members placed onto the shaded areas. The numbers indicate the order in which the strut members may be placed onto the pins. It should be noted that the skirt material and valve leaflets are not shown in FIG. 16Q in order to reveal the underlying strut members. The three coaptation strut members 4651-2 may be first placed on the pins 3630, which may be done from left to right as indicated. Three coaptation strut members 4651-1 may then be placed on the pins 3630, which also may be done from left to right. The coaptation strut members 4651 may have a thickness of 0.005 and may be placed in a single layer. The coaptation strut members 4651 may comprise a wire, which in some variations may comprise a shape memory material, such as Nitinol. One configuration of the coaptation strut members 4651-1, 4651-2 is shown in more detail in FIG. 17E. However, it should be appreciated that the coaptation strut members 4651 may have other configurations; for example, they may have a longer length, which may allow them to follow the entire length of the valve leaflet when the coaptation strut members 4651 are rotated over the leaflets, as described in more detail below. Additionally or alternatively, the coaptation strut members 4651 may comprise a single element or multiple elements. One configuration of the coaptation strut members 4651-1, 4651-2 is shown in more detail in FIG. 17E. A pin may be placed only through one orifice 4613 of each of the coaptation strut members 4651; this may allow the coaptation strut members 4651 to be rotated during the fabrication process, as described in more detail below. More specifically, each pair of coaptation strut members 4651-1, 4651-2 may be placed over the pin corresponding to the location of the articulated joint 4615-4 of support structure 4610.

A cover plate 3650 may then be placed over the pins 3630, as shown in FIGS. 16S-16T. The cover plate may but need not comprise openings 3660 corresponding to the location of each orifice 4613 of the strut members of support structure 4610. It should be appreciated that the cover plate may comprise fewer openings; for example, the cover plate may comprise openings only corresponding to the placement of pins 3630, as described above, or openings only corresponding to the placement of eyelets or rivets, as described above. Once placed over the pins 3630, each pin 3630 may go through an opening 3660 of the cover plate 3650 in variations having an opening corresponding to each pin. The openings 3660 of the cover plate 3650 may be larger than the openings 3620 of the alignment plate to allow access for a swaging tool, as described in more detail below.

The alignment plate 3610 and the cover plate 3650, and the eyelets, strut members, skirt material, and valve leaflets located in between the two plates, may then be removed from the base frame 3640 by sliding them up and off of the pins 3630, as shown in FIG. 16U. Compressive force may be applied to the alignment plate 3610 and the cover plate 3650 while removing them from the pins 3630, which may hold the eyelets, strut members, skirt material, and valve leaflets in place as and after they are removed from the pins 3630.

Figure 17G:
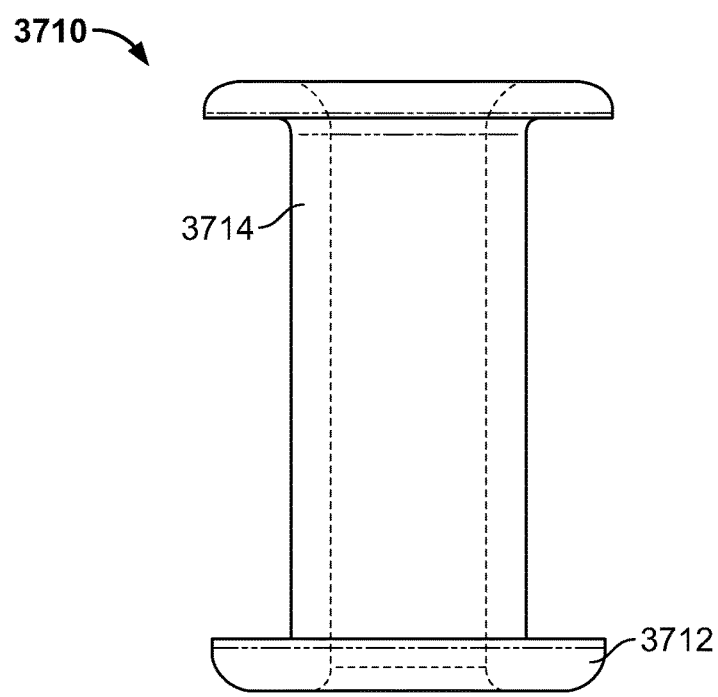

The eyelets may then be swaged. In some variations, the swaging may be done using a manual swaging tool. In other variations, a benchtop swaging instrument may be used. The openings 3660 in the cover plate 3650 may be large enough to allow the swaging tool to access each eyelet. FIG. 17G illustrates a side view of an eyelet after being swaged. As shown, after being swaged, the end of the smaller portion 3714 may be bent outward. After being bent outward, at least one dimension of the smaller portion 3714 of the eyelet or rivet may be large enough that it may not pass through the openings 4613 of the strut members of the support structure 4610. The layered strut members, valve leaflets, and skirt material may thus be held between the flange 3712 of the eyelet and the outwardly bent end of the smaller portion 3714, securing them together. However, the dimensions of the smaller portion 3714 of the eyelet or rivet once bent outwardly may be small enough to fit through the openings 3660 of the cover plate 3650, such that the cover plate 3650 may be removed from the layered components after swaging.

After the eyelets or rivets are swaged to hold the layered strut members, valve leaflets, and skirt material together, the alignment plate 3610 and cover plate 3650 may be removed. The flattened chain may then be shaped into the final shape of the support structure 4610, i.e., into a tubular shape. The ends of the flattened chain may be interlinked to hold the flattened chain into the final shape, e.g., by securing the ends together with eyelets, which may then be swaged.

The coaptation strut members 4651 may then be moved from their initial position, as shown in FIG. 16Q, into a final position, shown in FIG. 16V. In the initial position, the coaptation strut members 4651 may extend in part distally to the articulated joint 4615-4. In the final position, the coaptation strut member 4651 may extend in part proximally to the articulated joint 4615-4. The coapation strut members 4651 may be rotated proximally and away from each other about the articulated joint 4615-4 to be moved from the initial position to the final position. As the coaptation strut members 4651 are rotated proximally and away from each other, they may come into contact with the valve leaflets 4621a, 4621b, 4621c and may bend the outer distal ends of each leaflet proximally, biasing each valve leaflet 4621, 4621b, 4621c into a closed position, as shown in FIG. 16V. In some variations, the free ends of the coaptation strut members may then be secured to the underlying commissure struts by eyelets. The eyelets may be swaged using a hand tool. This may sandwich the valve material between the commissure strut members 4619 and the coaptation strut members 4651 biased in the closed position. It should be appreciated, however, that the free ends of the coaptation strut members need not be secured to the underlying commissure strut members by eyelets. In some variations, the free ends of the coaptation strut members may be held in place via other methods, such as but not limited to friction.

The excess skirt material 3670 (i.e., the skirt material extending distally to the support structure 4610) may then be trimmed off, resulting in the support structure with valve and skirt shown in FIG. 16W.

It should be appreciated that the method of fabrication may be performed in the reverse order, beginning with coaptation strut members 4651 and ending with the outermost struts. It should also be appreciated that certain steps may be performed in different orders; for example, each group of strut members placed onto the pins 3630 may be placed onto the pins from right to left.

A similar method may also be used to fabricate an endoluminal support structure, such as the support structure 3910 of FIG. 5. Once fabricated, the valve support structure fabricated above may be connected to the endoluminal support structure, as described in more detail below. The endoluminal support structure may be fabricated with a skirt by sandwiching the skirt material between two sets of strut members. In some variations, the two sets of strut members may be the same, while in other variations, the two sets of strut members may be different. In one variation of the method, the support structure 3910 may be fabricated using an alignment plate 4410 such as the one shown in FIG. 18A. The alignment plate 4410 may comprise an opening 4420 corresponding to the location of each orifice 3913 of the strut members of support structure 3910 when in a flattened configuration. In other variations, the alignment plate 4410 may comprise fewer openings, however. For example, the alignment plate 4410 may comprise openings corresponding to the location of each articulated joint of the support structure 3910. In other variations, the alignment plate 4410 may comprise fewer openings, including no openings. The alignment plate 4410 may also comprise markings 4425, which may indicate the locations at which strut members will be placed onto the alignment plate 4410 during the fabrication process, although it should be understood that the markings 4425 are not required.

Figure 18A:
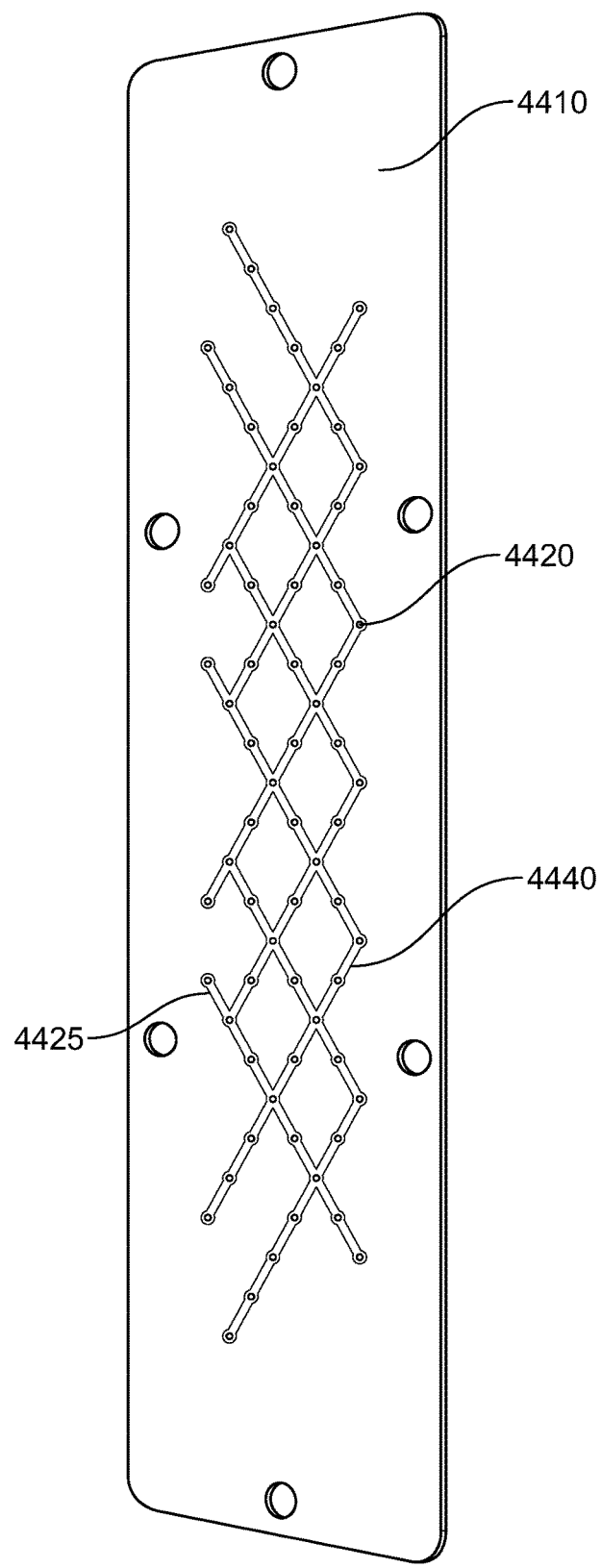
FIG. 18A is a top perspective view of a particular alignment plate.
Figure 18B:
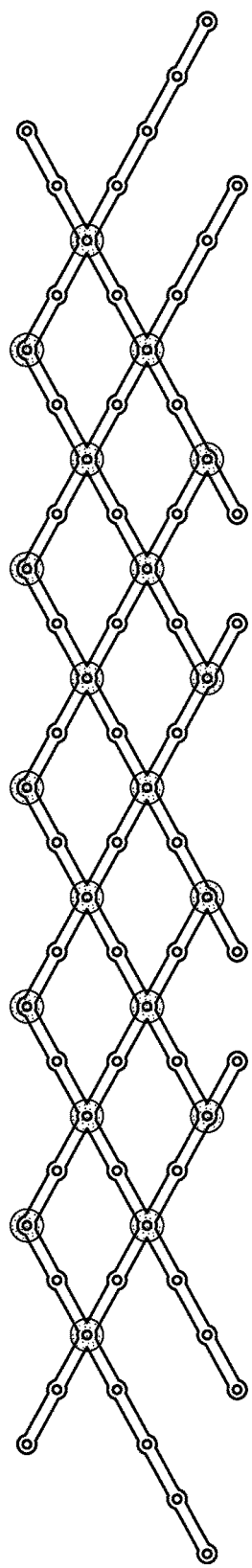
FIGS. 18B-18F illustrate schematic views of steps in a method of fabrication.

Alignment guides (e.g., pins) may be placed through the openings 4420. Not all openings 4420 may have pins placed through them. Instead, the pins may be placed through openings 4420 through the openings 4420 corresponding to the configuration of articulated joints of the support structure 3910. In other variations, pins may be placed into more or all of the openings 4420 of the plate 4410. For example, pins may be placed through each opening 4420 of the plate 4410. A schematic of the flattened chain and openings is shown in FIG. 18B, with the openings through which pins may be placed shaded. In other variations, pins may be placed into fewer openings 4420 of the plate 4410, including no openings. It should also be appreciated that in some variations, the alignment guides may be attached or integral to the alignment plate. For example, the alignment plate may not comprise openings, but may instead comprise alignment guides permanently extending from the same locations at which alignment guides could be placed through openings in the alignment plate described above.

The alignment plate 4410 with loaded pins may be placed on top of a base frame and clamped in place as described above with respect to the valve support structure above. The same or a different base plate may be used for alignment plate 4410.

Eyelets or rivets may then be loaded onto the pins. In variations in which the pin locations include ones that do not correspond to articulated joints of the support structure 3910, the eyelets or rivets may be loaded only onto pins corresponding to articulated joints of the support structure 3910. The eyelets may be the same or have similar features as described above with respect to FIGS. 17F-17G. It should be appreciated that in some variations, an eyelet or rivet may not be placed at each location corresponding to an articulating joint of the support structure. For example, no eyelet or rivet may be placed at articulated joints at which the support structure may be intended to be connected to another support structure (e.g., at articulated joints at which support structure 3910 is intended to be connected to valve support structure 4610).

Figure 18C:
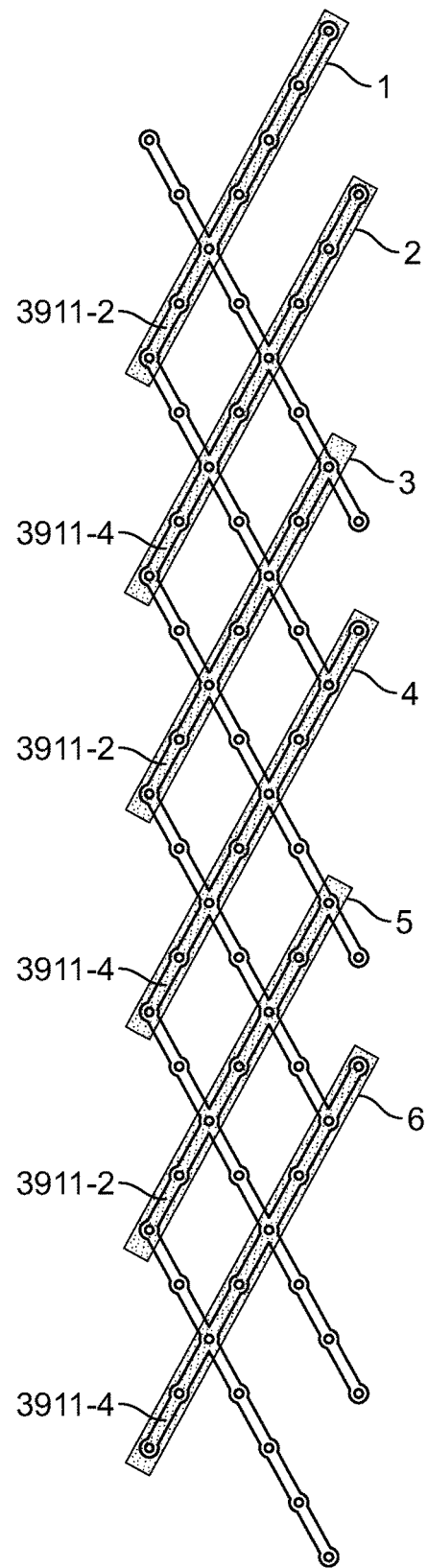

A subset of the strut members 3911 may then be placed on the pins. This subset may correspond to the outermost set of strut members of support structure 3910. A schematic of the flattened chain and openings is shown in FIG. 18C, with the strut members placed onto the shaded areas. The numbers 1 through 6 indicate the order in which the strut members may be placed onto the pins. The strut members 3911 may be mounted on the pins by placing the pins through orifices 3913 of the strut members 3911. The smaller portion of the eyelets may fit through the orifices 3913, while the wider diameter portion of the eyelets may not. The subset of the longitudinal strut members 3911 mounted on the pins may comprise the three strut members 3911-2 and the three strut members 3911-4, as described in more detail with respect to FIG. 5. The strut members mounted on the pins in this step may all be parallel to each other and may not overlap with each other. While the variation shown in FIG. 18C indicates that the strut members may be placed in order from left to right, in other variations, they may be placed in any other order, such as but not limited to right to left. In so placing the strut members 3911 on the pins as described, a pin may be placed through each orifice 3913 of the strut members 3911. In other variations a pin may be placed through fewer than each orifice of the longitudinal strut members.

Figure 18D:
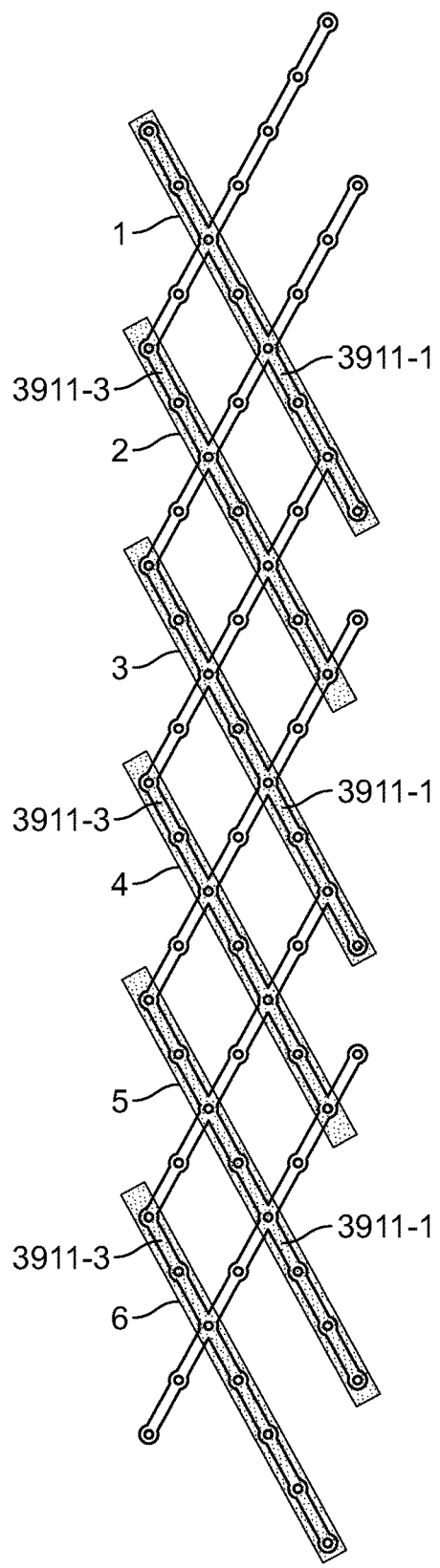

The remaining strut members 3911 of the support structure 3910 may then be placed on the pins. A schematic of the flattened chain and openings is shown in FIG. 18D, with the strut members placed onto the shaded areas. The numbers 1 through 6 indicate the order in which the strut members may be placed onto the pins. These remaining strut members 3911 may comprise six parallel strut members 3911—more specifically, the six innermost strut members of support structure 3910. This may include the three strut members 3911-1 and three strut members 3911-3. While the variation shown in FIG. 18D indicates that the strut members may be placed in order from left to right, in other variations, they may be placed in any other order, such as but not limited to right to left. In so placing the strut members 3911 on the pins as described, a pin may be placed through each orifice 3913 of the strut members 3911.

Skirt material may then be placed over the pins. In some variations, the skirt material may comprise Dacron. Before being lowered onto the pins, the skirt material may be stretched taut using an embroidery-hoop like device that may sandwich the skirt material between two hoops while being placed over the pins, as described in more detail above with respect to FIG. 16M. In some variations in which the material is woven, the pins may fit through the natural openings between the woven fibers. In other variations, the skirt material may comprise openings configured to receive the pins through them. In yet other variations, the pins may be configured to pierce or cut the skirt material (e.g., by comprising a sharpened or pointed end) in order to allow the pins to be placed through the skirt material.

Figure 18E:
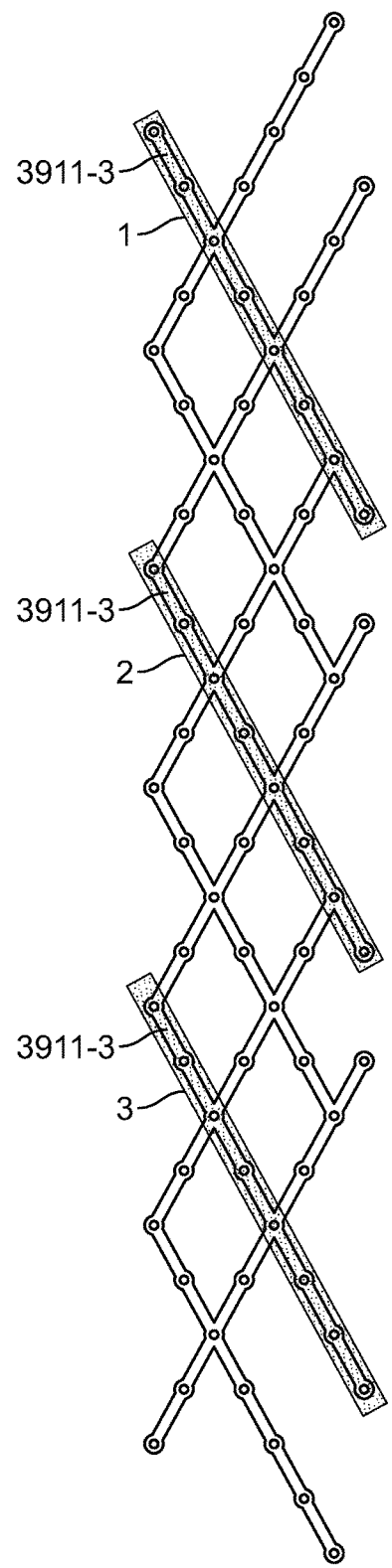
Figure 18F:
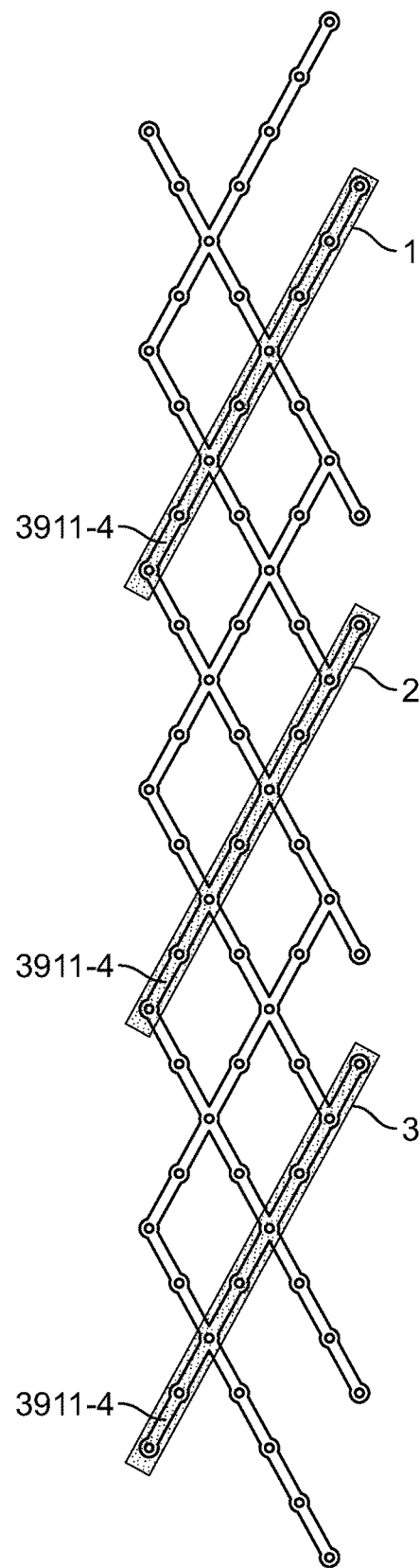

More strut members may then be placed on the pins over the skirt material. The strut members may sandwich the skirt material between them and the previously placed strut members. These strut members may in some variations be at the same locations as the strut members located below the skirt material, but in other variations may be located at other locations. In variations in which these strut members overlap with each other, the strut members may be placed in a particular order over the skirt material. For example, in some variations, six strut members may be placed over the skirt material at locations that correspond to a subset of the locations of the strut members located below the skirt material. A schematic of this example is shown in FIG. 18E, with three strut members corresponding to the locations of strut members 3911-3 first placed onto the pins, shown by the shaded areas. A second group of three strut member corresponding to the locations of strut members 3911-4 may then be placed onto the pins, as indicated in FIG. 36F. The numbers 1 through 3 indicate the order in which the strut members may be placed onto the pins. While the variation shown in FIG. 18E-18F indicates that the strut members may be placed in order from left to right, in other variations, they may be placed in any other order, such as but not limited to right to left. It should also be appreciated that the skirt material may be sandwiched between the strut members shown in FIGS. 18C-18D and strut members having different configurations than the strut members shown in FIGS. 18E-18F. For example, the strut members placed over the skirt material may comprise strut members corresponding to strut members 3911-1 and 3911-2 of support structure 3910.

A cover plate may then be placed over the pins. The cover plate may but need not comprise openings corresponding to the location of each orifice 3913 of the strut members of support structure 3910. It should be appreciated that the cover plate may comprise fewer openings; for example, the cover plate may comprise openings only corresponding to the placement of pins, as described above, or openings only corresponding to the placement of eyelets or rivets, as described above. Once placed over the pins, each pin may go through an opening of the cover plate in variations having an opening corresponding to each pin. The openings of the cover plate may be larger than the openings of the alignment plate to allow access for a swaging tool, as described in more detail below.

The alignment plate 4410 and the cover plate, and the eyelets, strut members, and skirt material located in between the two plates may then be removed from the base frame by sliding them up and off of the pins. Compressive force may be applied to the alignment plate 4410 and the cover plate while removing them from the pins, which may hold the eyelets, strut members, skirt material, and valve leaflets in place as and after they are removed from the pins. The eyelets may then be swaged, as described in more detail with respect to support structure 3610 above. After the eyelets or rivets are swaged to hold the layered strut members and skirt material together, the alignment plate 4410 and cover plate may be removed. The flattened chain may then be shaped into the final shape of the support structure 3910, i.e., into a tubular shape. The ends of the flattened chain may be interlinked to hold the flattened chain into the final shape, e.g., by securing the ends together with eyelets, which may then be swaged. Once rolled into the final shape, an actuator may in some instances be attached to the support structure, in the manner described in more detail above. In other variations, an actuator may be attached to the flattened chain before it is shaped into the final shape.

It should be appreciated that the method of fabrication may be performed in the reverse order, beginning with the innermost strut members and ending with the outermost strut members. It should also be appreciated that certain steps may be performed in different orders; for example, each group of strut members placed onto the pins may be placed onto the pins from right to left.

Once fabricated, the valve support structure fabricated above may be connected to the endoluminal support structure. It should also be appreciated that in some variations of the methods described herein, the valve support structure and endoluminal support structure may be fabricated simultaneously—that is, as a single flattened chain, which may then be rolled into a tubular structure. It should also be appreciated that the support structures described herein may be fabricated in a similar method using three-dimensional printing. In some variations, three-dimensional printing may be used to print the flattened chain of components described herein, either from outermost to innermost, or from innermost to outermost, and then the chain may be shaped into a tubular structure. In other variations, three-dimensional printing may be used to print the strut members of the flattened chain, while the skirt and/or valve leaflets may be added separately during the printing process. In yet other variations, three-dimensional printing may be used to print the device in its final tubular form.

Figure 19A:
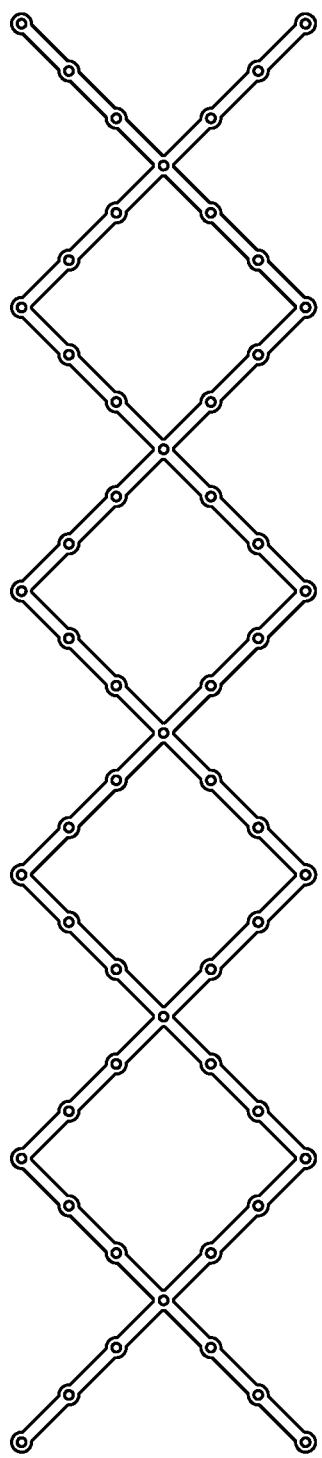
FIG. 19A illustrates a schematic view of a support structure in a flattened configuration.

Similar methods may be used to fabricate other support structures. For example, a similar fabrication method may be used to fabricate a support structure such as the one shown schematically in a flattened configuration FIG. 19A. To fabricate this support structure, a similar alignment plate may be used, but the openings and markings may correspond to those shown in FIG. 19A. That is, the alignment plate may comprise an opening corresponding to the location of each orifice of the strut members of support structure when in a flattened configuration. In other variations, the alignment plate may comprise fewer openings, however. For example, the alignment plate may comprise openings corresponding to the location of each articulated joint of the support structure. In other variations, the alignment plate may comprise fewer openings, including no openings. It should be understood that the markings on the alignment plate are not required.

Figure 19B:
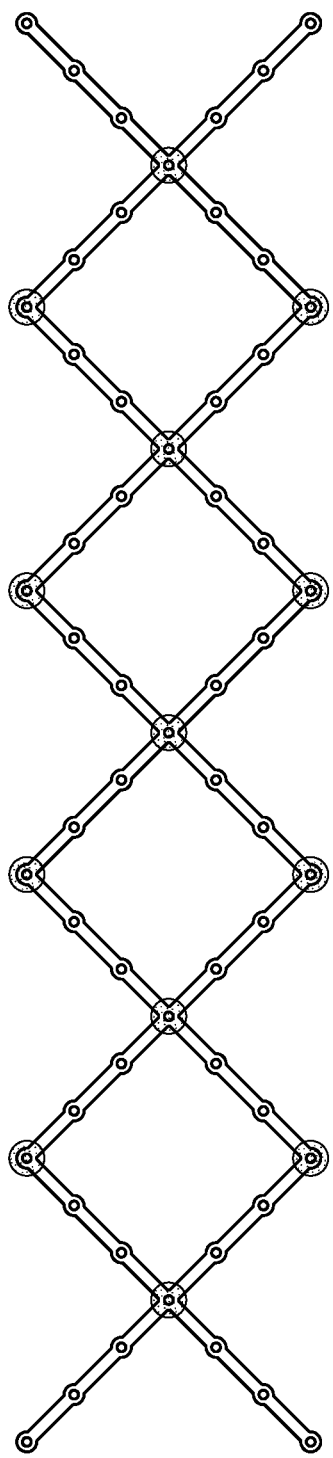
FIGS. 19B-19F illustrate schematic views of steps in a method of fabrication.

Alignment guides (e.g., pins) may be placed through the openings. Not all openings may have pins placed through them. Instead, the pins may be placed through openings through the openings corresponding to the configuration of articulated joints of the support structure. In other variations, pins may be placed into more or all of the openings of the alignment plate. For example, pins may be placed through each opening of the alignment plate. A schematic of the flattened chain and openings is shown in FIG. 19B, with the openings through which pins may be placed shaded. In other variations, pins may be placed into fewer openings of the alignment plate, including no openings. It should also be appreciated that in some variations, the alignment guides may be attached or integral to the alignment plate. For example, the alignment plate may not comprise openings, but may instead comprise alignment guides permanently extending from the same locations at which alignment guides could be placed through openings in the alignment plate described above.

The alignment plate with loaded pins may be placed on top of a base frame and clamped in place as described in more detail above with respect to the valve support structure 4610.

Eyelets or rivets may then be loaded onto the pins. In variations in which the pin locations include ones that do not correspond to articulated joints of the support structure, the eyelets or rivets may be loaded only onto pins corresponding to articulated joints of the support structure. The eyelets may be the same or have similar features as described above with respect to FIGS. 17F-17G. It should be appreciated that in some variations, an eyelet or rivet may not be placed at each location corresponding to an articulating joint of the support structure. For example, no eyelet or rivet may be placed at articulated joints at which the support structure may be intended to be connected to another support structure.

Figure 19C:
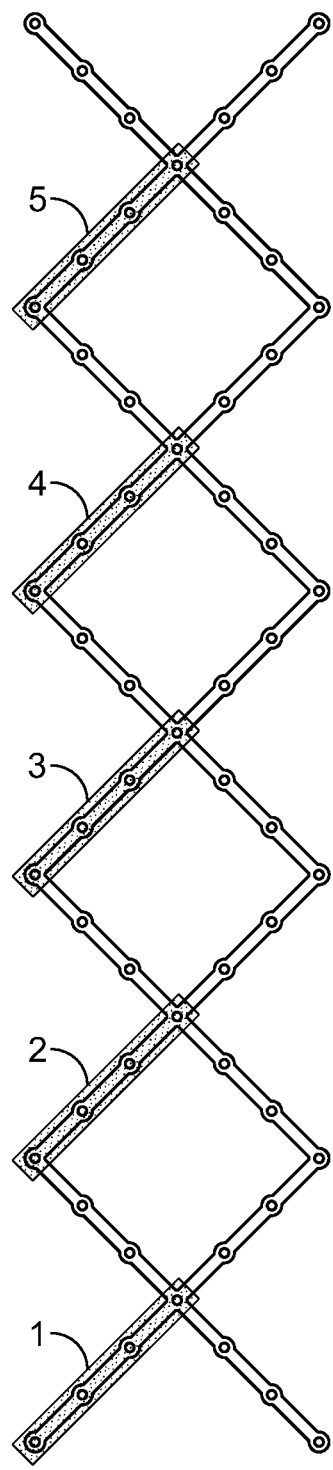

A subset of the strut members may then be placed on the pins. This subset may correspond to the outermost set of strut members of support structure. A schematic of the flattened chain and openings is shown in FIG. 19C, with the strut members placed onto the shaded areas. The numbers 1 through 5 indicate the order in which the strut members may be placed onto the pins. The strut members may be mounted on the pins by placing the pins through orifices of the strut members. The smaller portion of the eyelets may fit through the orifices, while the wider diameter portion of the eyelets may not. The subset of the longitudinal strut members mounted on the pins may comprise the five outermost strut members. The strut members mounted on the pins in this step may all be parallel to each other and may not overlap with each other. While the variation shown in FIG. 19C indicates that the strut members may be placed in order from left to right, in other variations, they may be placed in any other order, such as but not limited to right to left. In so placing the strut members on the pins as described, a pin may be placed through each orifice of the strut members, or a pin may be placed through fewer (e.g., two) orifices of each strut member.

Figure 19D:
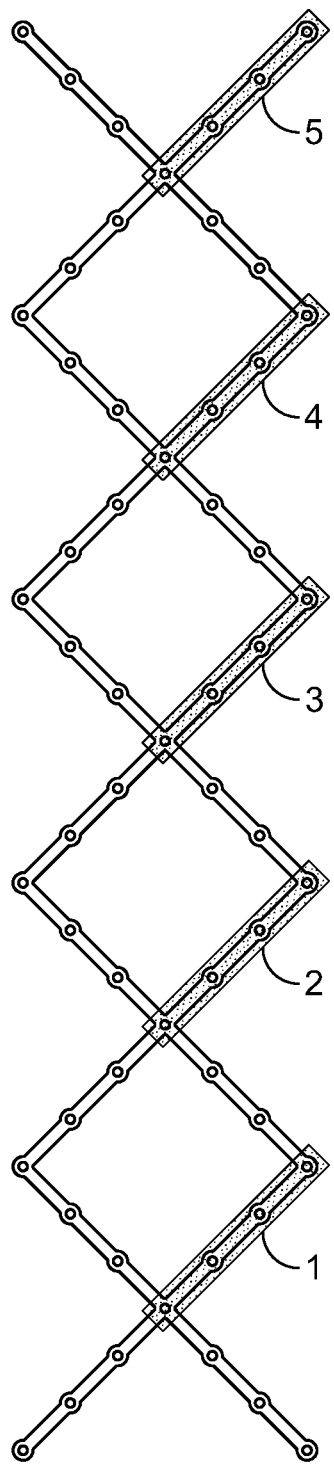

A second subset of the strut members of the support structure may then be placed on the pins. A schematic of the flattened chain and openings is shown in FIG. 19D, with the strut members placed onto the shaded areas. The numbers 1 through 5 indicate the order in which the strut members may be placed onto the pins. These strut members may comprise five parallel strut members. While the variation shown in FIG. 19D indicates that the strut members may be placed in order from left to right, in other variations, they may be placed in any other order, such as but not limited to right to left. In so placing the strut members on the pins as described, a pin may be placed through each orifice of the strut members, or a pin may be placed through fewer (e.g., two) orifices of each strut member.

Figure 19E:
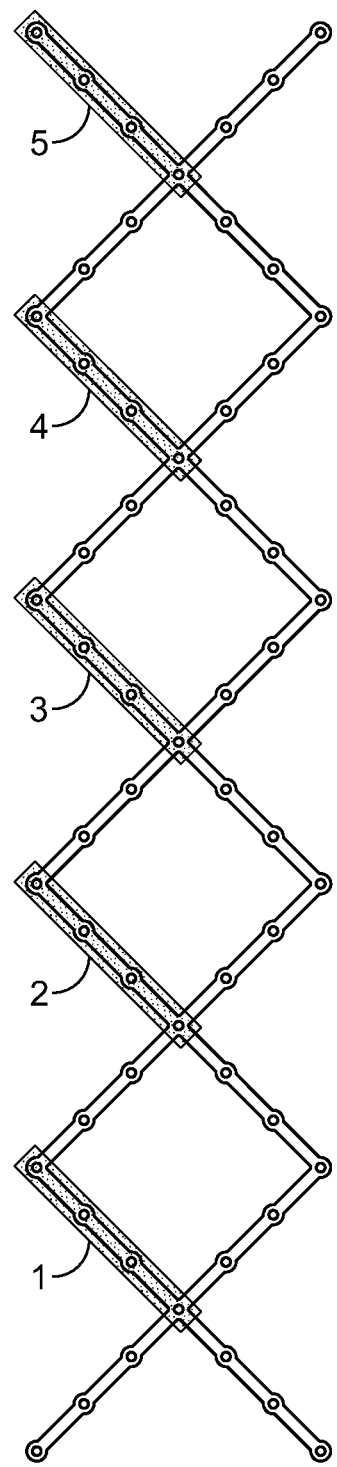

A third subset of the strut members of the support structure may then be placed on the pins. A schematic of the flattened chain and openings is shown in FIG. 19E, with the strut members placed onto the shaded areas. The numbers 1 through 5 indicate the order in which the strut members may be placed onto the pins. These strut members may comprise five parallel strut members. While the variation shown in FIG. 19E indicates that the strut members may be placed in order from left to right, in other variations, they may be placed in any other order, such as but not limited to right to left. In so placing the strut members on the pins as described, a pin may be placed through each orifice of the strut members, or a pin may be placed through fewer (e.g., two) orifices of each strut member.

Figure 19F:
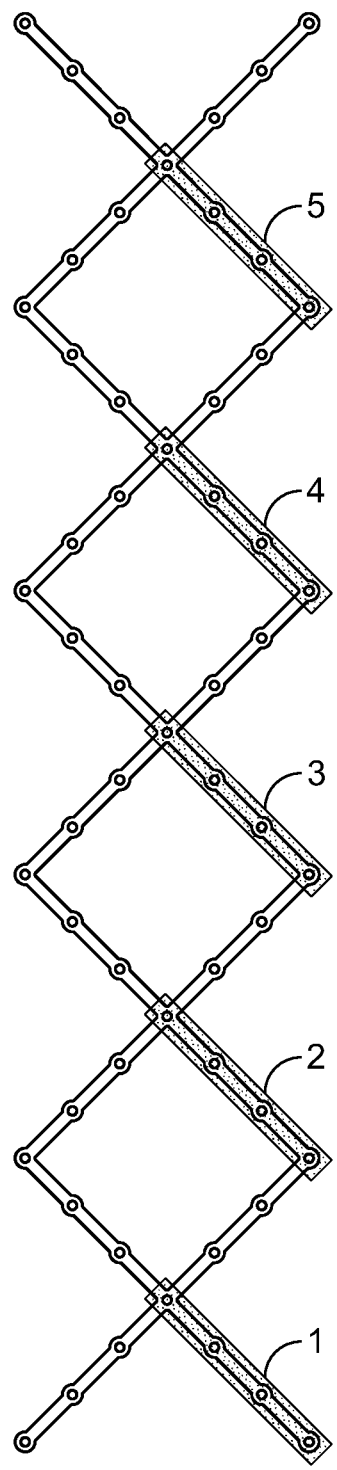

A fourth subset of the strut members of the support structure may then be placed on the pins. A schematic of the flattened chain and openings is shown in FIG. 19F, with the strut members placed onto the shaded areas. The numbers 1 through 5 indicate the order in which the strut members may be placed onto the pins. These strut members may comprise five parallel strut members, and may comprise the innermost strut members. While the variation shown in FIG. 19F indicates that the strut members may be placed in order from left to right, in other variations, they may be placed in any other order, such as but not limited to right to left. In so placing the strut members on the pins as described, a pin may be placed through each orifice of the strut members, or a pin may be placed through fewer (e.g., two) orifices of each strut member.

A cover plate may then be placed over the pins. The cover plate may but need not comprise openings corresponding to the location of each orifice of the strut members of support structure. It should be appreciated that the cover plate may comprise fewer openings; for example, the cover plate may comprise openings only corresponding to the placement of pins, as described above, or openings only corresponding to the placement of eyelets or rivets, as described above. Once placed over the pins, each pin may go through an opening of the cover plate in variations having an opening corresponding to each pin. The openings of the cover plate may be larger than the openings of the alignment plate to allow access for a swaging tool, as described in more detail below.

The alignment plate and the cover plate, and the eyelets and strut members located in between the two plates may then be removed from the base frame by sliding them up and off of the pins. Compressive force may be applied to the alignment plate and the cover plate while removing them from the pins, which may hold the eyelets and strut members. The eyelets may then be swaged, as described in more detail with respect to support structure 3610 above. After the eyelets or rivets are swaged to hold the layered strut members and skirt material together, the alignment plate and cover plate may be removed. The flattened chain may then be shaped into the final shape of the support structure, i.e., into a tubular shape. The ends of the flattened chain may be interlinked to hold the flattened chain into the final shape, e.g., by securing the ends together with eyelets, which may then be swaged. Once rolled into the final shape, an actuator may in some instances be attached to the support structure, in the manner described in more detail above. In other variations, an actuator may be attached to the flattened chain before it is shaped into the final shape.

It should be appreciated that the method of fabrication may be performed in the reverse order. It should also be appreciated that certain steps may be performed in different orders; for example, each group of strut members placed onto the pins may be placed onto the pins from right to left. It should also be appreciated that the method of fabrication may comprise the addition of skirt material and/or valve leaflets, which may be attached by being sandwiched between strut members, in a manner similar to that described above. It should also be appreciated that the support structure described herein may be fabricated in a similar method using three-dimensional printing. In some variations, three-dimensional printing may be used to print the flattened chain of components described herein, either from outermost to innermost, or from innermost to outermost, and then the chain may be shaped into a tubular structure. In other variations, three-dimensional printing may be used to print the strut members of the flattened chain, while the skirt and/or valve leaflets may be added separately during the printing process. In yet other variations, three-dimensional printing may be used to print the device in its final tubular form.

It should be appreciated that the support structures described herein may be fabricated using variations of the methods described above. In another variation, the support structure 4610 may also be fabricated by connecting the strut members into a flattened chain by layering the strut members and then securing them together. This may be facilitated using alignment guides. More specifically, the strut members may be connected by placing the appropriate orifices 4613 of the strut members onto alignment guides in an appropriate order. In one variation, the strut members may be placed onto the alignment guides in an order from outer-most to inner-most: the outer layer of longitudinal strut members (e.g. 4611-1, 4611-3) may first be placed onto the alignment guides through orifices 4613; the inner layer of longitudinal strut members (e.g. 4611-2, 4611-4) may then be placed onto the alignment guides through orifices 4613; then the outer commissure strut members (first the outer second commissure strut members 4619$y$-1, then the outer first commissure strut member 4619$x$-1, in variations in which the commissure strut members comprise inner and outer components) may be placed onto the alignment guides through orifices 4613; and then the inner commissure strut members (first the inner second commissure strut member 4619$y$-2; then the inner first commissure strut member 4619$x$-2) may be placed onto the alignment guides through orifices 4613. It should be appreciated that the strut members may also be placed onto the alignment guides in an order from inner-most to outer-most: the inner commissure strut members (first the inner first commissure strut member 4619$x$-2, then inner second commissure strut members 4619$y$-2) may be placed onto the alignment guides through orifices 4613; then the outer commissure strut members (first the outer first commissure strut member 4619$x$-1, then the outer second commissure strut member 4619$y$-1) may be placed onto the alignment guides through orifices 4613; then the inner layer of longitudinal strut members (e.g. 4611-2, 4611-4) may then be placed onto the alignment guides through orifices 4613; and then the outer layer of longitudinal strut members (e.g. 4611-1, 4611-3) may first be placed onto the alignment guides through orifices 4613. It should be appreciated that these strut members may be placed onto the alignment guides in other orders to the extent that the strut members are not placed onto the same alignment guides.

In some variations, the alignment guides may comprise elongated pins configured to fit through orifices of the strut members. The alignment guides may be arranged in a desired orientation by placement on or through an alignment plate, which may comprise markings or openings to assist in alignment of the alignment guides. The alignment plate may comprise an opening corresponding to the location of each orifice 4613 of the strut members of support structure 4610. To use the alignment plate to fabricate the support structure 4610, the alignment guides may be placed through each opening that corresponds to the location of an articulated joint 4615 of support structure 4610. In other variations, the alignment plate may comprise an opening corresponding to the location of each articulated joint 4615. In such variations, to use the alignment plate to fabricate the support structure 4610, the alignment guides may be placed through each opening of the alignment plate. It should be appreciated that the alignment guides throughout the methods of fabrication described herein may have any suitable design for holding the strut members in place relative to each other. For example, the alignment guides may comprise rails that may fit around one or more edges of the strut members, or the alignment guides may comprise recesses into which the strut members may fit.

The strut members may be held together via rivets. In some variations, the rivets may be placed onto the alignment guides before the strut members are placed onto the alignment guides. The eyelets or rivets may comprise a larger portion and a smaller portion, where the larger portion of the eyelets or rivets (i.e., the flange) is larger in at least one cross-sectional dimension than the smaller portion of the eyelets. The eyelet or rivet may be loaded onto the alignment guides such that the eyelet or rivet flange resides against to the alignment plate. The dimensions of the flange of the eyelets or rivets may be such that it may not pass through the openings of the alignment plate. The dimensions of the flange of the eyelets or rivets may also be such that it may not pass through the orifices 4613 of the strut members of the support structure 4610, while the dimensions of the smaller portion of the eyelets or rivets may be such that it may pass through the orifices 4613 of the strut members of the support structure 4610. Thus, when the strut members are placed on the alignment guides, the narrower portion of the eyelets or rivets may pass through the orifices 4613, sandwiching the flange between the alignment plate and the strut members. The narrower portion of the eyelets or rivets may have a height sufficient to pass fully through all of the elements layered into the alignment guides during the fabrication process when the flange is sandwiched as described, such that the end of the eyelet or rivet may be swaged.

After the strut members are layered on the alignment guides, the rivets may be swaged to secure the strut members together. The rivets and strut members may be removed from the alignment guides in order to swage the rivets. In some variations, a hand tool may be used to swage the rivets. In other variations, the rivets may be swaged in an automated manner using XY frame machines. In some variations, the components may be held in place during swaging by pressing the layered components between the alignment plate and a cover plate. The cover plate may comprise openings that may be configured to correspond to the location of the rivets, to allow access for swaging.

After the strut members are secured together via rivets, the flattened chain may be shaped into the desired continuous support structure 4610, and the two ends of the flattened chain may be secured together via rivets. In some variations, the flattened chain may be shaped into the desired shape by wrapping the flattened chain around a cylindrical mold.

The tissue valve 4621 may be mounted in a secure, sutureless manner using a similar method of fabrication. In one variation, the tissue valve may be suturelessly attached to the support structure 4610 as part of the fabrication process described above using alignment guide by sandwiching the leaflets between the inner and outer longitudinal strut members and commissure strut members. In some variations, the leaflets may comprise pre-cut openings configured to receive the alignment guides (e.g., elongated pins). In other variations, the alignment guides may be configured to pierce or cut the leaflets (e.g., by comprising a sharpened or pointed end) in order to allow the leaflets to be placed over the alignment guides. The leaflets may be placed onto the alignment guides between strut members, such that when the strut members are fixed together with rivets, as described above, the leaflets are as a result fixed between the strut members. Coaptation struts may also be attached using the alignment guides. After the flattened chain is wrapped into the continuous support structure 4610, the coaptation struts 4651 may be rotated proximally from their fabrication position to their biasing position, and the proximal ends may be attached to the commissure struts 4651 to sandwich the leaflets of valve 4621 between the coaptation struts 4651 and commissure strut members 4619.

It should be appreciated that while the fabrication method above is described with respect to support structure 4610, a similar method may be used for any number of support structure, valve, and skirt designs. to fabricate the other structures described here, which may or may not have attached valves and/or skirts). For example, a similar method of fabrication may be used to fabricate any of the support structures described herein (10, 10', 2510, 2710, 3910, 3810, 4610), with or without attached skirts and/or valves.

Figure 20A:
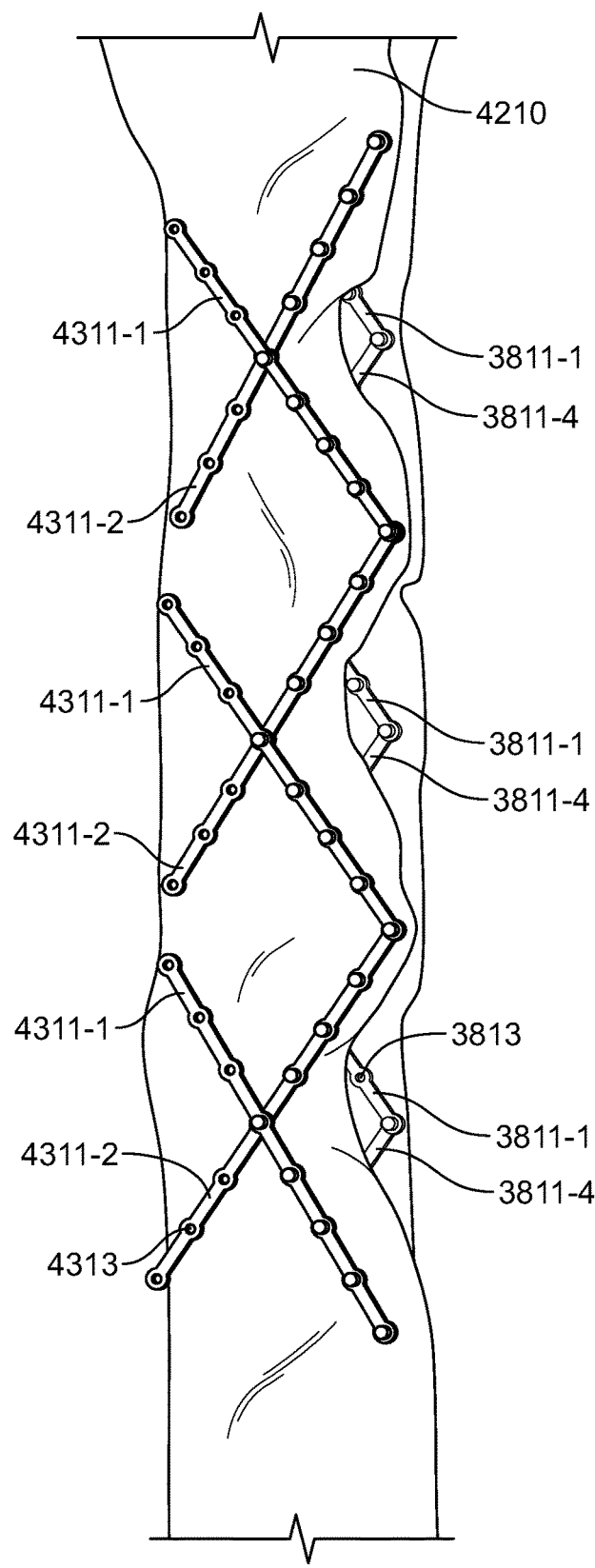
FIGS. 20A-20B are top perspective illustrations of methods of fabricating a support structure with a skirt.

In some variations, a skirt 4210 may be attached to the support structure 3810 using a fabrication method similar to that described above with respect to FIGS. 18A-18R. In one variation, depicted in FIGS. 20A and 20B, the support structure 3810 with an attached skirt 4210 may be fabricated by connecting strut members into a flattened chain by layering the strut members and skirt and then securing them together. As described above with respect to support structure 4610, this may be facilitated using alignment guides. More specifically, to fabricate the structure 3810 with skirt 4210, the strut members may be placed onto the alignment guides in an order from outer-most to inner-most. As shown in FIG. 20A, the strut members 3811 making up support structure 3810 may first be placed onto the alignment guides through orifices 3813. In doing so, the outer strut members 3811 (the set of three outer strut members 3811-2 (not shown) and three outer strut members 3811-4) may first be placed onto the alignment guides through orifices 3813 at the locations of the articulated joints 3815 (3815-1, 3815-5, 3815-11 and 3815-3, 3815-7, 3715-9, respectively). The inner strut members 3811 (the set of three inner strut members 3811-1 and three inner strut members 3811-3 (not shown)) may then be placed onto the alignment guides through orifices 3813 at the locations of the articulated joints 3815 (3815-1, 3815-3, 3815-9 and 3815-5, 3815-7, 3815-11, respectively). The skirt material may then be placed above the strut members 3811. In some variations, the skirt material may comprise openings configured to receive the alignment guides through them. In other variations, the alignments may be configured to pierce or cut the skirt material (e.g., by comprising a sharpened or pointed end) in order to allow the alignment guides to be placed through the skirt material. An outer layer of strut members 4311 may then be layered on top of the skirt material, as shown in FIG. 20A. In the variation shown in FIG. 20A, the strut members 4311 may comprise six struts 4311 having orifices 4313: three inner strut members 4311-1 and three outer strut member 4311-2. The three outer strut members 4311-2 may first be placed onto the alignment guides through orifices 4313; the three inner strut members 4311-1 may then be placed onto the alignment guides through orifices 4313. The placement of the alignment guides through the inner and outer strut members 4311 may be such that each strut is placed over two alignment guides; one at a location corresponding to articulated joint 4315-1 spaced apart from its ends (which may or may not be a midpoint of the strut member 4311), and one at a location corresponding to articulated joint 4315-2 at an end of the strut member (in the view shown in FIG. 20A, the right-most end). Each of these alignment guides may go through the orifices 4313 of one inner strut member 4311-1 and one outer strut member 4311-2.

It should also be appreciated that the strut members may also be placed onto the alignment guides in an order from inner-most to outermost. In this case, the strut members 4311 may first be placed onto the alignment guides as described above, but with the three inner strut members 4311-1 may first be placed onto the alignment guides, and the three outer strut members 4311-2 then be placed onto the alignments guides. The skirt material may then be placed above the strut members 4311 and onto the alignment guides, in a manner similar to that described above. The strut members 3811 of support structure 3810 may then be placed onto the alignment guides, with inner strut members 3811-1, 3811-3 being placed first onto the alignment guides, and then outer strut members 3811-2, 3811-2 being placed onto the alignment guides.

In some variations, the alignment guides may comprise elongated pins configured to fit through the orifices of the strut members. The alignment guides may be arranged in a desired orientation by placement on or through an alignment plate, which may comprise markings or openings to assist in alignment of the alignment guides. The alignment plate may comprise an opening corresponding to the location of each orifice 3813 and 4313 of the strut members 3811 and 4311, and the alignment guides may be placed through each opening corresponding to the location of an articulated joint 3815 or 4315. In other variations, the alignment plate may comprise an opening 3620 corresponding to the location of each desired articulated joint 3815 and 4315. In such variations, to use the alignment plate, the alignment guides may be placed through each opening of the alignment plate. It should be recognized that the alignment guides placed through orifices 4313 of the strut members 4311 need not be the same alignment guides placed through orifices 3813 of strut members 3811 of support structure 3810.

Figure 20B:
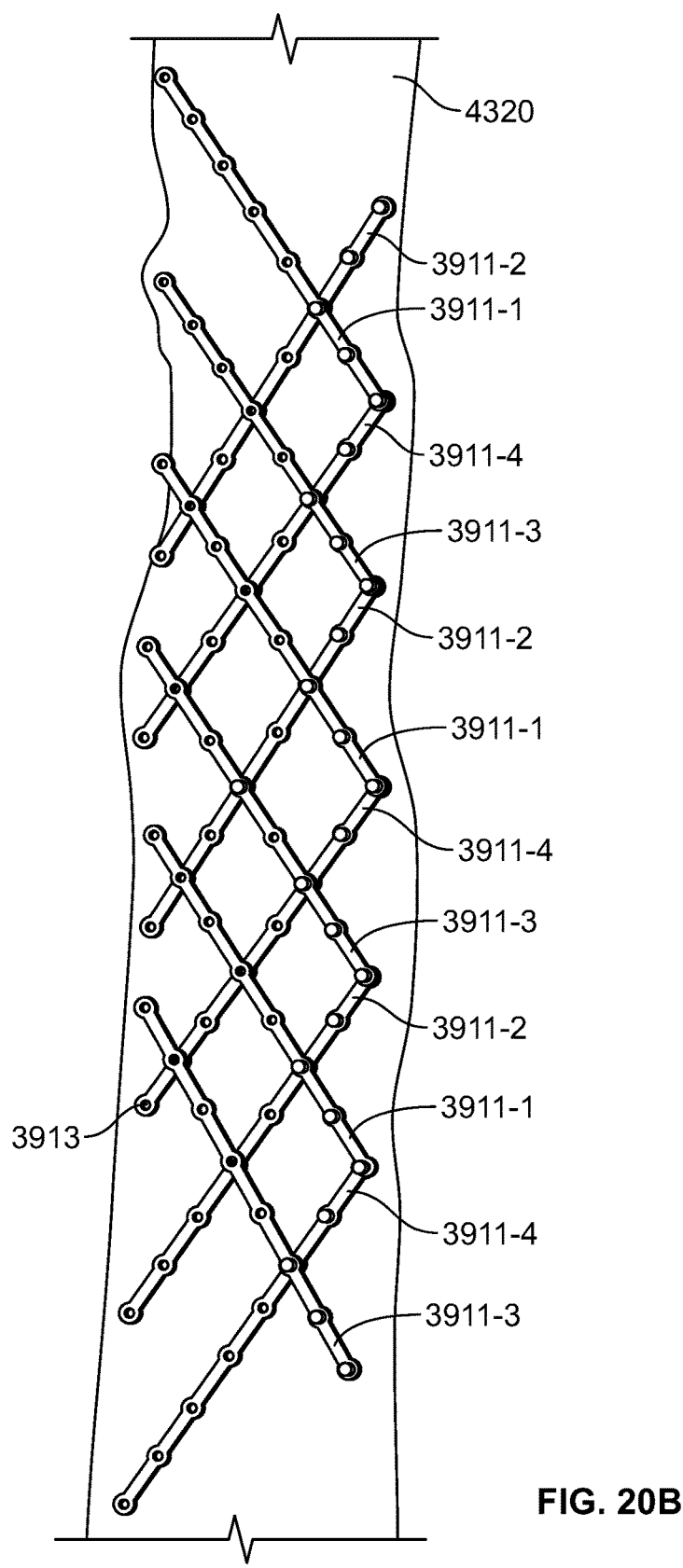

It should also be appreciated that the strut members 4311 may have other numbers and configurations. In some variations, the strut members 4311 may have the same number and configuration as strut members 3811 making up support structure 3810. Furthermore, a similar method of fabrication may be used for attaching a skirt to other support structures of combination structures. In general, the skirt may be attached to a support structure by sandwiching the skirt between the strut members of two support structures. These two support structures may be the same, or the two support structures may be different (as in the example above with strut members 3811 and 4311). FIG. 20B illustrates another example in which the skirt 4320 is sandwiched between two sets of strut members 3911 both configured to make up a support structure 3910 when connected into a continuous support structure. Similarly to described above with respect to FIG. 20A, the strut members may be connected into a flattened chain by layering the strut members and the skirt and then securing them together, which may be facilitated using alignment guides. More specifically, to fabricate the structure 3910 with skirt 4220, the strut members may be placed onto the alignment guides in an order from outer-most to inner-most. The strut members 3911 making up support structure 3910 may first be placed onto the alignment guides through orifices 3913. In doing so, the outer strut members 3911 (the set of three outer strut members 3911-2 and three outer strut members 3911-4) may first be placed onto the alignment guides through orifices 3913 at the locations of the articulated joints 3915 (3915-1, 3915-5, 3915-11, 3915-15 and 3915-3, 3915-7, 3915-9, 3915-13 respectively). The inner strut members 3911 (the set of three inner strut members 3911-1 and three inner strut members 3911-3) may then be placed onto the alignment guides through orifices 3913 at the locations of the articulated joints 3915 (3915-1, 3915-3, 3915-9, 2915-15 and 3915-5, 3915-7, 3915-11, 3915-13 respectively). The skirt material may then be placed above the strut members 3811. In some variations, the skirt material may comprise openings configured to receive the alignment guides through them. In other variations, the alignments may be configured to pierce or cut the skirt material (e.g., by comprising a sharpened or pointed end) in order to allow the alignment guides to be placed through the skirt material. An outer layer of strut members 3911 may then be layered on top of the skirt material, as shown in FIG. 20B. The inner strut members 3911 (the set of three inner strut members 3911-1 and three inner strut members 3911-3) may first be placed onto the alignment guides through orifices 3913 at the locations of the articulated joints 3915 (3915-1, 3915-3, 3915-9, 2915-15 and 3915-5, 3915-7, 3915-11, 3915-13 respectively). The outer strut members 3911 (the set of three outer strut members 3911-2 and three outer strut members 3911-4) may then be placed onto the alignment guides through orifices 3913 at the locations of the articulated joints 3915 (3915-1, 3915-5, 3915-11, 3915-15 and 3915-3, 3915-7, 3915-9, 3915-13 respectively).

In some variations, the alignment guides may comprise elongated pins configured to fit through the orifices of the strut members. The alignment guides may be arranged in a desired orientation by placement on or through an alignment plate. An example of an alignment plate 4410 is shown in FIG. 18A, which may comprise markings 4440 and openings 4420 to assist in alignment of the alignment guides. The alignment plate 4410 may comprise an opening 4420 corresponding to the location of each orifice 3913 of the strut members 3911, and the alignment guides may be placed through each opening corresponding to the location of an articulated joint 3915. In other variations, the alignment plate may comprise an opening corresponding to the location of each desired articulated joint 3815 and 4315. In such variations, to use the alignment plate, the alignment guides may be placed through each opening of the alignment plate. It should be recognized that the alignment guides placed through orifices 4313 of the strut members 4311 need not be the same alignment guides placed through orifices 3813 of strut members 3811 of support structure 3810.

The strut members discussed with respect to FIGS. 20A and 20B may be held together via rivets. In some variations, the rivets may be placed onto the alignment guides before the strut members are placed onto the alignment guides. After the strut members are placed onto the alignment guides, the rivets may be swaged to secure the strut members together. In some variations, a hand tool may be used to swage the rivets. In other variations, the rivets may be swaged in an automated manner using XY frame machines. The alignment guides may then be removed from the orifices. In some variations, the components may be held in place during swaging by pressing the layered components between the alignment plate and a cover plate. The cover plate may comprise openings that may be configured to correspond to the location of the rivets, to allow access for swaging.

After the strut members are secured together via rivets, the flattened chain may be shaped into a continuous support structure, and the two ends of the flattened chain may be secured together via rivets. In some variations, the flattened chain may be shaped into the desired shape by wrapping the flattened chain around a cylindrical mold.

Figure 21A:
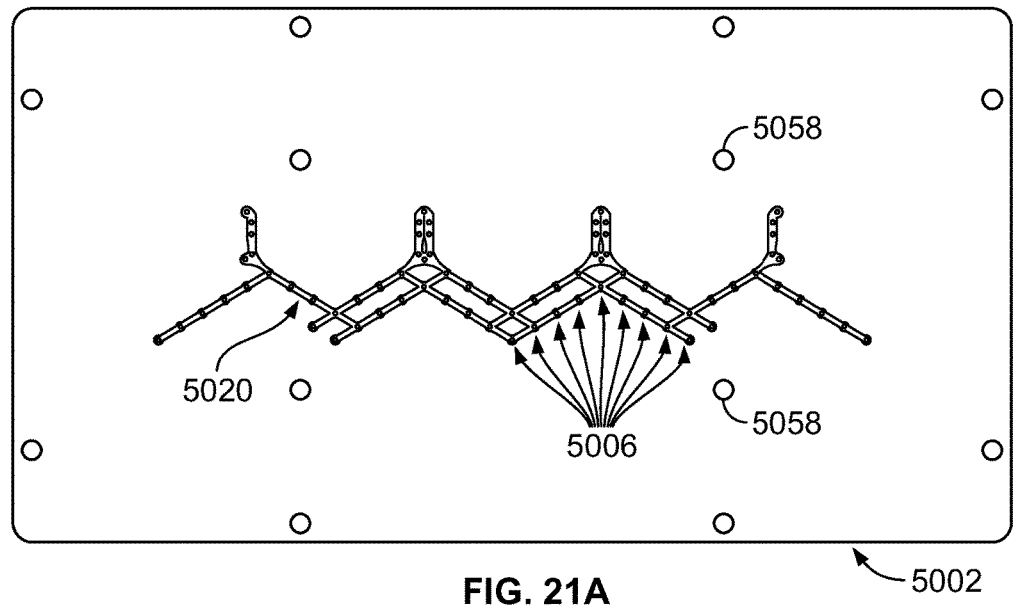
FIGS. 21A and 21B depict an embodiment of backing and cover plates configured for assembling a medical device.
Figure 22A:
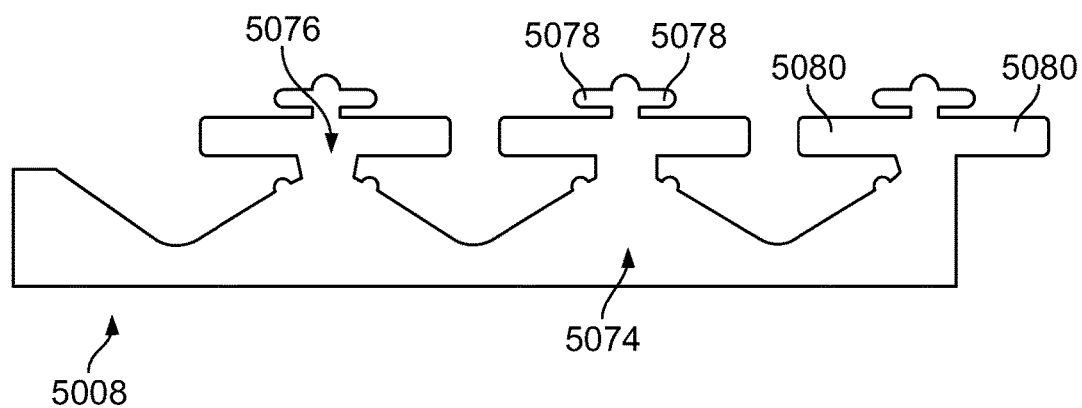
FIGS. 22A and 22B depict an embodiment of a seal material and valve leaflets for a valve of a medical device.
Figure 22B:
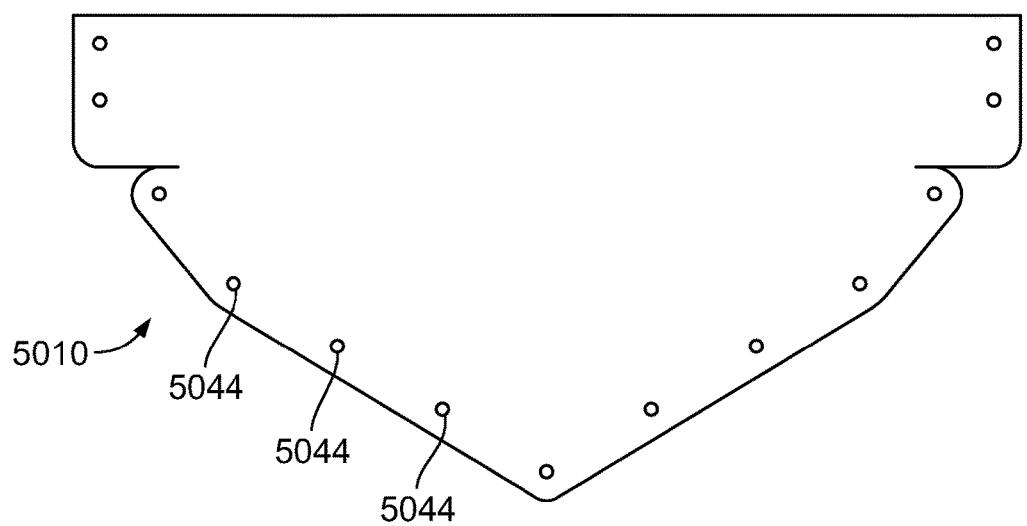
Figure 23A:
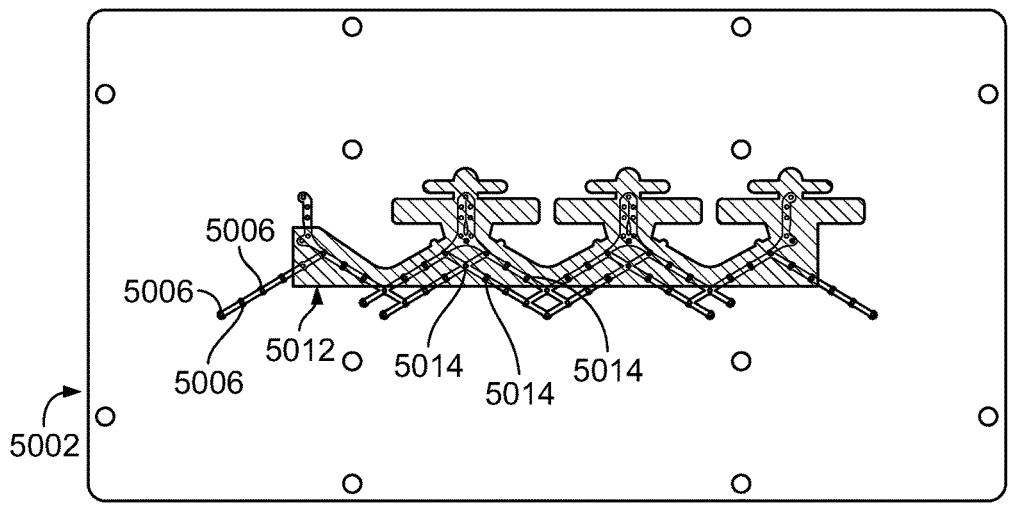
FIGS. 23A to 23Q are schematic illustrations of another embodiment for manufacturing a medical device.
Figure 23B:
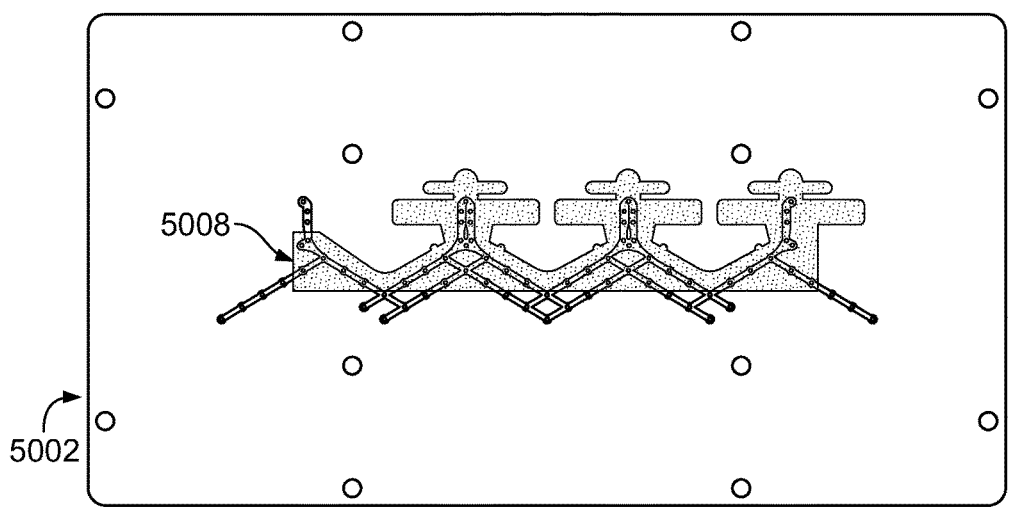
Figure 23C:
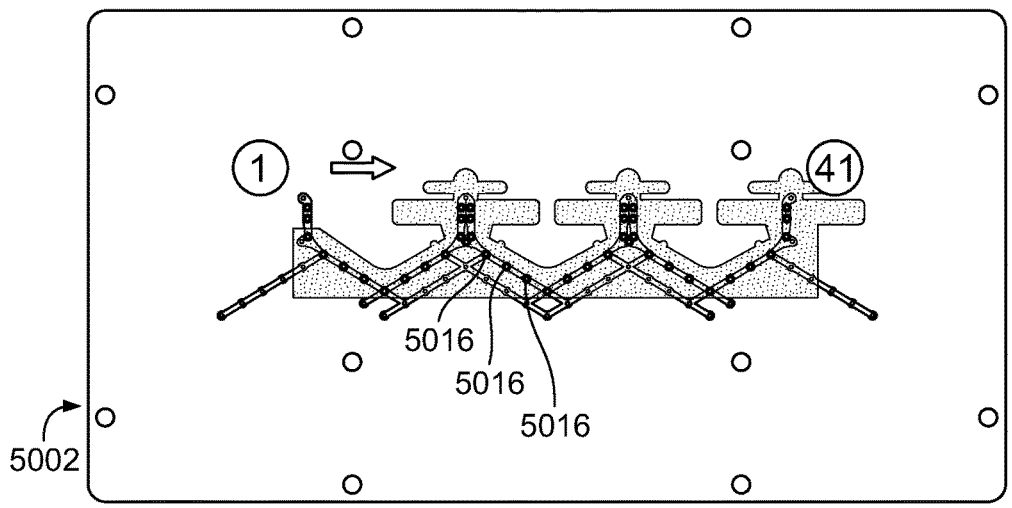
Figure 23D:
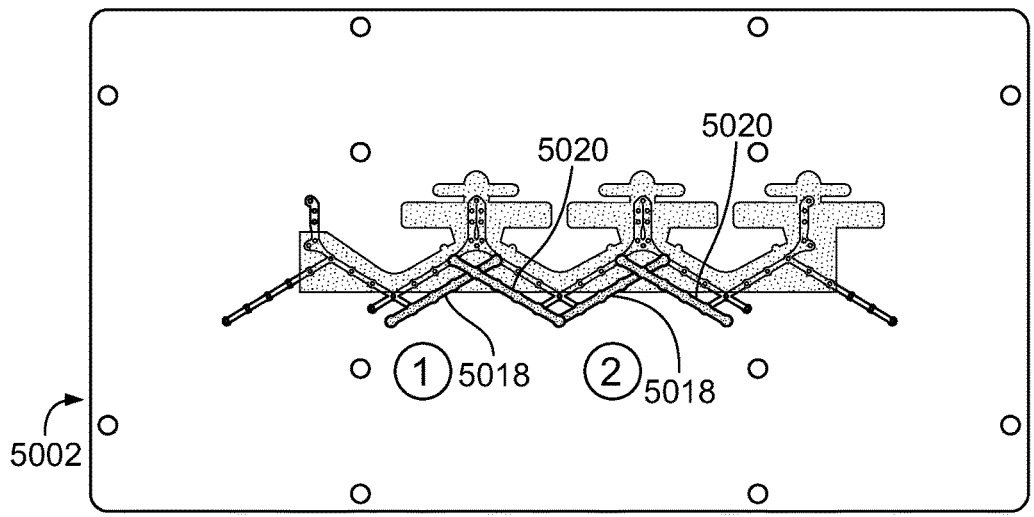
Figure 23E:
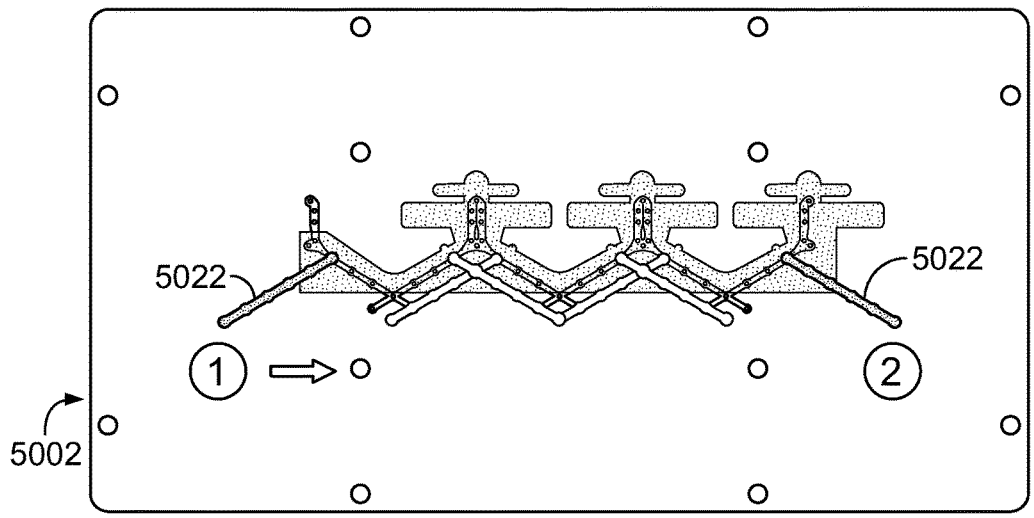
Figure 23F:
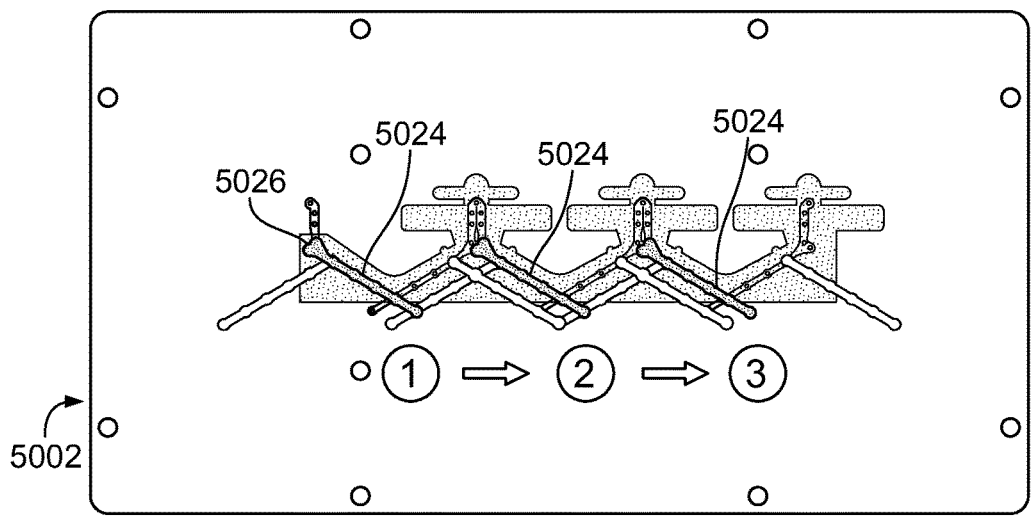
Figure 23G:
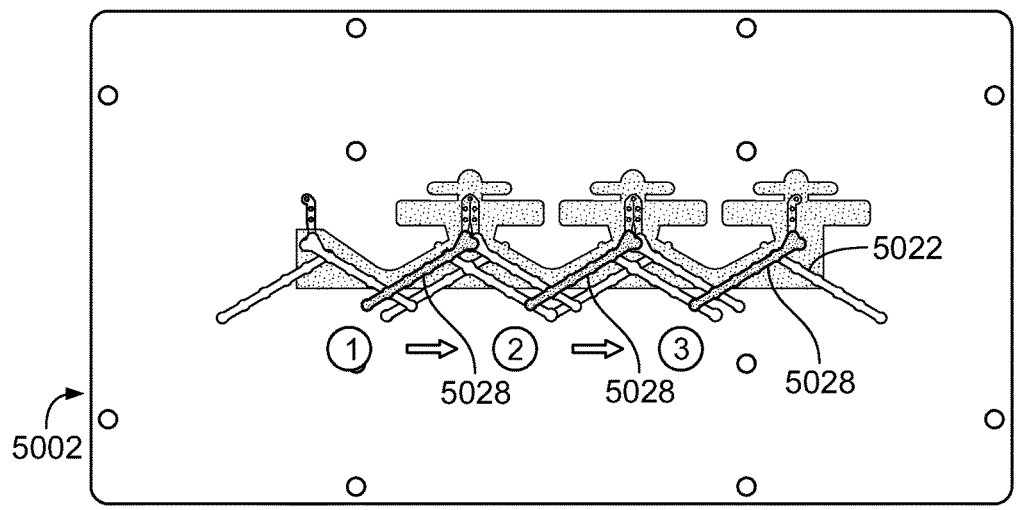
Figure 23H:
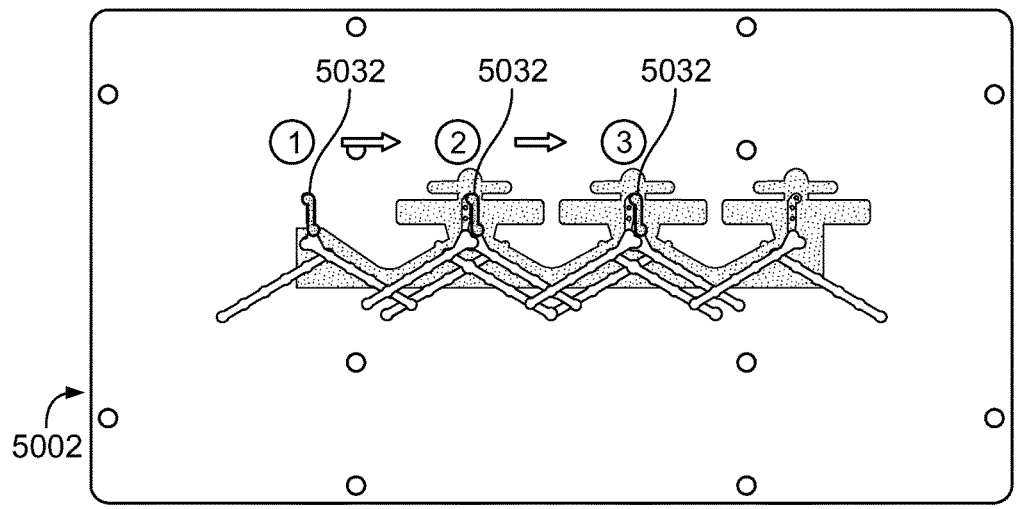
Figure 23I:
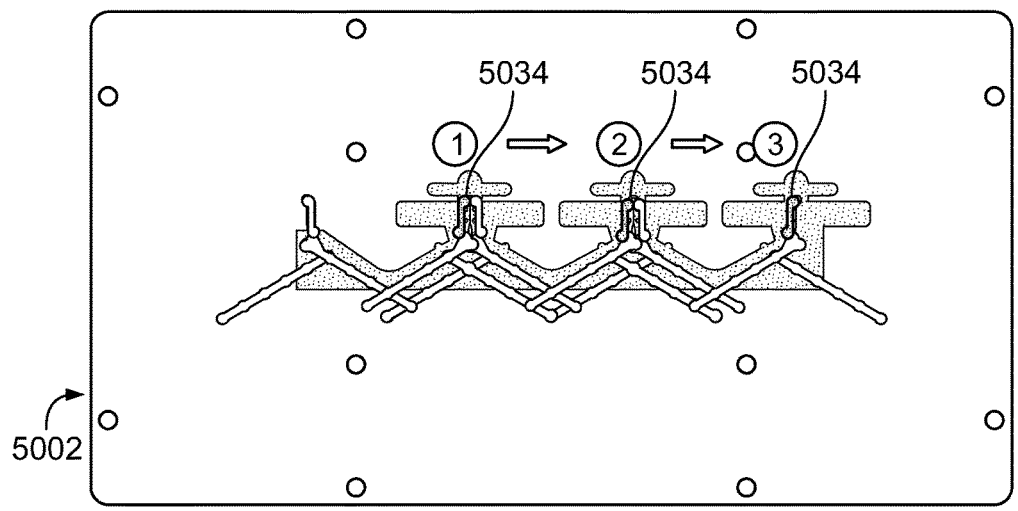
Figure 23J:
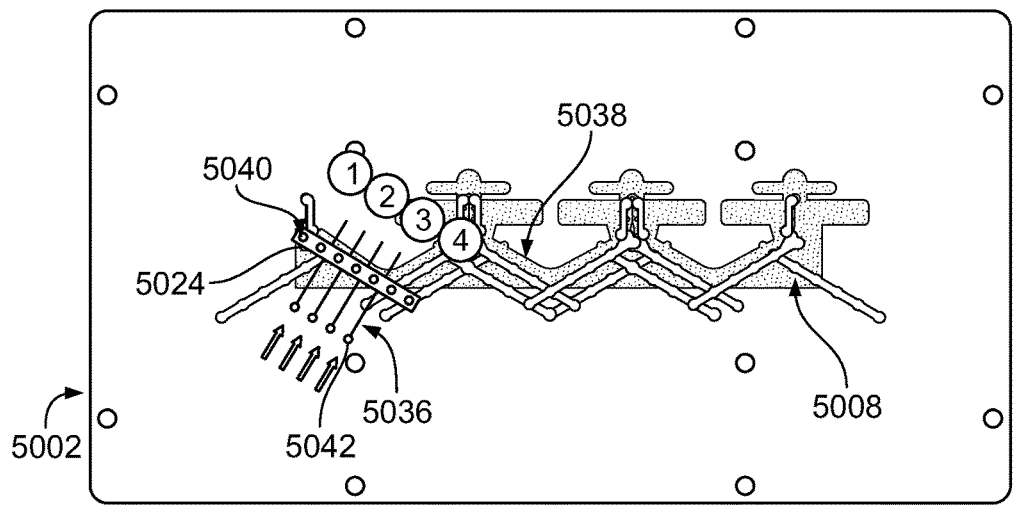
Figure 23K:
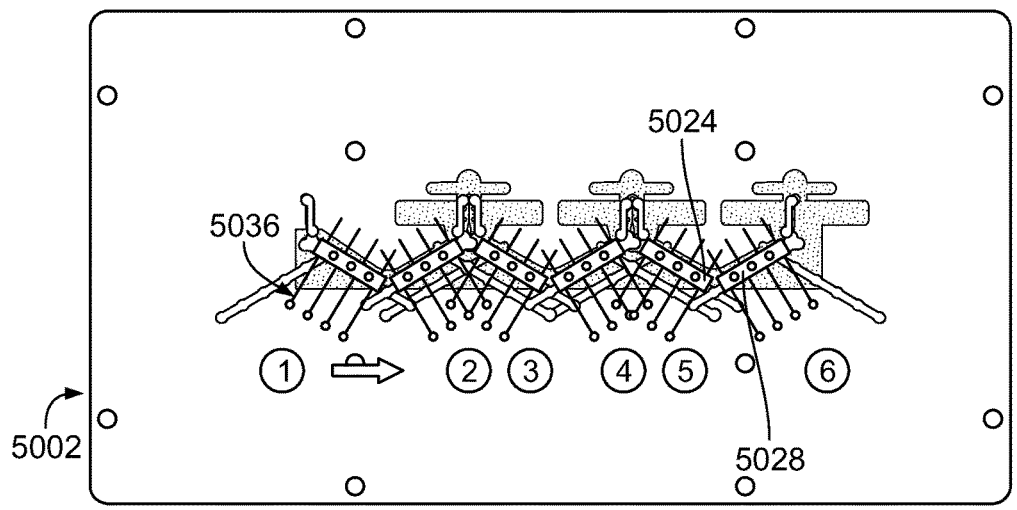
Figure 23L:
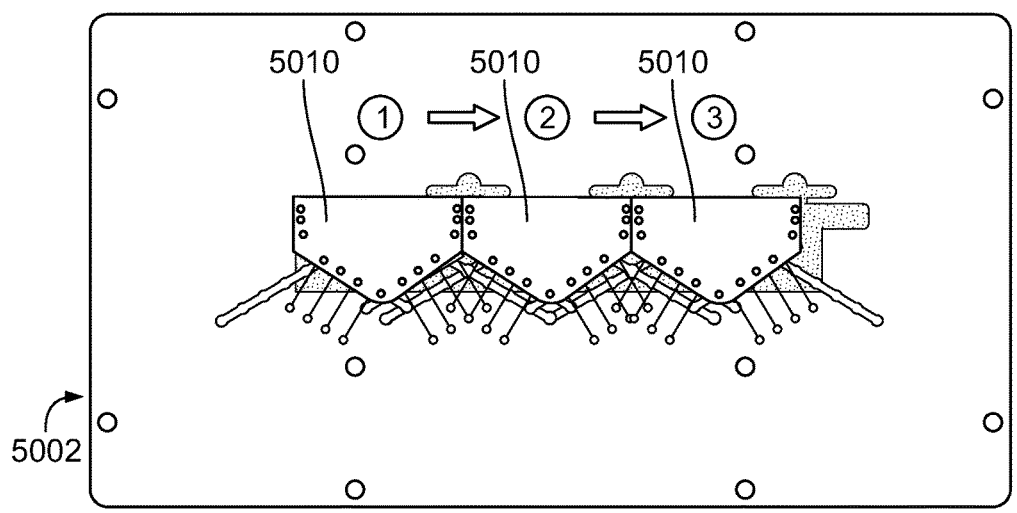
Figure 23M:
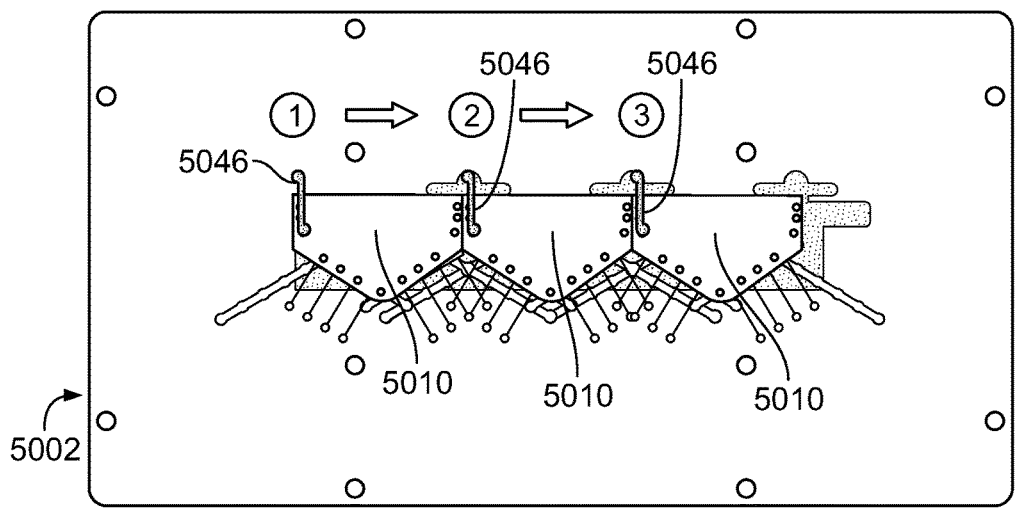
Figure 23N:
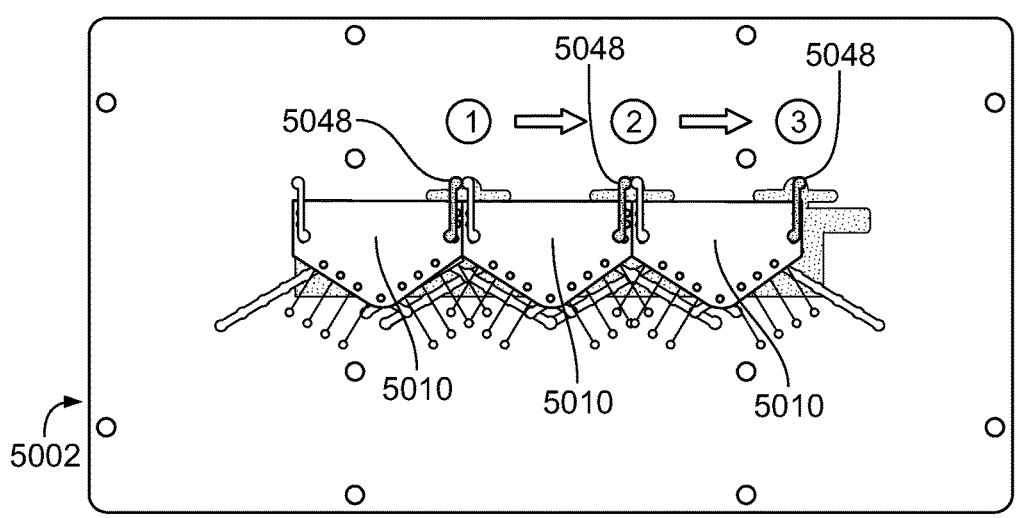
Figure 23O:
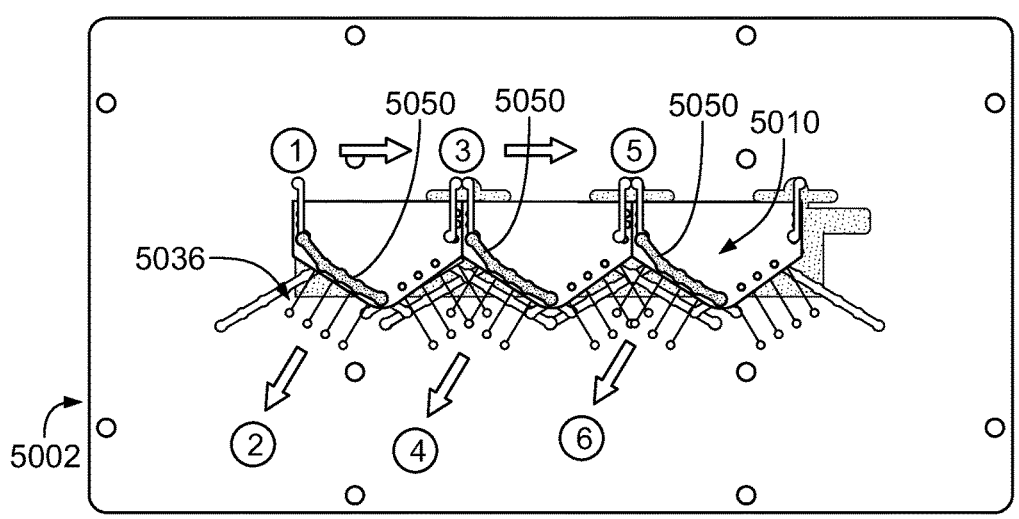
Figure 23P:
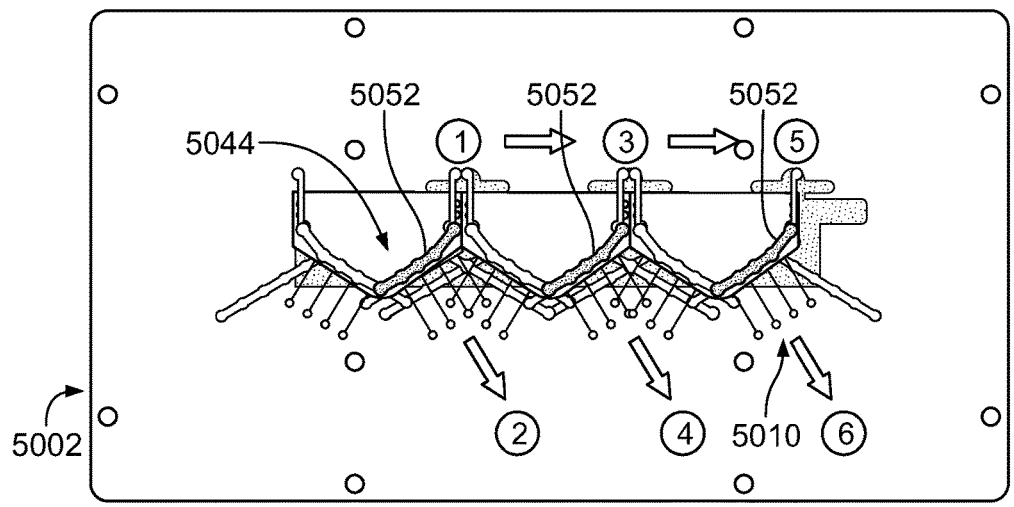
Figure 23Q:
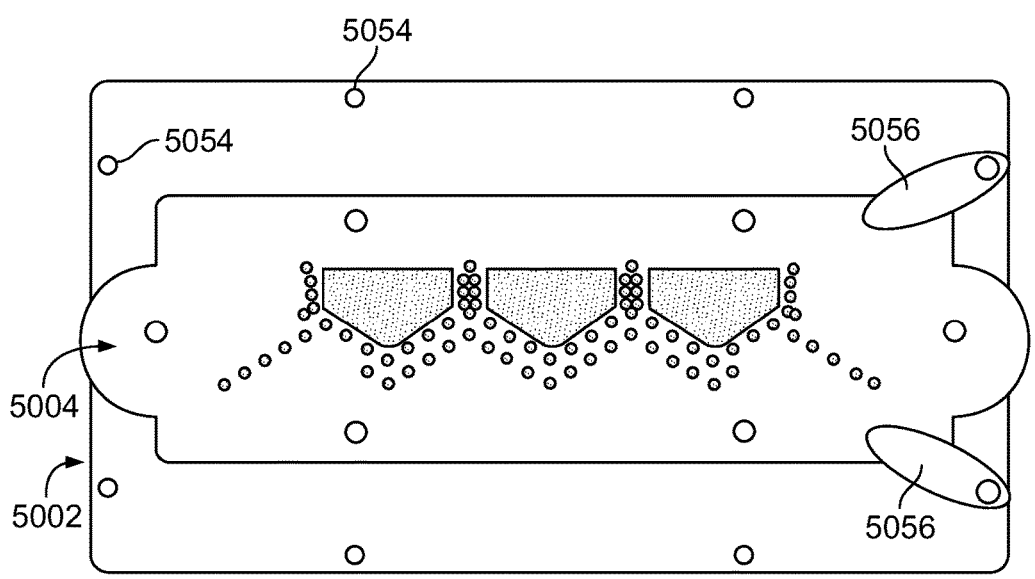

FIGS. 23A to 23Q schematically depicts another assembly process for an articulated stent structure. In this particular assembly, several optional features of the articulated stent structure are also included, but in other variations, one or more, or all of these optional features may be excluded. The assembly process utilizes an assembly system comprising a backing plate or support 5002 and a cover plate or support 5004, depicted in FIGS. 21A and 21B, respectively, along with alignment pins (for clarity, not shown in the pin openings 5006 of the backing plate 5002), which are used to facilitate alignment of the various stent components during the manufacturing process. In this particular embodiment, the stent structure comprises an optional sealing material 5008, shown in FIG. 22A, and optional valve leaflets 5010, shown in FIG. 22B. As shown in FIG. 21A, optional indicia or template markings 5020 may be provided on the backing plate 5002 to facilitate proper placement of the struts, and in some variations the markings may have a shape like the struts to be placed into the backing plate 5002.

In this exemplary embodiment, the backing plate 5002 is placed onto a jig or other structure configured to removably retain the backing plate 5002, but in other embodiments the backing plate may be integrally formed with a jig or other assembly structure. Pins are then placed through the pin openings 5006 of the backing plate 5002.

Referring to FIG. 23B, a seal material 5008 is placed onto the backing plate 5002 through the pins. Optionally, placement of the seal material 5008 may be optionally performed using a support structure 5012 coupled to the top surface of the seal material, as shown in FIG. 23A. The support structure 5010 may comprise preformed openings 5014 for the pins, which may facilitate piercing of the seal material 5008 by the pins, in embodiments where the seal material 5008 does not have preformed pin openings. After placement of the seal material 5008, the support structure 5012 may be removed, leaving behind the seal material 5008, as shown in FIG. 23B.

Referring to FIG. 23C, eyelets 5016 are then place onto each pin, the head or wider portion facing downward, against the seal material 5008. These may be performed by machine, or may be performed by hand. Forceps or other hand tools may be used for eyelet placement. The eyelets 5016 may be placed in any order, but in some variations, may be placed in an ordered fashion from a first side to a second side, such as from position 1 to 41, as shown in FIG. 23C. The number of eyelets in any one embodiment may be different, but in some variations, the number of eyelets may be in the range of 35 to 45, or 30 to 50, or 20 to 40, or 15 to 50, or 20 to 60, for example. The first side to the second side may be from left-to-right, right-to-left, top-to-bottom or bottom-to-top, for example.

FIG. 23D depicts the placement of the lower struts. In this embodiment, the lower struts 5018 at positions 1 and 2 are placed first, followed by the lower struts 5020. This arrangement achieves an overlap of the outer lower struts 5018 with inner lower struts 5020, as well as an inner and outer strut configuration, which may achieve a smaller collapsed profile and ease of expansion and reduction of the stent structure. In the exemplary process depicted in FIGS. 23A to 23Q, strut positioning onto the backing plate is performed in a left to right manner, but in other examples may be performed in a right to left manner, or some other manner. A consistent assembly direction may or may not reduce assembly errors during the manufacturing process.

In FIG. 23E, the end struts 5022 are placed onto backing plate 5002. In some variations, one or more of the strut positions may comprise two bars at the same location, whether for reinforcement or other purpose. For example, in one further embodiment, the strut location at position 1 may comprise two struts 5018 at the same location, while the strut location at position 2 may comprise a single strut 5018.

In FIG. 23F, the first set of upper struts 5024 are then placed onto the backing plate 5002, starting from position 1 to 2 to 3. In this particular example, optional commissure struts are also provided, such that the upper struts 5022 comprise an enlarged end 5026 which should be oriented superiorly during placement. In other embodiments, however, each of the struts may or may not involve a particular orientation. After placement of upper struts 5024, one of the upper struts 5024 overlaps with one of the end struts, and each of the upper struts 5024 overlaps with one or two lower struts, but not with each other.

In FIG. 23G, the second set of upper struts 5028 are then placed, starting from position 1 to 2 to 3, from left to right, with the enlarged end 5030 oriented superiorly during placement. Each of the second set of upper struts 5030 overlap one or more lower struts, but not with each other.

In FIG. 23H, the first side or set of commissure struts 5032 are placed onto the backing plate 5002. In this particular embodiment, the first set of commissure struts 5032 are the right side struts at the commissures, as viewed during assembly, and may be assembled in order from positions 1 to 2 to 3, from left to right. Each of the first set of commissure struts overlaps with an upper strut at this juncture in the assembly process.

In FIG. 23I, the second side or set of commissure struts 5034 are placed onto the backing plate 5002. In this particular embodiment, the second set of commissure struts 5034 are the left side struts at the commissures, as viewed during assembly, and may be assembled in order from positions 1 to 2 to 3, from left to right. Each of the second set of commissure struts 5034 overlaps with a corresponding commissure strut from the first set, and also an upper strut.

In an variation of the assembly process, instead of each commissure comprising a two part stent, a single piece wishbone or inverted U-shape commissure strut may be used instead, as in some designs, no movement between the two attached commissure struts occurs, or is otherwise required.

With the struts in place on the backing plate, in embodiments optionally including the seal material, the seal material 5008 may be optionally manipulated so that the seal material 5008 may be folded back or tucked in between struts, without using sutures. Referring to FIG. 23J, folding pins 5036 are initially positioned with their heads 5042 in the superior position pushed against the seal material 5008 close to the upper edge 5038 of the seal material 5008, between the eyelets 5040 the upper struts 5022. The pins 5036 are pushed just enough to contact the struts 5024. The pins 5036 are then pivoted or levered in an inferior direction until the heads 5042 of the pins 5036 are almost contacting the backing plate 5002. Then pins 5036 are then pushed under struts 5024 and through the seal material 5008 so that the strut 5024 is generally located about the middle of the pin 5036, as shown in FIG. 23J. In this particular example, four pins 5036 are used along on of the struts 5024, but in other embodiments one, two, three, five, six, seven, eight, nine, or ten or more pins may be used long a strut. FIG. 23K depicts all the pins 5036 after pivoting or levering along all of the upper struts 5024 and 5028.

In FIG. 23L, three optional valve leaflets 5010 are then placed on the backing plate 5002, from positions 1 to 2 to 3, left to right, aligned with the pins corresponding to the commissure struts 5032, 5034 and upper struts 5024 and 5028, shown in earlier figures but covered up by the leaflets in FIG. 23L. Typically, the leaflet material is maintained in a wet state, and may be wetted during assembly to resist or avoid desiccation.

In FIG. 23M, a third set of commissure struts or posts 5046 are then positioned onto the backing plate 5002 using pins, onto the valve leaflets 5010, from positions 1 to 2 to 3, left to right. In FIG. 23N, this is followed by a fourth set of commissure struts or posts 5048 that are placed onto the backing plate 5002 using pins onto the valve leaflets 5010, from positions 1 to 2 to 3, left to right. In conjunction with the first and second sets of commissure struts 5032, 5034, a portion of each valve leaflet 5042 is sandwiched between, or otherwise secured tot eh commissure struts 5032, 5034, 5046 and 5048.

In FIG. 23O, a first set of curved struts 5050 are then positioned onto the backing plate 5002 against the leaflets 5010, from positions 1 to 3 to 4, left to right. After each strut placement, the folding pins 5036 are removed, prior to the placement of the next curved strut 5050, as indicated by removal steps 2 to 4 to 6. This is followed by the placement of another set of curved struts 5052 onto the leaflets 5010 and the backing plate 5002, from positions 1 to 3 to 4, left to right, as shown in FIG. 23P, which also involve the removal of folding pins 5036 after each strut placement. These curved struts 5050, 5052 are pushed sufficiently such that the struts 5050, 5052 may contact the eyelets (not shown in FIG. 23O or 23P).

After the eyelets, struts, sealing material and valve leaflets have been loaded onto the backing plate 5002, the cover plate 5004 or clamping plate is then placed on top of all the components, sandwiching the components between the backing plate 5002 and the cover plate 5004, as shown in FIG. 23Q. Retaining clips 5056 or clamps, may be attached to attachment sites 5054 on the backing plate, to keep the components and the cover plate 5004 together, so that the backing plate 5002, components and cover plate 5004 may be optionally removed as a single composite structure to a swaging machine. The clips 5056 may be rotatable to facilitate clamping or removal of the cover plate 5004 from the backing plate 5002. The backing plate 5002 and the cover plate 5004 may also optionally comprise alignment openings or structures which may form a complementary interfit between the two plates 5002, 5004 or permit a post or pin to be used to maintain or facilitate plate alignment. In the example depicted in FIGS. 21A and 21B, the backing plate comprises cover plate opening 5058 which are configured to align with backing plate openings 5060 on the cover plate 5004 via post or pins inserted therethrough.

Figure 21B:
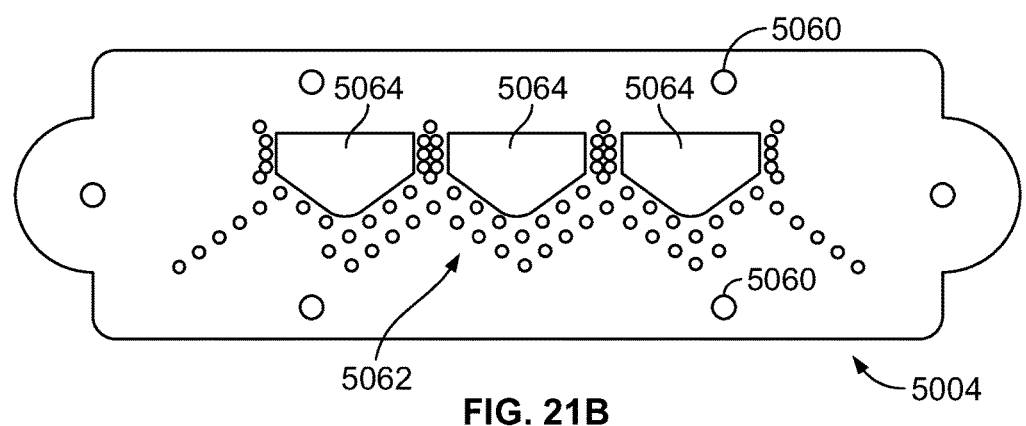

As shown in FIG. 21B, in addition to the plurality of alignment pin openings 5062 configured to receive pins projecting through the backing plate and through the cover plate 5004, the cover plate may optionally comprise leaflet openings 5064. In some variations, the leaflet openings 5064 permit viewing of the leaflet to confirm the positioning of the leaflets during clamping, or to confirm that damage to the leaflets has not occurring during clamping or swaging.

In other examples, however, the swaging tool may be integrated into a jig, such that a cover plate is not needed and swaging may be directly performed on the components, without a cover plate. Each of the eyelets are then swaged, either with the pins in place or with the pins removed before swaging. The eyelet swaging may be performed in a single step for each eyelet, or may comprise two or more steps for each eyelet, where the swaging tool acts only on one side of the eyelet at a time. The eyelets may be swaged serially or simultaneously in parallel.

In some variations, additional sutures or eyelets may be placed at the commissure struts, upper struts or lower struts, to further attach either the valve leaflets or the sealing material to the assembly. For example, an additional eyelet may be swaged at each commissure edge of each valve leaflet to further attach the leaflets to the commissure struts.

After swaging, the assembled layered valve assembly is removed from the backing plate, and the side ends of the layered valve assembly are attached to circularize the layered valve assembly into a tubular or ring-like structure. If a shim was used, the shim may be removed from the assembly before circularization is performed. Because the shim was located between the seal material and the eyelets, the shim may be removed once the pins are removed.

In some further variations, the sealing material may be pre-attached to the support structure, by a mechanical or an adhesive mechanism. The support layer may comprise a metal or hard plastic. As noted above, in use, the sealing material may be pierced by the alignment pins during assembly, but in other variations, the sealing material may comprise pre-formed openings configured to receive the alignment pins. Likewise, the valve leaflets 5010 depicted in FIG. 22B may optionally comprise pre-formed pin openings 5044.

Figure 21C:
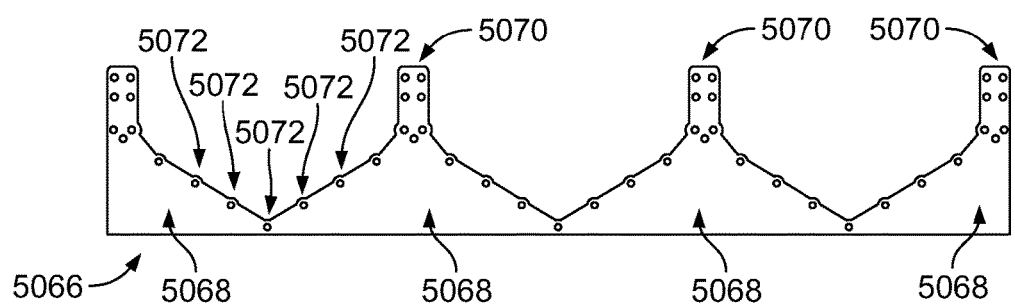
FIG. 21C depicts an embodiment of an optional shim or protective insert usable with the backing and cover plates in FIGS. 21A and 21B.

In some further embodiments, a protective insert or shim 5066, depicted in FIG. 21C, may be optionally placed on top of the lower portion of the sealing material 5008, after the sealing material 5008 is placed onto the backing plate 5002 and before any struts are placed. In some variations, the shim 5066 may aid in protecting the sealing material 5008 during the assembly and or swaging procedure, and may be removed prior to tubularization of the device. The shim 5066 may comprise triangular base regions 5068 and elongate commissure regions 5070. The shim 5066 may comprise pin apertures 5072 to facilitate or maintain desired positioning of the shim 5066 on the backing plate 5002 via the alignment pins. In this particular embodiment, the apertures 5072 of the shim 5088 correspond to the openings 5006 on the backing plate 5002 for the upper struts of the device, but in other embodiments, the shim apertures may correspond to other openings 5006 on the backing plate, or other alignment openings independent of the strut alignment openings. The shim may comprise a metal or plastic material, or other material.

Either prior, during or after tubularization, the seal material 5008 is further attached to stent assembly by wrapping its upper tabs 5078 and its lower tabs 5080 around the commissure struts. The wrapping may go from the outer surface of the commissure struts, to the inner surface, and then back to the outer surface, depending upon the length of the tabs. In some embodiments, the sealing material provides sufficient coverage such that there is no exposed stent on the outer perimeter of the stent assembly. The seal material 5008 may then be secured to the commissure struts using sutures and the eyelets of the commissure struts, or by adhesive or tissue welding, or other known attachment modalities. In other variations, a single tab may be provided to each side of the commissure extension 5076 of the sealing material, or the single tab may be provided to just one side of the commissure extension, like a flag and pole configuration. In some variations, the tabs may comprise a trapezoidal or half-trapezoidal shape, with a wider base and a narrower distal end.

In some variations, the base 5074 of the sealing material 5008 is attached to the lower struts of the valve or stent assembly, but in other variations, the base 5074 remains unattached, even where the commissure extensions are attached to the commissure struts. In some variations, the base 5074 are left unattached to permit expansion of the stent assembly, without the base 5074 constraining expansion due to attachment to the stent assembly. In some further variations, the valve assembly is then placed and secured to a second stent assembly, e.g. one configured for aortic or mitral valve placement, and then the base 5074 of the sealing material 5008 is then attached to the second stent assembly. Examples of combination or composite valve structures are described in U.S. Pub. 2014/0277563, which is hereby incorporated by reference in its entirety.

Particular embodiments of the invention offer distinct advantages over the prior art, including in their structure and applications. While certain advantages are summarized below, the summary is not necessarily a complete list as there may be additional advantages.

The device may allow the user to advert the serious complications that can occur during percutaneous heart valve implantation. Because the device may be configured to be retrievable and re-positionable during implantation into the body, the surgeon may be able to avoid serious complications due to valve mal-positioning or migration during implantation. Examples of these complications include occlusion of the coronary arteries, massive paravalvular leakage, or arrhythmias.

The device may also decrease vascular access complications because of the device's narrow insertion profile. The device's profile may be low, in part, due to its unique geometry, which may allow neighboring struts in the stent to overlap during stent compression. The device's low profile may be further augmented by eliminating the necessity for a balloon or a sheath. In some embodiments, however, the device may be placed within a sheath during insertion. The device's narrow profile offers the advantage of widening the vascular access route options in patients. For instance, the device may enable the delivery of the prosthetic valve through an artery in the leg in a patient whom would have previously been committed to a more invasive approach through the chest wall. The device may therefore decrease complications associated with the use of large profile devices in patients with poor vascular access.

The tissue valve embodiments can offer improved durability by allowing for attachment of the leaflets to flexible commissural posts. The flexible posts may allow dissipation of the stress and strain imposed on the leaflet by the cardiac cycle. The use of multi-ply struts may enable the leaflets to be sandwiched in between the struts, which may re-enforce the leaflet attachments and prevents tearing of sutures and provide a significantly simplified approach for leaflet attachment. The valve may further assume a desirable leaflet morphology, which may further reduce the stress and strain on leaflets. Namely, the angled leaflet attachment to the stent may be similar to the native human aortic valve's inter-leaflet trigone pattern. These properties may significantly improve the longevity of percutaneous heart valve replacement therapies. In addition, in comparison to Nitinol frames, the support structure may have more forceful expansion and higher hoop strength, and may be more fatigue resistant while collapsing more easily. Moreover, it may not require cooling or warning to cause shape changes.

The device could reduce or eliminate arrhythmia complications due to the incremental expansion or compression of the stent. The stent can employ a screw mechanism for deployment, which enables the stent to self-lock or un-lock at all radii. This may enable more controlled deployment and the potential for individualizing the expansion or compression of the device in each patient. Because the expansion or compression of the device may be configured to be reversible at any stage during the procedure, the surgeon may be able to easily reverse the expansion of the device to relieve an arrhythmia. In addition, if an arrhythmia is detected during implantation, the device may be able to be repositioned to further eliminate the problem.

The device may reduce or eliminate paravalvular leak due to the device's ability to be accurately positioned, and re-positioned, if necessary. That may considerably decrease the occurrence and severity of paravalvular leaks. The device may also reduce or eliminate paravalvular leak due to the ability to retain a dynamic seal.

The device may eliminate balloon-related complications. The screw mechanism of deployment exploits the mechanical advantage of a screw. This may provide for forceful dilation of the stent. The lever arms created by the pivoting of the struts in the scissor linkage of the stent may transmit a further expansion force to the stent. The stent may be expanded without the need for a balloon. In addition, the device may have the ability to be forcefully dilated, which may reduce or eliminate the need for pre- or post-ballooning during the implantation procedure in patients.

The device may have more predictable and precise positioning in the body because the difference between the height of the stent in the compressed and expanded position may be small. This "reduced foreshortening" may help the surgeon to position the device in the desirable location in the body. The ability to re-position the device in the body may further confer the ability to precisely position the device in each individual.

In addition to the mechanical advantages, the device may enable a wider population of patients to be treated by a less invasive means for valve replacement. For example, the device may enable patients with co-morbidities, who are not candidates for open chest surgical valve replacement, to be offered a treatment option. The device's ability to assume a narrow profile may also enable patients who were previously denied treatment due to poor vascular access (e.g. tortuous, calcified, or small arteries), to be offered a treatment option. The durability of the valve may expand the use of less-invasive procedures to the population of otherwise healthy patients, who would otherwise be candidates for open chest surgical valve replacement. The device's ability to be forcefully expanded, or assume hourglass, or conical shapes, potentially expands the device application to the treatment of patients diagnosed with aortic insufficiency, as well as aortic stenosis.

The device can also provide a less invasive treatment to patients with degenerative prosthesis from a prior implant, by providing for a "valve-in-valve" procedure. The device could be accurately positioned inside the failing valve, without removing the patient's degenerative prosthesis. It could help the patient by providing a functional valve replacement, without a "re-do" operation and its associated risks.

While this invention has been particularly shown and described with references to particular embodiments, it will be understood by those skilled in the art that various changes in form and details may be made to the embodiments without departing from the scope of the invention encompassed by the appended claims. For the methods disclosed herein, the steps need not be performed sequentially. Each of the features depicted in each embodiment herein in may be adapted for use in other embodiments herein.

I claim:

1. A method of fabricating an articulated support structure, comprising:
   placing a plurality of pins through openings in an alignment plate;
   placing a plurality of eyelets onto the plurality of pins;
   layering a plurality of strut members each having a plurality of orifices onto the plurality of pins by placing the pins through the orifices;
   connecting the plurality of strut members into a chain having a first end and a second end by swaging the eyelets; and
   wrapping the chain into a tubular structure by connecting the first and second ends of the chain.

2. The method of claim 1, further comprising placing a plurality of valve leaflets onto the plurality of pins; wherein at least one of the plurality of strut members is layered below each valve leaflet, and at least one of the plurality of strut members is layered above each valve leaflet.

3. The method of claim 2, further comprising biasing the valve leaflets into a closed configuration after wrapping the chain into a tubular structure, by rotating at least one of the plurality of strut members from a first position to a second position.

4. The method of claim 2, further comprising placing a skirt material onto the plurality of pins, wherein at least one of the plurality of strut members is layered below the skirt material, and at least one of the plurality of strut members is layered above the skirt material.

5. The method of claim 4, further comprising attaching an actuator to the articulated support structure, wherein the actuator is configured to reversibly and incrementally adjust the articulated support structure between an expanded configuration and a compressed configuration.

6. The method of claim 2, further comprising attaching the articulated support structure to a second articulated support structure.

7. The method of claim 6, further comprising attaching an actuator to the second articulated support structure, wherein the actuator is configured to reversibly and incrementally adjust the articulated support structure and the second articulated support structure between an expanded configuration and a compressed configuration.

8. The method of claim 1, further comprising placing a skirt material onto the plurality of pins, wherein at least one of the plurality of strut members is layered below the skirt material, and at least one of the plurality of strut members is layered above the skirt material.

9. The method of claim 8, further comprising attaching the articulated support structure to a second articulated support structure.

10. The method of claim 9, further comprising attaching an actuator to the articulated support structure, wherein the actuator is configured to reversibly and incrementally adjust the articulated support structure and the second articulated support structure between an expanded configuration and a compressed configuration.

11. The method of claim 1, further comprising place a skirt material onto the plurality of pins before any of the strut members are placed.

12. The method of claim 11, further comprising tucking the skirt material in between at least two of the plurality of strut members.

13. The method of claim 12, wherein the tucking is performed without using suture.

14. The method of claim 11, wherein tucking is performed by pivoting a folding pin against one strut of the plurality of strut members to wrap the skirt material over the one strut.

15. The method of claim 14, further comprising inserting the pin under the one strut after wrapping the skirt material over the one strut.

16. The method of claim 15, further comprising holding the skirt material against the one strut by piercing the skirt material at two different locations with the folding pin.

17. A method of fabricating an articulated support structure, comprising:
interlinking a plurality of strut members into a flattened chain having a first end and a second end, wherein each of the plurality of strut members comprises a plurality of orifices, comprising:
placing a plurality of alignment guides through at least one orifice of each of the plurality of strut members, wherein each of the plurality of alignment guides is placed through the orifices of at least two strut members;
securing the at least two strut members together;
removing the plurality of alignment guides from the orifice; and
connecting the first end of the flattened chain to the second end of the flattened chain to form a tubular structure.

18. The method of claim 17, further comprising securing a valve comprising a plurality of valve leaflets to the support structure, wherein securing the valve to the support structure comprises sandwiching the valve leaflets between the strut members.

19. The method of claim 18, further comprising:
interlinking a second plurality of strut members into a second flattened chain having a first end and a second end, wherein each of the second plurality of strut members comprises a plurality of orifices, comprising:
placing a second plurality of alignment guides through at least one orifice of each of the second plurality of strut members, wherein each of the second plurality of alignment guides is placed through the orifices of at least two strut members of the second plurality of strut members;
securing the at least two strut members of the second plurality of strut members together;
removing the second plurality of alignment guides from the orifice; and
connecting the first end of the second flattened chain to the second end of the second flattened chain to form a second tubular structure; and
securing a skirt to the second tubular structure, wherein securing the skirt to the second tubular structure comprises sandwiching the skirt between the strut members.

20. The method of claim 17, wherein the plurality of strut members comprises a plurality of coaptation strut members, further comprising:
rotating the coaptation struts from a first position to a second position to bias the valve toward a closed configuration.

21. The method of claim 17, further comprising securing a skirt to the support structure, wherein securing the skirt to the support structure comprises sandwiching the skirt between the strut members.

* * * * *